United States Patent
Wang et al.

(10) Patent No.: US 11,873,488 B2
(45) Date of Patent: Jan. 16, 2024

(54) DOUBLE-STRANDED NUCLEIC ACID INHIBITOR MOLECULES MODIFIED WITH TM-INCREASING NUCLEOTIDES

(71) Applicant: Dicerna Pharmaceuticals, Inc., Lexington, MA (US)

(72) Inventors: Weimin Wang, Waltham, MA (US); Naim Nazef, Bedford, MA (US); Bob Dale Brown, Littleton, MA (US)

(73) Assignee: DICERNA PHARMACEUTICALS, INC., Lexington, MA (US)

(*) Notice: Subject to any disclaimer, the term of this patent is extended or adjusted under 35 U.S.C. 154(b) by 0 days.

(21) Appl. No.: 16/381,931

(22) Filed: Apr. 11, 2019

(65) Prior Publication Data
US 2019/0316125 A1 Oct. 17, 2019

Related U.S. Application Data

(60) Provisional application No. 62/778,755, filed on Dec. 12, 2018, provisional application No. 62/657,428, filed on Apr. 13, 2018.

(51) Int. Cl.
*C12N 15/113* (2010.01)

(52) U.S. Cl.
CPC ........ *C12N 15/113* (2013.01); *C12N 2310/14* (2013.01); *C12N 2310/321* (2013.01); *C12N 2310/322* (2013.01); *C12N 2310/3231* (2013.01); *C12N 2310/351* (2013.01)

(58) Field of Classification Search
CPC .............. C12N 15/113; C12N 2310/14; C12N 2310/321; C12N 2310/322; C12N 2310/3231
See application file for complete search history.

(56) References Cited

U.S. PATENT DOCUMENTS

| | | | | |
|---|---|---|---|---|
| 10,036,017 B2* | 7/2018 | Brown | ................ | C12N 15/113 |
| 10,131,912 B2* | 11/2018 | Brown | ................ | A61K 31/713 |
| 10,150,965 B2* | 12/2018 | Brown | ................ | A61K 31/713 |
| 10,351,854 B2* | 7/2019 | Brown | .................... | A61P 43/00 |
| 10,370,655 B2* | 8/2019 | Brown | ...................... | A61P 1/16 |
| 10,675,295 B2* | 6/2020 | Abrams | ............. | A61K 31/7125 |

(Continued)

FOREIGN PATENT DOCUMENTS

| CA | 2738625 C | 3/2010 |
|---|---|---|
| WO | 2010033225 A2 | 3/2010 |

(Continued)

OTHER PUBLICATIONS

Parmar et al. (ChemBioChem, 2016 vol. 17:985-989).*

(Continued)

*Primary Examiner* — Terra C Gibbs
(74) *Attorney, Agent, or Firm* — MH2 TECHNOLOGY LAW GROUP, LLP

(57) ABSTRACT

Provided herein are double-stranded nucleic acid inhibitor molecules having a sense strand with a stem loop structure and an antisense strand, where the stem portion of the stem loop structure contains one or more $T_m$-increasing nucleotides. Also provided are methods and compositions for reducing target gene expression and methods and compositions for treating a disease of interest.

36 Claims, 23 Drawing Sheets

(56) References Cited

U.S. PATENT DOCUMENTS

| | | | | |
|---|---|---|---|---|
| 10,676,742 | B2* | 6/2020 | Brown | A61K 31/713 |
| 10,752,899 | B2* | 8/2020 | Brown | A61P 35/02 |
| 2009/0137500 | A1* | 5/2009 | McSwiggen | C12N 15/113 514/44 R |
| 2011/0288147 | A1 | 11/2011 | Brown | |
| 2015/0112055 | A1 | 4/2015 | Seth et al. | |
| 2015/0259681 | A1 | 9/2015 | Swayze et al. | |
| 2016/0010090 | A1* | 1/2016 | Vagle | A61P 9/12 424/450 |
| 2016/0194638 | A1 | 7/2016 | Liang et al. | |
| 2017/0145409 | A1 | 5/2017 | Seth et al. | |
| 2018/0162897 | A1 | 6/2018 | Leumann | |

FOREIGN PATENT DOCUMENTS

| | | |
|---|---|---|
| WO | 2016057932 A1 | 4/2016 |
| WO | 2016/100401 A1 | 6/2016 |
| WO | 2018045317 A1 | 3/2018 |

OTHER PUBLICATIONS

Ganesh et al. (Mol Cancer Ther., 2016 vol. 15:2143-2154).*
Eric Minikel, CureFFI.org, Aug. 28, 2018, Antisense part III: chemistries, Comparison of Chemical Modifications.*
Kurreck et al. (Nucleic Acids Research, 2002 vol. 30:1911-1918).*
What is the difference between comprise and contain? | WikiDiff downloaded on Oct. 18, 2022.*
Kurreck et al. (Eur. J. Biochem, 2003 vol. 270:1628-1644).*
Definition of 'more of'—downloaded from https://www.collinsdictionary.com/us/dictionary/english/more-of on Feb. 23, 2023.*
International Search Report and Written Opinion dated Jul. 23, 2019 from International Application No. PCT/US2019/027021 (Authorized Officer, Shane Thomas), 7 Pages.
Grunweller et al., "Locked Nucleic Acid Oligonucleotides: The Next Generation of Antisense Agents?", Biodrugs, 2007, vol. 21, No. 4, pp. 235-243.
Hull et al., "Effects of locked nucleic acid substitutions on the stability of oligonucleotide hairpins", Nucleosides, Nucleotides and Nucleic Acids, 2012, vol. 31, No. 1, pp. 28-41.
Miyashita et al., "N-Methyl substituted 2',4'-BNANC: a highly nuclease-resistant nucleic acid analogue with high-affinity RNA selective hybridization", Chem. Commun, 2007, pp. 3765-3767.
Rahman et al., "Design, Synthesis, and Properties of 2',4'-BNANC: A Bridged Nucleic Acid Analogue", J. Am. Chem. Soc., 2008, vol. 130, pp. 4886-4896.
Prakash et al., "Antisense Oligonucleotides Containing Conformationally Constrained 2',4'-(N-Methoxy) minomethylene and 2',4'-Aminooxymethylene and 2'-O,4'-C-Aminomethylene Bridged Nucleoside Analogues Show Improved Potency In Animal Models", J. Med. Chem., 2010, vol. 53, pp. 1636-1650.
Bramsen et al. "Development of therapeutic-grade small interfering RNAs by chemical engineering", Frontiers in Genetics, Aug. 2012, vol. 3, Article 154, pp. 1-22.
Zhou et al., "Intramolecular Free-Radical Cyclization Reactions on Pentose Sugars for the Synthesis of Carba-LNA and Carba-ENA and the Application of Their Modified Oligonucleotides as Potential RNA Targeted Therapeutics", Chem. Rev., 2012, vol. 112, pp. 3808-3832.
Leumann et al., "DNA Analogues: From Supramolecular Principles to Biological Properties", Bioorganic & Medicinal Chemistry, 2002, vol. 10, pp. 841-854.
Kurreck et al., "Design of antisense oligonucleotides stabilized by locked nucleic acids", Nucleic Acids Research, 2002, vol. 30, No. 9, pp. 1911-1918.
Mitchel J. Doktycz, "Nucleic Acids: Thermal Stability and Denaturation", Encyclopedia of Life Science, 1997, Macmillan Reference Ltd, 18 pages.
Kim et al., "Bridged Nucleic Acids (BNSs) as Molecular Tools", J Biochem Mol Biol Res, 2015, vol. 1, No. 3, pp. 67-71.
Hojland et al., "New conformationally restricted DNA mimics", Nucleic Acids Symposium Series, 2008, vol. 52, No. 1, pp. 271-272.
Extended European Search Report dated Apr. 22, 2022 for corresponding European Patent Application No. 19784831.0, 12 pages.
Office Action dated Apr. 27, 2023 for corresponding Japanese Application No. 2020-554092, 5 Pages including English translation.
Makoto Koizumi, "Nucleic acids therapeutics using chemical modified oligonucleotides", Medchem News, 2014, vol. 25, No. 2, pp. 103-108 with English Abstract.
Riken Genesis web page <http://www.rikengenesis.jp /bna/technology.html>. (See p. 2 (paragraph 1) of the translation of Japanese Office Action dated Apr. 27, 2023 for corresponding Japanese Application No. 2020-554092 for a concise explanation of the relevance of this document, which is referred to as Reference 3 in the Office Action).
Riken Genesis web page <http://www.rikengenesis.jp/bna/ paper.html>. (See p. 2 (paragraph 1) of the translation of Japanese Office Action dated Apr. 27, 2023 for corresponding Japanese Application No. 2020-554092 for a concise explanation of the relevance of this document, which is referred to as Reference 4 in the Office Action).

* cited by examiner

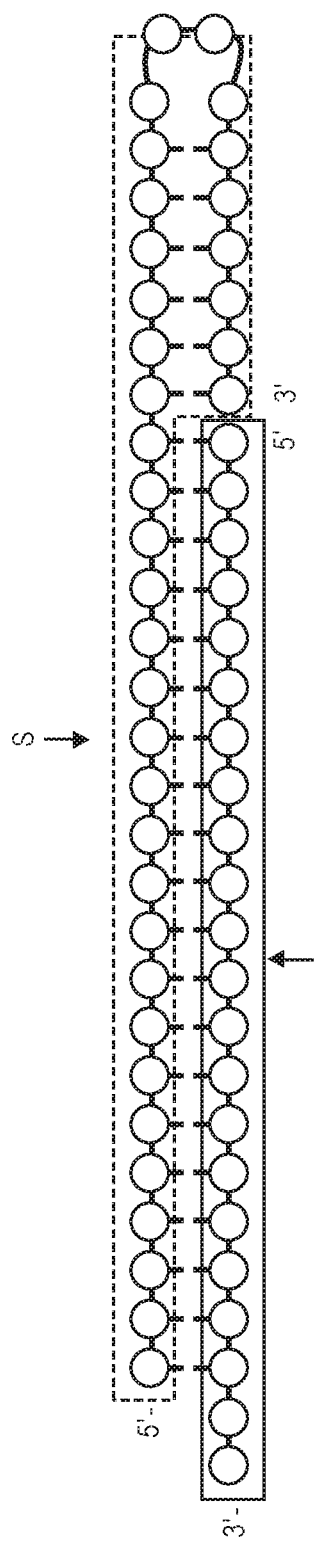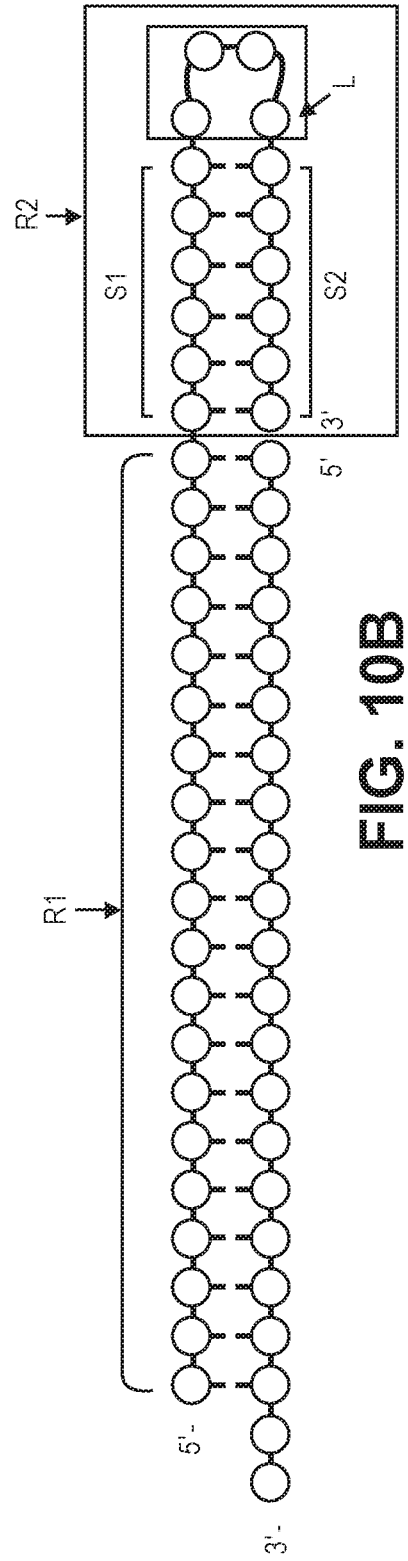

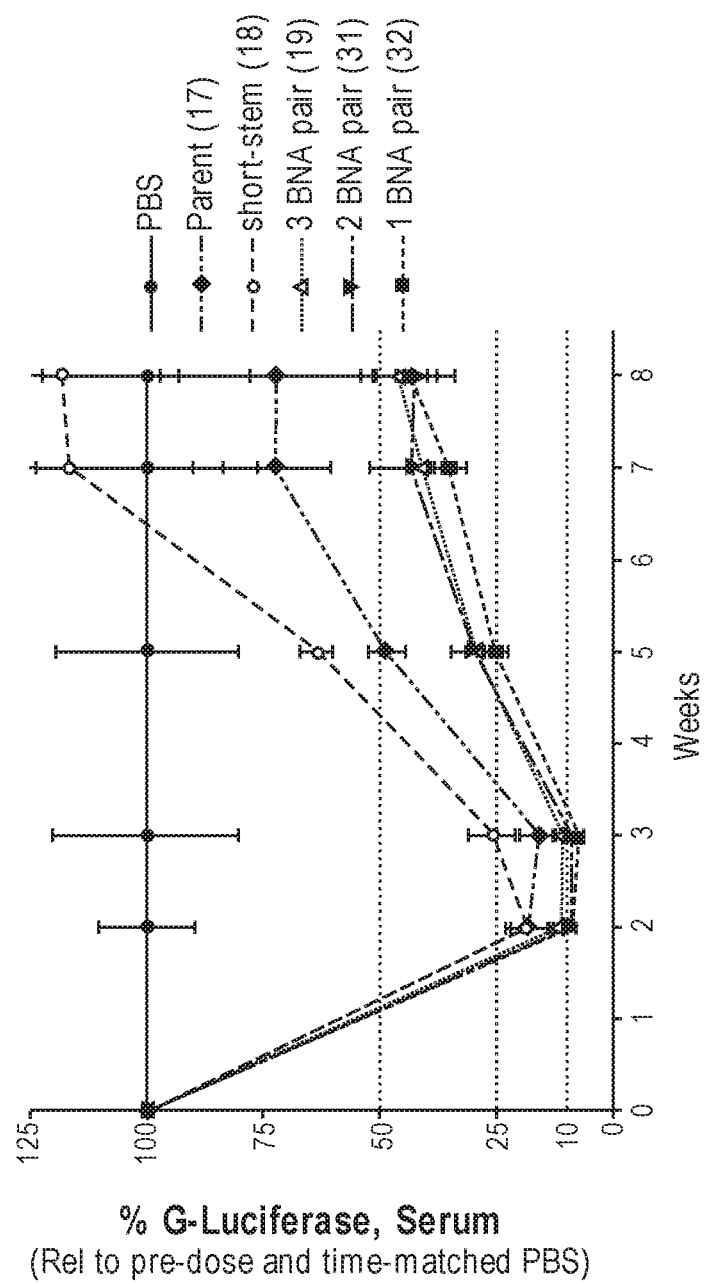

(38)

(39)

(40)

(41)

DOUBLE-STRANDED NUCLEIC ACID INHIBITOR MOLECULES MODIFIED WITH TM-INCREASING NUCLEOTIDES

CROSS REFERENCE TO RELATED APPLICATIONS

This application claims the benefit of, and relies on the filing date of, U.S. provisional patent application No. 62/657,428, filed 13 Apr. 2018 and U.S. provisional patent application No. 62/778,755, filed 12 Dec. 2018, and the entire disclosures of which are incorporated herein by reference.

BACKGROUND

Oligonucleotides are polymeric sequences of nucleotides (RNA, DNA and their analogs). Nucleic acid inhibitor molecules are oligonucleotides that modulate intracellular RNA levels and have demonstrated early promise in the treatment of cancers, viral infections and genetic disorders. Nucleic acid inhibitor molecules can modulate RNA expression through a diverse set of mechanisms, including RNA interference (RNAi).

RNAi is a conserved pathway found in most eukaryotes where double-stranded RNA molecules (dsRNA) inhibit the expression of target genes having sequences complementary to the dsRNA. In the typical RNAi pathway, a longer dsRNA molecule is cleaved by the Dicer enzyme into shorter RNA duplexes called small interfering RNAs ("siRNA"). The siRNA has been shown to associate with Dicer, trans-activating response RNA-binding protein (TRBP), and Argonaute 2 ("Ago2") to form a complex, sometimes referred to as the RNA-induced silencing complex ("RISC"). Ago2 once activated, is an endonuclease that cleaves target mRNA using the antisense strand (also called the guide strand) of the siRNA to direct the sequence specificity of the RISC complex towards cleavage of the target mRNA.

A variety of double-stranded RNAi inhibitor molecule structures have been developed over the years. For example, early work on RNAi inhibitor molecules focused on double-stranded nucleic acid molecules that mimic natural siRNAs, with each strand having sizes of 19-25 nucleotides with at least one 3'-overhang of 1 to 5 nucleotides (see, e.g., U.S. Pat. No. 8,372,968). Subsequently, longer double-stranded RNAi inhibitor molecules that get processed in vivo by the Dicer enzyme to active RNAi inhibitor molecules were developed (see, e.g., U.S. Pat. No. 8,883,996). Later work developed extended double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, WO 2010/033225, and WO 2016/100401, each of which is hereby incorporated by reference in its entirety).

In certain instances, chemically modified nucleotides have been introduced into nucleic acid inhibitor molecules to introduce properties that may be desired under specific conditions, such as conditions experienced following in vivo administration. Such chemically modified nucleotides include those designed, for example, to stabilize against nucleases or other enzymes that degrade or interfere with the structure or activity of the oligonucleotide, to increase cellular uptake of the oligonucleotide, or to improve the pharmacokinetic properties of the oligonucleotide.

However, the desire to use chemically modified nucleotides to impart desired properties to a nucleic acid inhibitor molecule, must be balanced with the competing desire to minimize any negative impact that the chemically modified nucleotides might have on the nucleic acid inhibitor molecule's activity (e.g., minimizing any reduction in the potency or duration of gene target knock down).

SUMMARY

Disclosed herein are double-stranded nucleic acid inhibitor molecules having a sense strand with a stem loop structure and a separate antisense strand, where the stem portion of the stem loop structure contains at least one $T_m$-increasing nucleotide. The double-stranded nucleic acid inhibitor molecule contains: 1) a first duplex (D1) between a first region (R1) of the sense strand (S) and the antisense strand (AS); 2) a second duplex (D2) in a second region (R2) of the sense strand that corresponds to the stem of the stem loop structure; and 3) a loop connecting the first subregion (S1) and second subregion (S2) of R2. See FIGS. 10A-C. Typically, the double-stranded nucleic acid inhibitor molecule does not contain any $T_m$-increasing nucleotides outside of the second duplex (D2). In addition, the stem loop structure typically contains a tetraloop and is located at the 5'- or 3'-end of the sense strand. Incorporating $T_m$-increasing nucleotides into the stem duplex (D2) formed at the 5'- or 3'-end of the sense strand of these double stranded nucleic acid inhibitor molecules enhances their stability and the duration of activity in vivo and allows the stem duplex (D2) to be shortened without reducing potency. See e.g. FIG. 10D; see e.g. FIG. 6 and Example 3; FIG. 9 and Example 5; and FIG. 12 and Example 6. Incorporating a single base pair of $T_m$-increasing nucleotides (i.e., 2 $T_m$-increasing nucleotides) or even a single unpaired $T_m$-increasing nucleotide into the stem duplex (D2) did not reduce potency and actually enhanced duration of activity in vivo as compared to controls without the $T_m$-increasing nucleotide. See e.g., FIGS. 15A and B and Example 5.

In certain embodiments, the double-stranded nucleic acid inhibitor molecule, comprises:
  a sense strand comprising 20-66 or 21-66 nucleotides and having a first region (R1) and a second region (R2);
  an antisense strand comprising 15-40 nucleotides, wherein the sense strand and antisense strand are separate strands;
  a first duplex (D1) formed by the first region of the sense strand and the antisense strand, wherein the first duplex has a length of 15-40 base pairs;
  wherein the second region (R2) of the sense strand comprises a first subregion (S1), a second subregion (S2) and a tetraloop (L) that joins the first and second regions, wherein the first and second regions form a second duplex (D2); and
  wherein the second duplex has a length of 1-6 base pairs and comprises at least one $T_m$-increasing nucleotide. In certain embodiments, the second duplex has a length of 3-6 base pairs. In certain embodiments, the second duplex has a length of 1-3 base pairs.

In certain embodiments, the sense strand has 24-35 nucleotides. In certain embodiments, the sense strand has 28-35 nucleotides. In certain embodiments, the sense strand has 26-30 nucleotides. In certain embodiments, the sense strand has 24 nucleotides. In certain embodiments, the sense strand has 26 nucleotides. In certain embodiments, the sense strand has 28 nucleotides. In certain embodiments, the sense strand has 30 nucleotides.

In certain embodiments, the antisense strand has 20-24 nucleotides. In certain embodiments, the antisense strand has 21-23 nucleotides. In certain embodiments, the antisense strand has 22 nucleotides. In certain embodiments, the antisense strand has a single stranded overhang of 1-6 nucleotides at its 3'-end. In certain embodiments, the single stranded overhang is 2 nucleotides in length.

In certain embodiments, the first duplex (D1) has a length of 18-30 base pairs. In certain embodiments, the first duplex (D1) has a length of 18-24 base pairs. In certain embodiments, the first duplex (D1) has a length of 19-21 base pairs. In certain embodiments, the first duplex (D1) has a length of 20 base pairs.

In certain embodiments, the second duplex (D2) has a length of 1-5 base pairs. In certain embodiments, the second duplex contains 1-10 $T_m$-increasing nucleotides and has a length of 1-5 base pairs. In certain embodiments, the second duplex (D2) has a length of 3-5 base pairs. In certain embodiments, the second duplex contains 6-10 $T_m$-increasing nucleotides and has a length of 3-5 base pairs. In certain embodiments, the second duplex contains 1-6 $T_m$-increasing nucleotides and has a length of 1-3 base pairs. In certain embodiments, the second duplex contains 6 $T_m$-increasing nucleotides and has a length of 3 base pairs. In certain embodiments, the second duplex contains 4 $T_m$-increasing nucleotides and has a length of 2 base pairs. In certain embodiments, the second duplex contains 2 $T_m$-increasing nucleotides and has a length of 1 base pair. In certain embodiments, the second duplex has a length of 3 base pairs and contains 3, 2, or 1 unpaired $T_m$-increasing nucleotides. In certain embodiments, the second duplex has a length of 1 or 2 base pairs and contains 1 or 2 unpaired $T_m$-increasing nucleotides.

In certain embodiments, the sense strand is between 28-35 nucleotides in length, the antisense strand is between 20-24 nucleotides in length, the first duplex has a length of 18-24 base pairs, and the second duplex has a length of 3-5 base pairs. In certain embodiments, the sense strand is between 24-35 nucleotides in length, the antisense strand is between 20-24 nucleotides in length, the first duplex has a length of 18-24 base pairs, and the second duplex has a length of 1-5 base pairs. In certain embodiments, the sense strand is between 24-35 nucleotides in length, the antisense strand is between 20-24 nucleotides in length, the first duplex has a length of 18-24 base pairs, and the second duplex has a length of 1-3 base pairs.

In certain embodiments, the sense strand is between 24-30 nucleotides in length, the antisense strand is between 20-24 nucleotides in length, the first duplex has a length of 18-24 base pairs, and the second duplex has a length of 1-5 base pairs, 3-5 base pairs, 1-3 base pairs, or 1-2 base pairs.

In certain embodiments, the second duplex (D2) has a length of 3 base pairs. In certain embodiments, the second duplex (D2) has a length of 2 base pairs. In certain embodiments, the second duplex (D2) has a length of 1 base pair.

In certain embodiments, the first region of the sense strand (R1) is 20 nucleotides in length and the second region of the sense strand (R2) is 6-10 nucleotides in length;
  wherein the first duplex (D1) formed by the first region of the sense strand and the antisense strand has a length of 20 base pairs;
  wherein the second duplex (D2) formed by the first subregion (S1) and second subregion (S2) of the second region of the sense strand (R2) has a length of 1-3 base pairs and the tetraloop is 4 nucleotides in length; and
  wherein the antisense strand is 22 nucleotides in length and has a single-stranded overhang of two nucleotides at its 3'-end. In certain embodiments, R2 is 6 nucleotides in length and D2 has a length of 1 base pair. In certain embodiments, R2 is 8 nucleotides in length and D2 has a length of 2 base pairs. In certain embodiments, R2 is 10 nucleotides in length and D2 has a length of 3 base pairs.

In certain embodiments, each nucleotide in the second duplex (D2) is a $T_m$-increasing nucleotide. In certain embodiments, the double-stranded nucleic acid inhibitor molecule does not contain any $T_m$-increasing nucleotides outside of the second duplex (D2).

In certain embodiments, the tetraloop is an RNA tetraloop selected from UNCG, GNRA, CUUG, A/UGNN, GGUG, RNYA, AGNN or a DNA tetraloop selected from d(GNAB), d(CNNG), or d(TNCG). In certain embodiments, the tetraloop has the sequence GAAA.

In certain embodiments, the $T_m$-increasing nucleotide is selected from the group consisting of a bicyclic nucleotide, a tricyclic nucleotide, a G-clamp and analogues thereof, a hexitol nucleotide, and a modified nucleotide, wherein the modified nucleotide is not modified at the 2'-carbon of the sugar moiety with a 2'-F or a 2'-OMe. In certain embodiments the modified nucleotide is a 5-bromo-uracil, a 5-iodo-uracil, 5-propynyl-modified pyrimidine, a 2-amino adenine, a 2-thio uridine, 5 Me-thio uridine, or a pseudo uridine.

In certain embodiments, the $T_m$-increasing nucleotide is a bicyclic nucleotide. In certain embodiments, the bicyclic nucleotide has the structure of Formula I, II, III, IV, Va, or Vb. In certain embodiments, the at least one bicyclic nucleotide has the structure of one or more of Formula Ia, Ib, Ic, Id, Ie, or If. In certain embodiments, the at least one bicyclic nucleotide has the structure of one or more of Formula IIa, IIb, IIc, or IId. In certain embodiments, the at least one bicyclic nucleotide has the structure of Formula IIIa and/or IIIb. In certain embodiments, the at least one bicyclic nucleotide has the structure of Formula IVa and/or IVb.

In certain embodiments, the bicyclic nucleotide is one or more of the following:

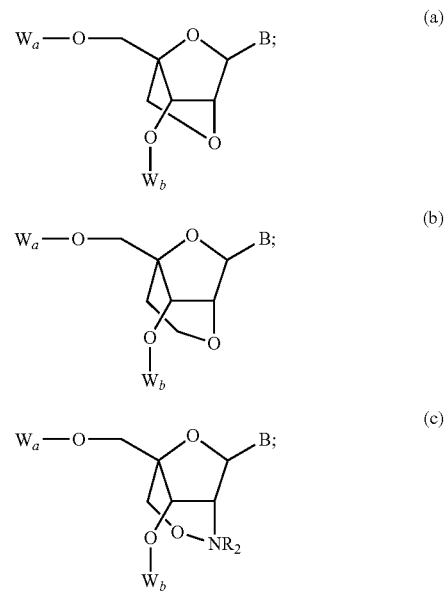

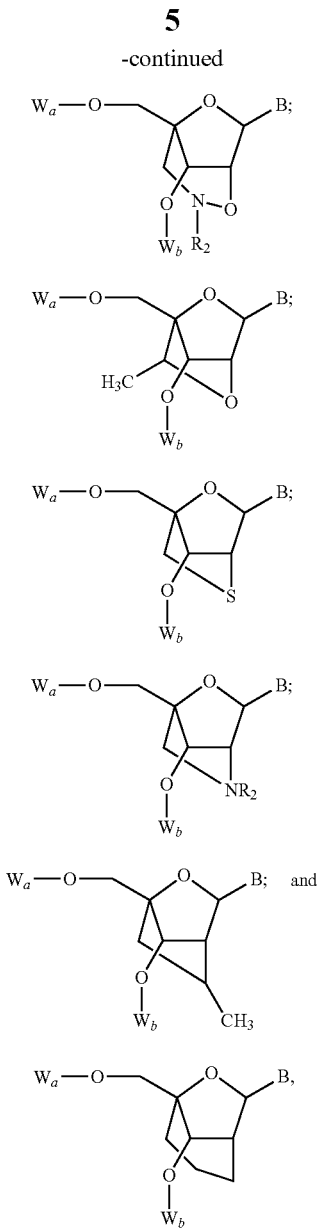

wherein B is a nucleobase, $R_2$ is H or $CH_3$ and $W_a$ and $W_b$ are each independently, H, OH, a hydroxyl protecting group, a phosphorous moiety, or an internucleotide linking group attaching the bicyclic nucleotide to another nucleotide or to an oligonucleotide and wherein at least one of $W_a$ or $W_b$ is an internucleotide linking group attaching the bicyclic nucleotide to an oligonucleotide.

In certain embodiments, the bicyclic nucleotide is:

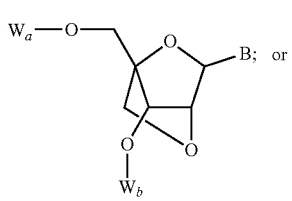

wherein B, $W_a$, and $W_b$ are as described above and $R_2$ is $CH_3$.

In certain embodiments, the bicyclic nucleotide is:

wherein B, $W_a$, and $W_b$ are as described above and $R_2$ is $CH_3$.

In certain embodiments, the bicyclic nucleotide comprises a first ring, wherein the first ring is a furanosyl, and a bridge that connects the 2'-carbon and the 4'-carbon of the furanosyl to form a second ring.

In certain embodiments, the bridge that connects the 2'-carbon and the 4'-carbon of the furanosyl is selected from the group consisting of:

a) 4'-$CH_2$—O—N(R)-2' and 4'-$CH_2$—N(R)—O-2', wherein R is H, $C_1$-$C_{12}$ alkyl, or a protecting group, including, for example, 4'-$CH_2$—NH—O-2' (also known as BNA$^{NC}$) or 4'-$CH_2$—N($CH_3$)—O-2' (also known as BNA$^{NC}$[NMe]);

b) 4'-$CH_2$-2'; 4'-$(CH_2)_2$-2'; 4'-$(CH_2)_3$-2'; 4'-$(CH_2)$—O-2' (also known as LNA); 4'-$(CH_2)$—S-2'; 4'-$(CH_2)_2$—O-2' (also known as ENA); 4'-$CH(CH_3)$—O-2' (also known as cEt); and 4'-$CH(CH_2OCH_3)$—O-2' (also known as cMOE), and analogs thereof;

c) 4'-$C(CH_3)(CH_3)$—O-2' and analogs thereof;

d) 4'-$CH_2$—N($OCH_3$)-2' and analogs thereof;

e) 4'-$CH_2$—O—N($CH_3$)-2' and analogs thereof;

f) 4'-$CH_2$—C(H)($CH_3$)-2' and analogs thereof; and g) 4'-$CH_2$—C(=$CH_2$)-2' and analogs thereof.

In certain embodiments, the double stranded nucleic acid inhibitor does not contain any bicyclic nucleotides outside of the second duplex.

In certain embodiments, the tetraloop comprises at least one ligand conjugated nucleotide. In certain embodiments, the tetraloop comprises two, three, or four ligand conjugated nucleotides. In certain embodiments, the ligand is a GalNAc. In certain embodiments, the GalNAc is conjugated to the nucleotide at the 2'-position of the sugar moiety.

In certain embodiments, the double-stranded nucleic acid inhibitor further comprises a 5'-phosphate mimic at the 5'-terminus of the sense strand and/or the antisense strand.

In certain embodiments, the double-stranded nucleic acid inhibitor molecule is formulated with a lipid nanoparticle. In certain embodiments, the lipid nanoparticle comprises core lipids and envelope lipids, wherein the core lipids comprise a first cationic lipid and a first pegylated lipid and wherein the envelope lipids comprise a second cationic lipid, a neutral lipid, a sterol, and a second pegylated lipid. In certain embodiments, the first cationic lipid is DL-048, the first pegylated lipid is DSG-mPEG, the second cationic lipid is DL-103, the neutral lipid is DSPC, the sterol is cholesterol, and the second pegylated lipid is DSPE-mPEG.

Another aspect is directed to a pharmaceutical composition comprising a therapeutically effective amount of a stem/loop-containing double-stranded nucleic acid inhibitor molecule as described herein and a pharmaceutically acceptable excipient.

Another aspect is directed to a method for reducing expression of a target gene in a subject comprising administering the double-stranded nucleic acid inhibitor molecule or pharmaceutical composition to a subject in need thereof in an amount sufficient to reduce expression of the target gene. In certain embodiments, the administering step comprises intravenous, intramuscular, or subcutaneous administration. In certain embodiments, the subject is a human.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 10A shows a schematic of an exemplary double-stranded nucleic acid inhibitor molecule with an antisense strand ("AS") and a sense strand ("S"), where the sense strand contains a stem loop structure.

FIG. 10B shows the same exemplary schematic as in FIG. 10A. In FIG. 10B, the sense strand is further divided into a first region (R1) that forms a duplex with the antisense strand (AS) and a second region (R2) that includes a loop (L) that joins a first subregion (S1) with a second subregion (S2), where S1 and S2 are sufficiently complementary to each other to form a duplex, referred to herein as a "stem" or "stem duplex."

Figure 10C:
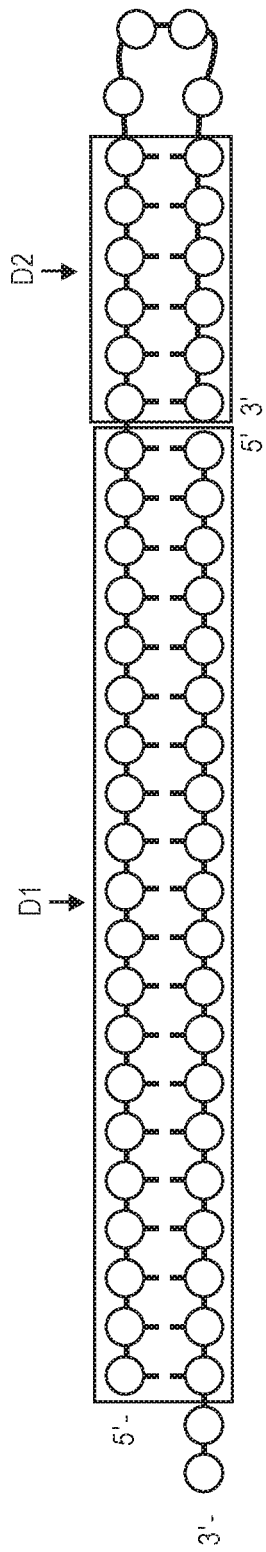

FIG. 10C shows the same exemplary schematic as in FIGS. 10A and 10B. The schematic of FIG. 10C depicts a first duplex (D1) and a second duplex (D2) in the nucleic acid inhibitor molecule. The first duplex (D1) forms between the first region of the sense strand (R1) and the antisense strand (AS). The second duplex (D2) or "stem" forms between a first subregion (51) and a second subregion (S2) of the second region (R2) of the sense strand (S).

Figure 10D:
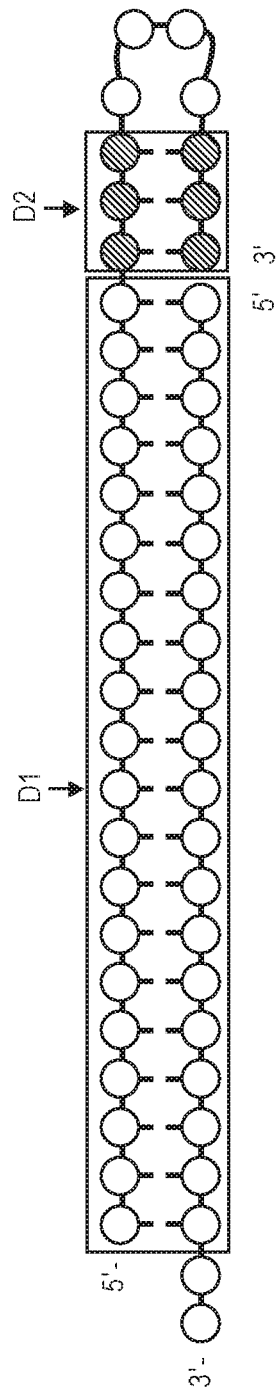

FIG. 10D shows a schematic of an exemplary double-stranded nucleic acid inhibitor molecule where the second duplex (D2) is shorter than the second duplex depicted in FIG. 10C.

Figure 11A:
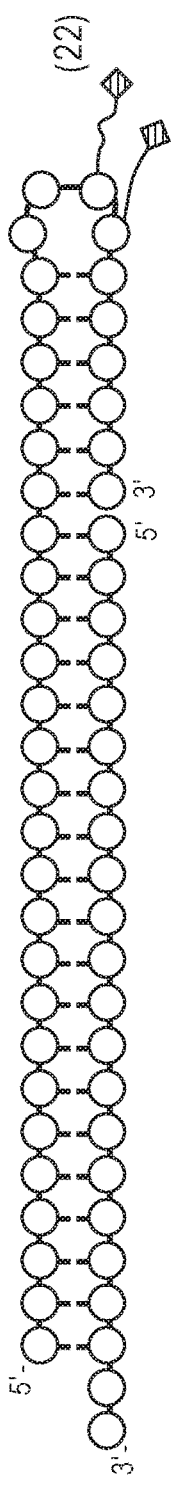

FIG. 11A schematically shows the structure of an exemplary long stem double-stranded nucleic acid inhibitor molecule ("Construct 22") that targets a gene sequence of interest, as discussed in Example 6. The sense strand of Construct 22 includes a stem duplex of 6 base pairs and a tetraloop. Two of the four nucleotides of the tetraloop are conjugated to a single GalNAc molecule.

Figure 11B:
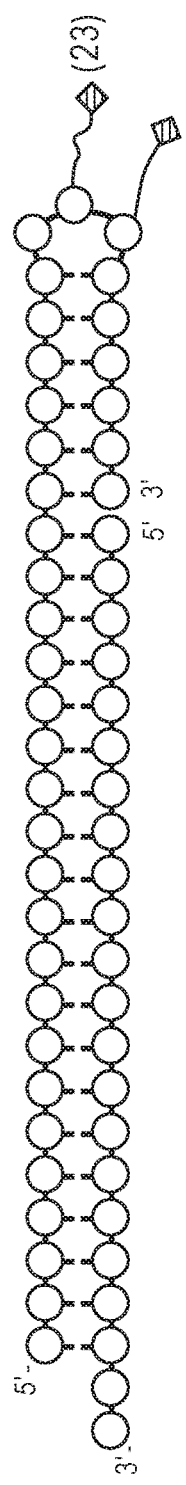

FIG. 11B schematically shows the structure of an exemplary long stem double-stranded nucleic acid inhibitor molecule ("Construct 23") that targets a gene sequence of interest, as discussed in Example 6. The sense strand of Construct 23 includes a stem duplex of 6 base pairs and a triloop. The structure of Construct 23 is identical to the structure of Construct 22, except that Construct 23 contains a triloop instead of a tetraloop.

Figure 11C:
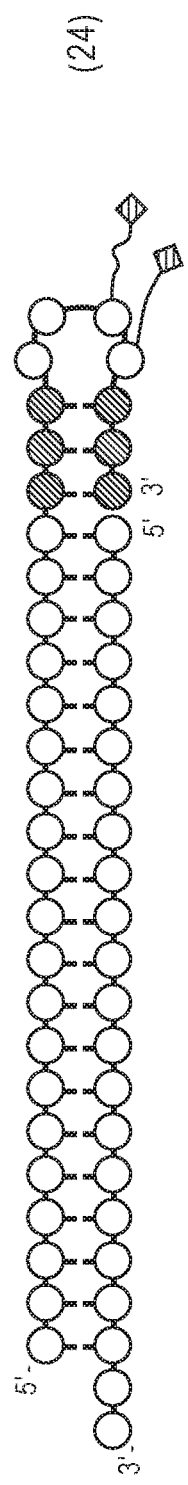

FIG. 11C schematically shows the structure of an exemplary short stem double-stranded nucleic acid inhibitor molecule ("Construct 24") that targets a gene sequence of interest, as discussed in Example 6. The sense strand of Construct 24 includes a stem duplex of 3 base pairs, wherein each nucleotide in the stem portion of the stem loop structure is a BNA, and a tetraloop. Two of the four nucleotides of the tetraloop are conjugated to a single GalNAc molecule.

Figure 11D:
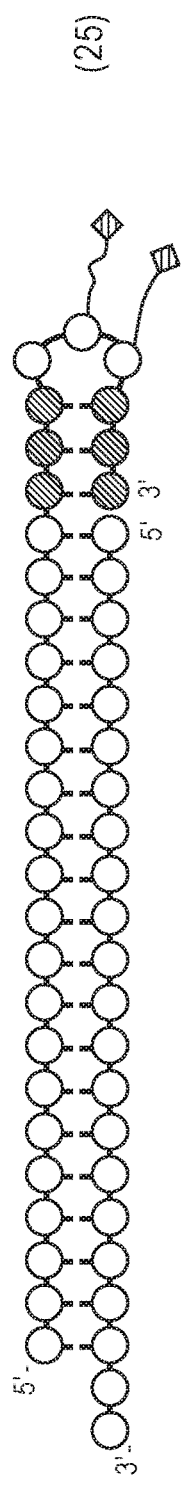

FIG. 11D schematically shows the structure of an exemplary short stem double-stranded nucleic acid inhibitor molecule ("Construct 25") that targets a gene sequence of interest, as discussed in Example 6. The sense strand of Construct 25 includes a stem duplex of 3 base pairs, wherein each nucleotide in the stem portion of the stem loop structure is a BNA, and a triloop. The structure of Construct 25 is identical to the structure of Construct 24, except that Construct 25 contains a triloop instead of a tetraloop.

Figure 11E:
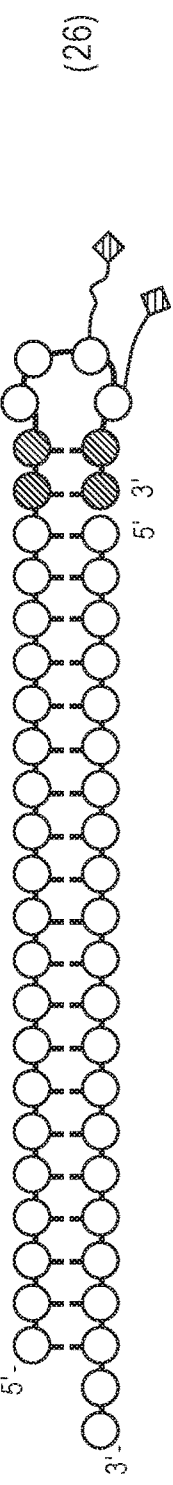

FIG. 11E schematically shows the structure of an exemplary short stem double-stranded nucleic acid inhibitor molecule ("Construct 26") that targets a gene sequence of interest, as discussed in Example 6. The sense strand of Construct 26 includes a stem duplex of 2 base pairs, wherein each nucleotide in the stem portion of the stem loop structure is a BNA, and a tetraloop. Two of the four nucleotides of the tetraloop are conjugated to a single GalNAc molecule.

Figures 11F, 11G, 11H, 11I:
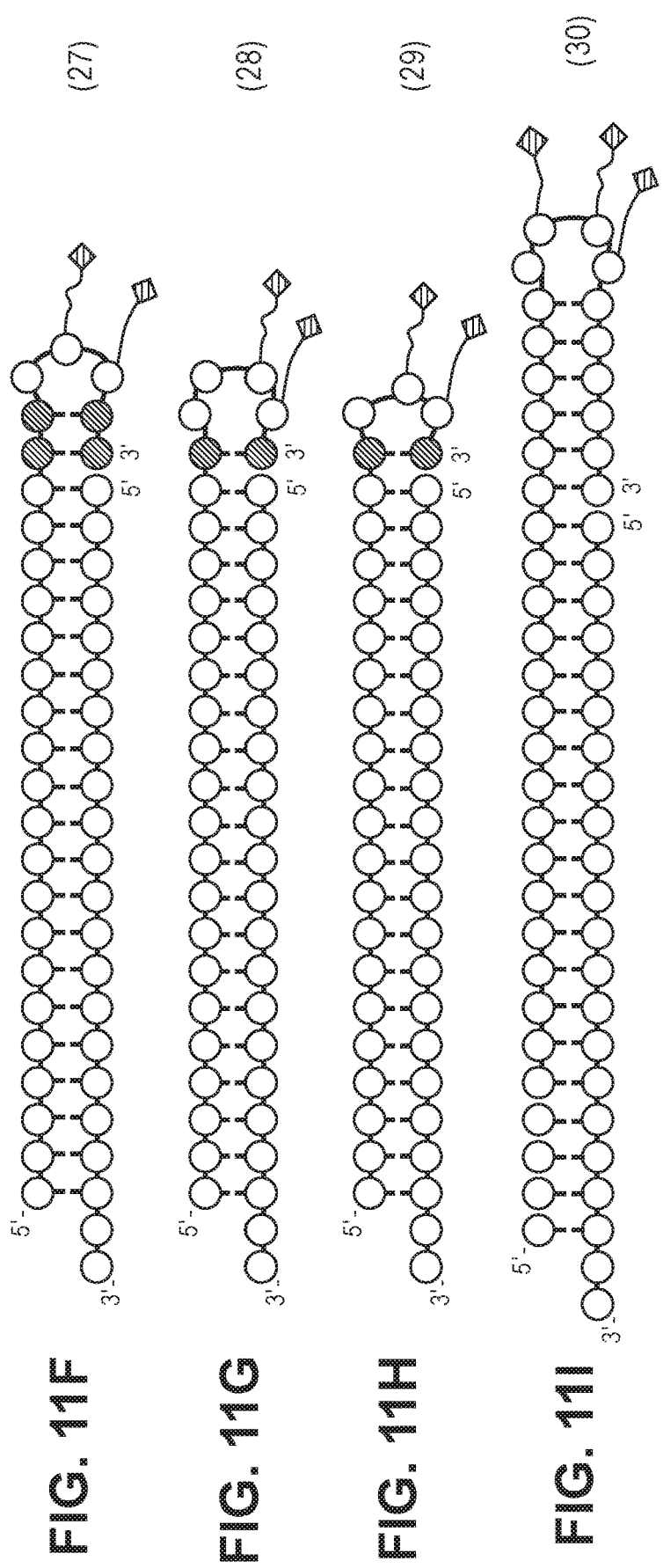

FIG. 11F schematically shows the structure of an exemplary short stem double-stranded nucleic acid inhibitor molecule ("Construct 27") that targets a gene sequence of interest, as discussed in Example 6. The sense strand of Construct 27 includes a stem duplex of 2 base pairs, wherein each nucleotide in the stem portion of the stem loop structure is a BNA, and a triloop. The structure of Construct 27 is identical to the structure of Construct 28, except that Construct 27 contains a triloop instead of a tetraloop.

FIG. 11G schematically shows the structure of an exemplary short stem double-stranded nucleic acid inhibitor molecule ("Construct 28") that targets a gene sequence of interest, as discussed in Example 6. The sense strand of Construct 28 includes a stem duplex of 1 base pair, wherein both nucleotides in the stem portion of the stem loop structure are a BNA, and a tetraloop. Two of the four nucleotides of the tetraloop are conjugated to a single GalNAc molecule.

FIG. 11H schematically shows the structure of an exemplary short stem double-stranded nucleic acid inhibitor molecule ("Construct 29") that targets a gene sequence of interest, as discussed in Example 6. The sense strand of Construct 29 includes a stem duplex of 1 base pair, wherein both nucleotides in the stem portion of the stem loop structure are a BNA, and a triloop. The structure of Construct 29 is identical to the structure of Construct 28, except that Construct 29 contains a triloop instead of a tetraloop.

FIG. 11I schematically shows the structure of an exemplary long stem double-stranded nucleic acid inhibitor molecule ("Construct 30") that targets a gene sequence of interest, as discussed in Example 6. The sense strand of Construct 30 includes a stem duplex of 6 base pairs and a tetraloop. Three of the four nucleotides of the tetraloop are conjugated to a single GalNAc molecule.

Figure 12:
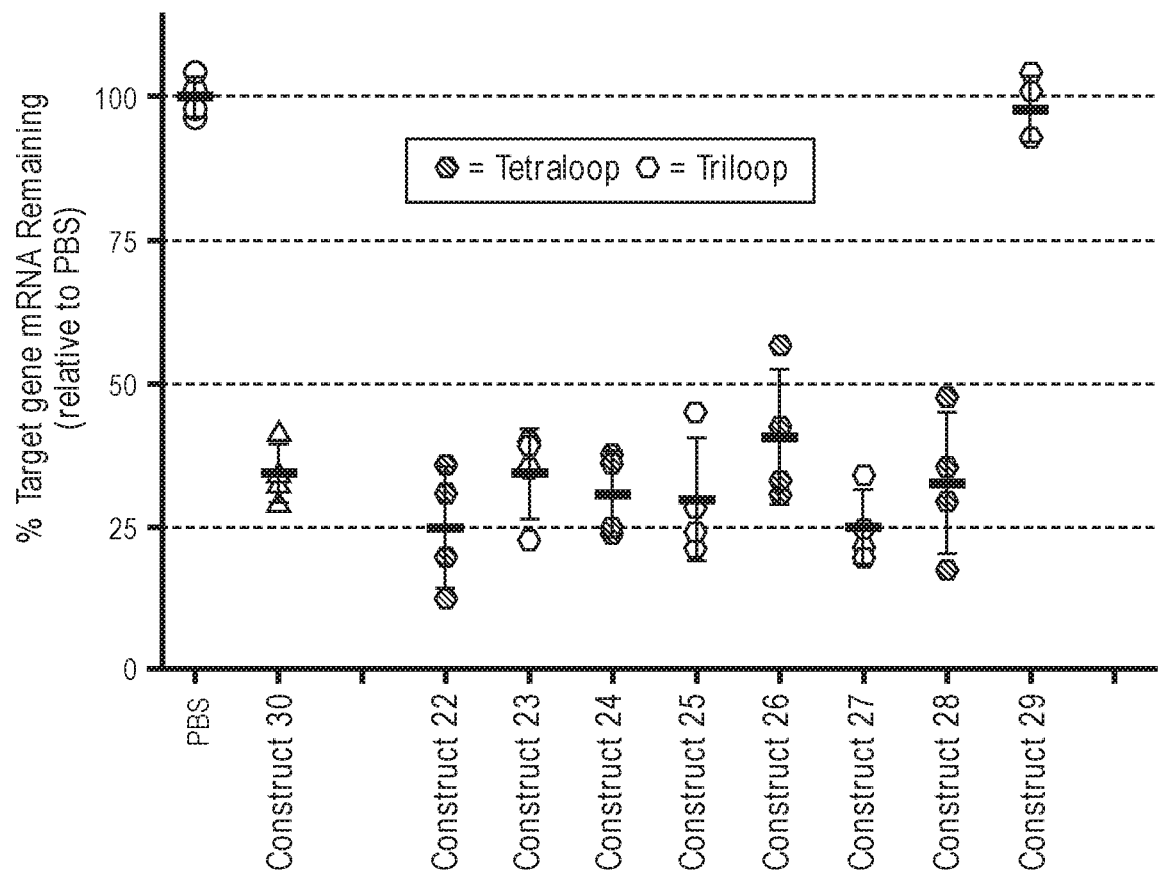

FIG. 12 shows the percent of target gene mRNA remaining 4 days after administering Constructs 22-30 (see FIGS. 11A-I) to CD-1 mice, as described in Example 6. The short stem constructs containing bicyclic nucleotides and having stems of 2 or 3 base pairs (Constructs 24-27) exhibited similar knockdown of the target gene mRNA as compared to the long stem constructs having stems of 6 base pairs (Constructs 22, 23, and 30). The triloop-containing construct having a stem of a single base pair (Construct 29) did not reduce target mRNA expression, whereas the tetraloop-containing construct having a stem of a single base pair (Construct 28) exhibited potent reduction of target mRNA expression.

Figure 13:
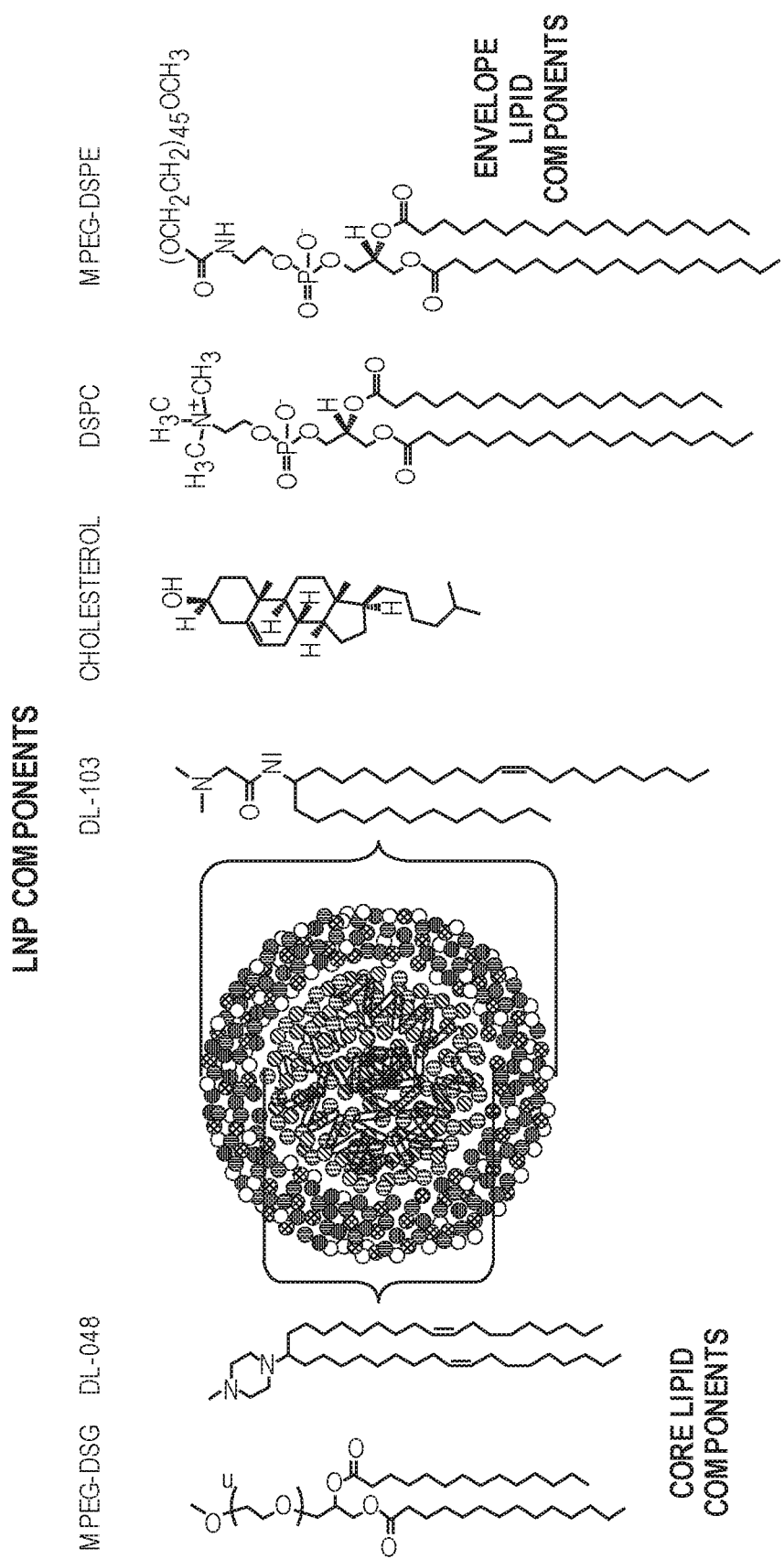

FIG. 13 shows one non-limiting embodiment of a lipid nanoparticle (LNP) that can be used to formulate the double-stranded nucleic acid inhibitor molecule. The LNP includes the following core lipids: DL-048 (cationic lipid) and DSG-mPEG (pegylated lipid), and the following envelope lipids: DL-103 (cationic lipid), DSPC, cholesterol, and DSPE-mPEG (pegylated lipid).

Figure 14A:
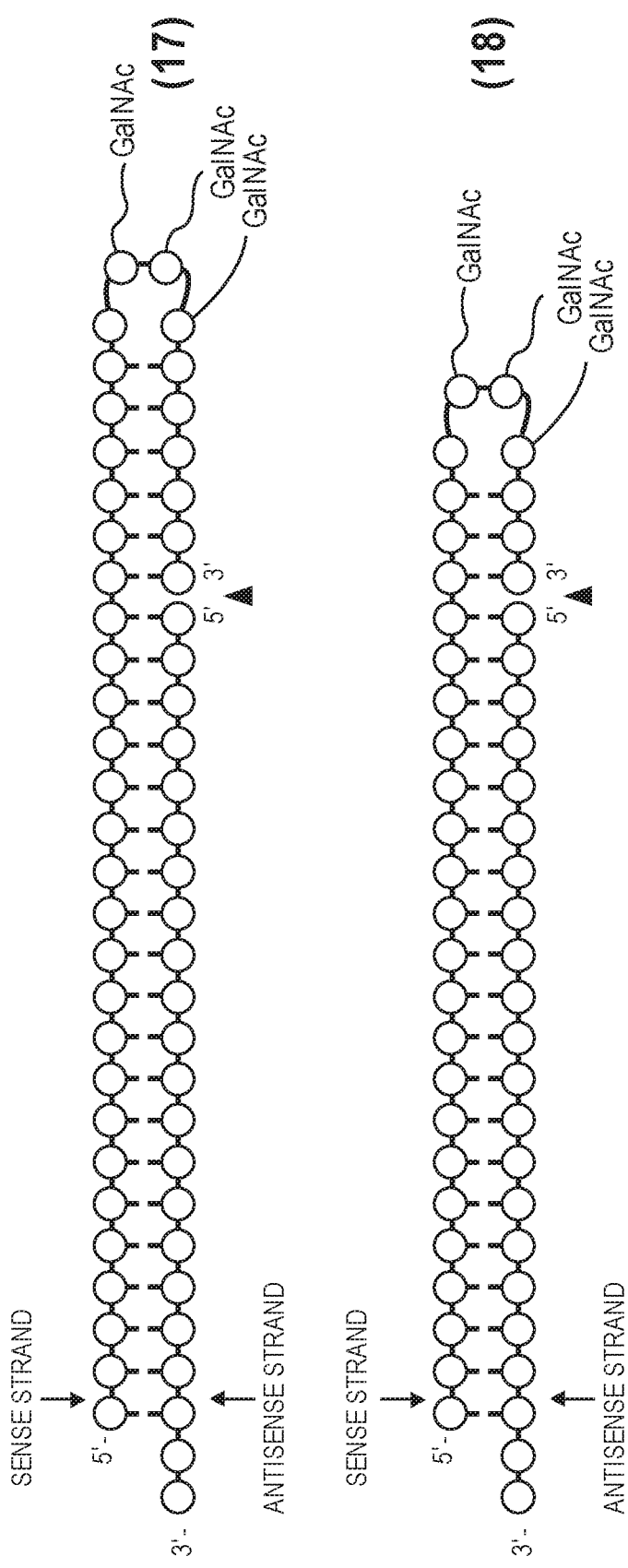

FIG. 14A schematically shows the structures of two, control double-stranded nucleic acid inhibitor molecules that target the same sequence in the human PCSK9 gene (Constructs 17 and 18), as discussed in Example 5. Constructs 17 and 18 are identical except that Construct 17 contains a long stem (6 base pairs) and Construct 18 contains a short stem (3 base pairs). Neither Construct 17 nor Construct 18 contains a $T_m$-increasing nucleotide in the stem.

Figure 14B:
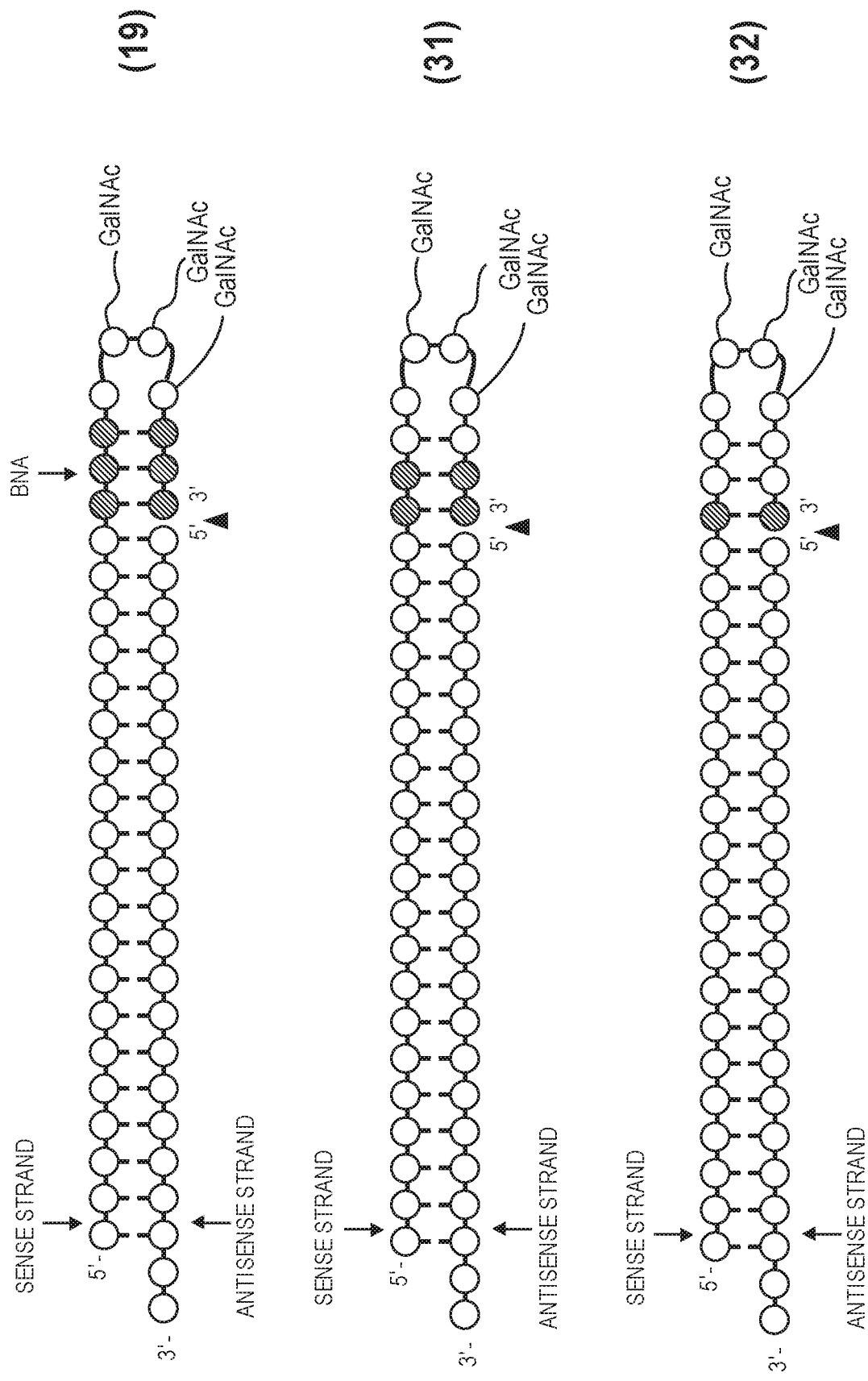

FIG. 14B schematically shows the structures of three exemplary double-stranded nucleic acid inhibitor molecules that target the same sequence in the human PCSK9 gene (Constructs 19, 31, and 32), as discussed in Example 5. Hatched circles indicate BNA. Constructs 18 and 19 are identical except that Construct 19 contains 6 bicyclic nucleotides in the stem (3 BNA base pairs). Construct 31 is identical to Construct 19 except that Construct 31 contains 4 bicyclic nucleotides in the stem (2 BNA base pairs). Construct 32 is identical to Construct 19 except that Construct 32 contains 2 bicyclic nucleotides in the stem (1 BNA base pair).

Figure 14C:
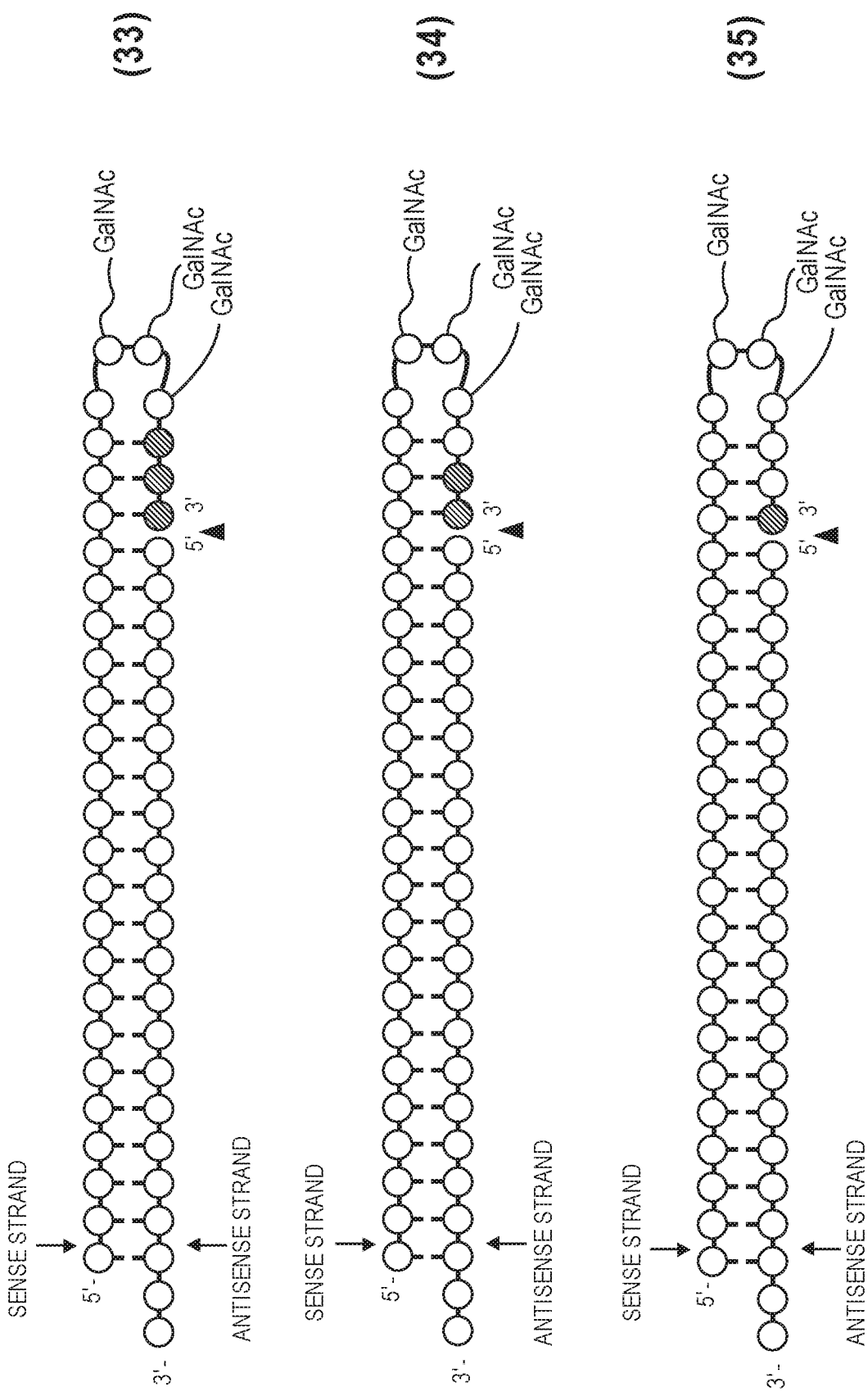

FIG. 14C schematically shows the structures of three exemplary double-stranded nucleic acid inhibitor molecules that target the same sequence in the human PCSK9 gene (Constructs 33-35), as discussed in Example 5. Hatched circles indicate BNA. Construct 33 contains 3 unpaired bicyclic nucleotides in the stem (3 BNA). Construct 34 is identical to Construct 33 except that Construct 34 contains 2 unpaired bicyclic nucleotides in the stem (2 BNA). Construct 35 is identical to Construct 33 except that Construct 35 contains 1 unpaired bicyclic nucleotide in the stem (1 BNA).

FIG. 15A shows the knockdown of *Gaussia* luciferase at weeks 2-8 following administration of Constructs 17-19, 31, and 32 (see FIGS. 14A and 14B) to C57BL/6 mice that were previously dosed with an AAV9 vector that expresses human PCSK9 target sites in the 3'-untranslated region of the *Gaussia* luciferase gene (reporter gene), as explained in Example 5. The inclusion of 3, 2, or 1 BNA base pairs in the short stem of Constructs 19, 31, and 32 improved the potency and duration of PCSK9-specific knockdown of the luciferase reporter gene as compared to the long stem and short stem controls.

Figure 15B:
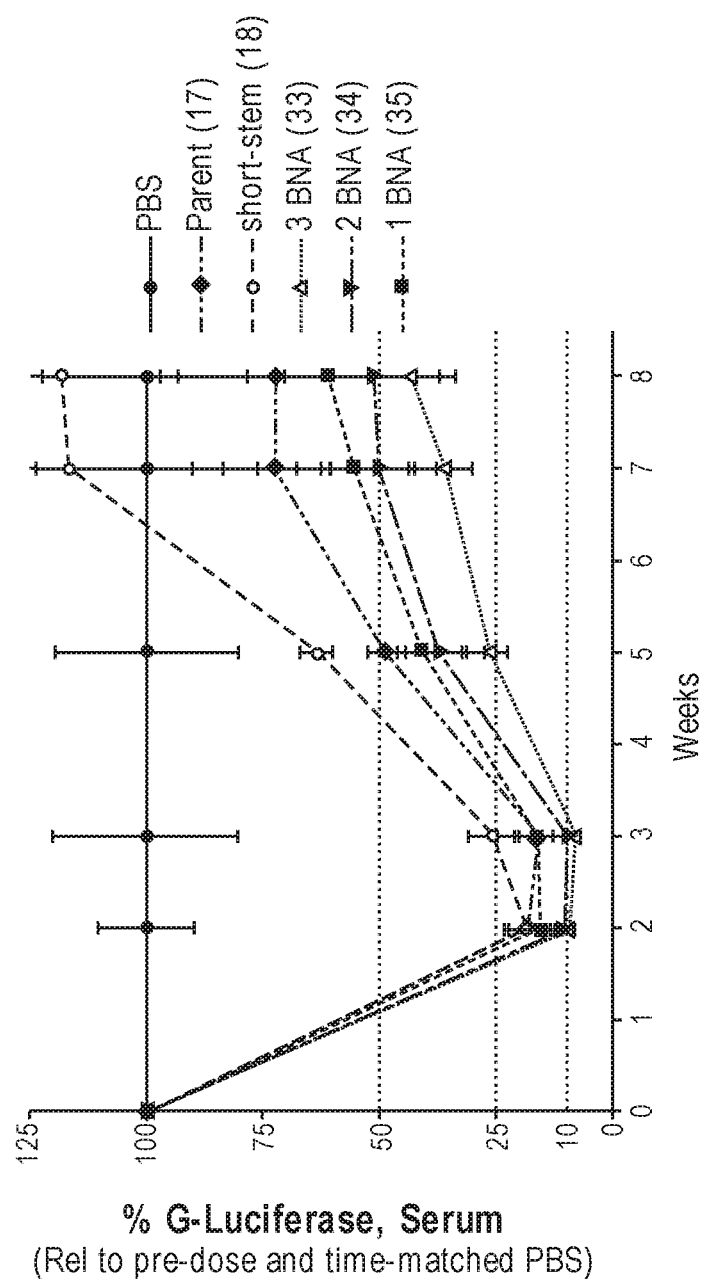

FIG. 15B shows the knockdown of *Gaussia* luciferase following administration of Constructs 33-35 (see FIG. 14C) to C57BL/6 mice that were previously dosed with an AAV9 vector that expresses human PCSK9 target sites in the 3'-untranslated region of the *Gaussia* luciferase gene (reporter gene), as explained in Example 5. The inclusion of 1, 2, or 3 unpaired bicyclic nucleotides (BNA) in the short stem of Constructs 33-35 improved the duration of PCSK9-specific knockdown of the luciferase reporter gene as compared to the long stem and short stem controls, with duration improving as the number of consecutive BNAs in the stem increased from 1 to 3.

Figure 16A:
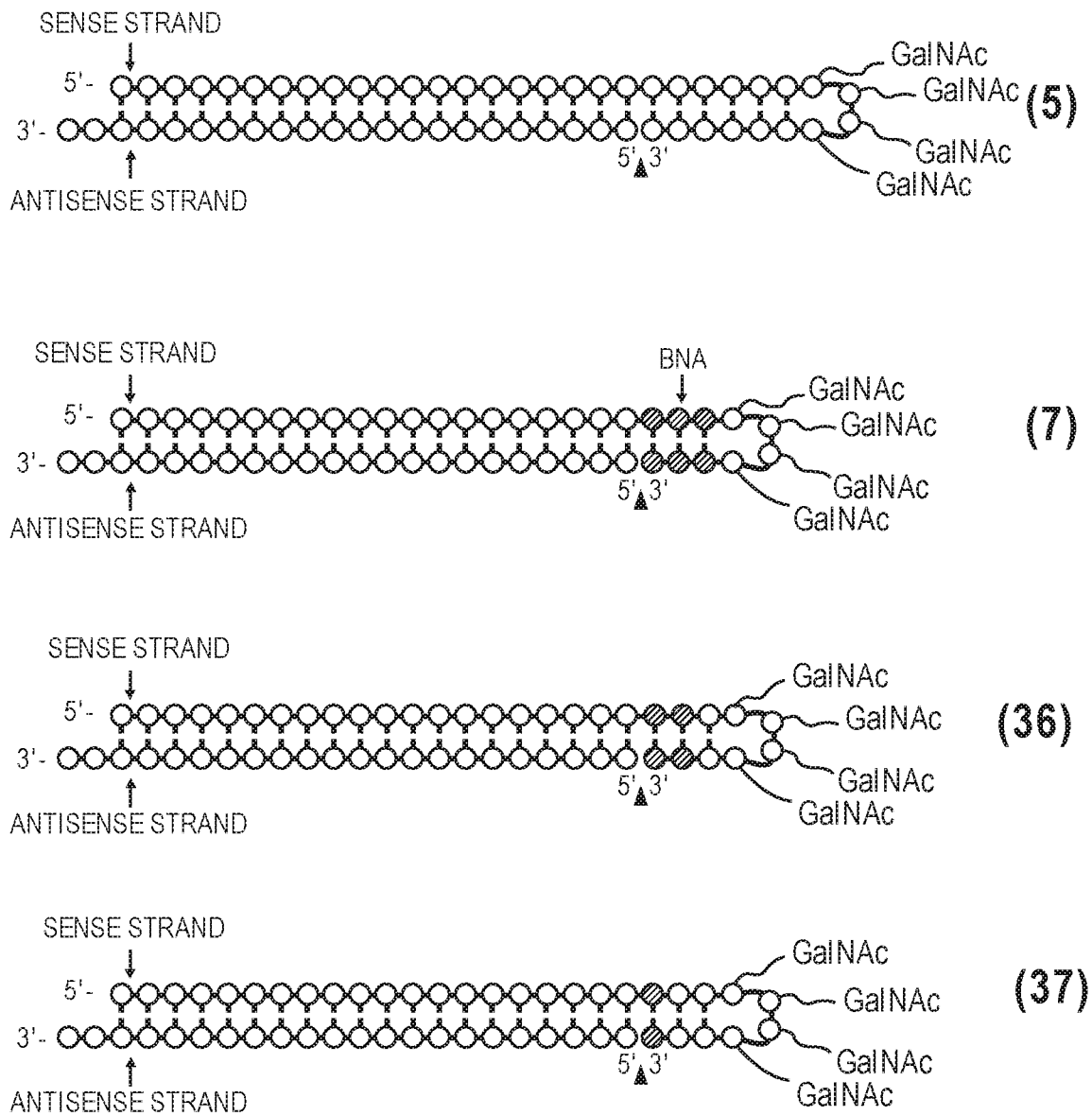

FIG. 16A schematically shows the structures of four exemplary double-stranded nucleic acid inhibitor molecules that target the same sequence in the human APOC3 gene (Constructs 5, 7, 36, and 37), as discussed in Example 7. Hatched circles indicate BNA. Constructs 5 and 7 were also used in Example 2. Construct 5 is a control containing a long stem (6 base pairs) without any $T_m$-increasing nucleotides in the stem. Construct 7 has a short stem (3 base pairs) and contains 6 bicyclic nucleotides in the stem (3 BNA base pairs). Construct 36 is identical to Construct 7 except that Construct 36 contains 4 bicyclic nucleotides in the stem (2 BNA base pairs). Construct 37 is identical to Construct 7 except that Construct 37 contains 2 bicyclic nucleotides in the stem (1 BNA base pair).

Figure 16B:
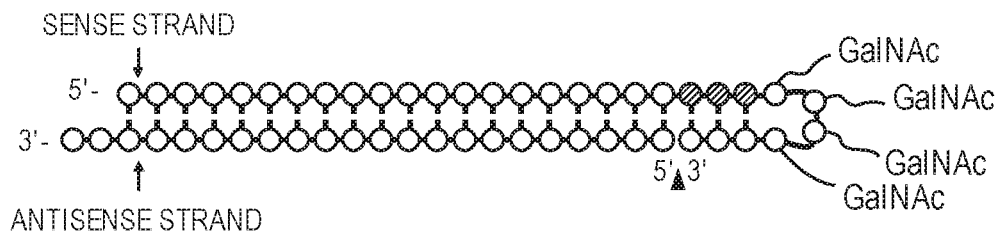
Figure 16B:
Figure 16B:
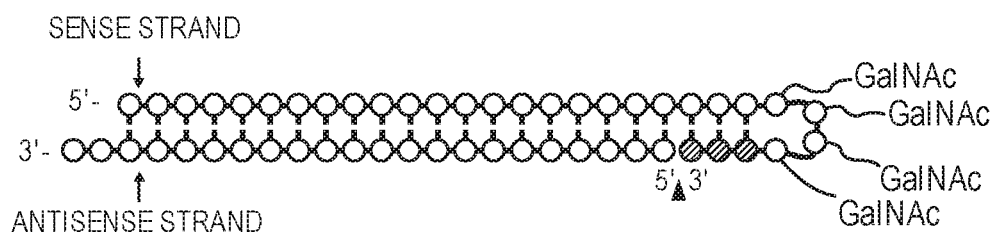
Figure 16B:
Figure 16B:
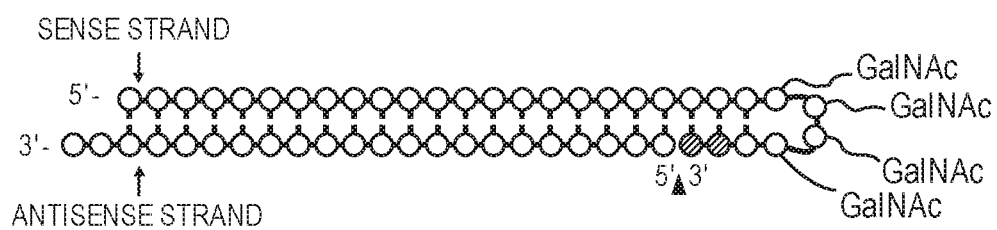
Figure 16B:
Figure 16B:
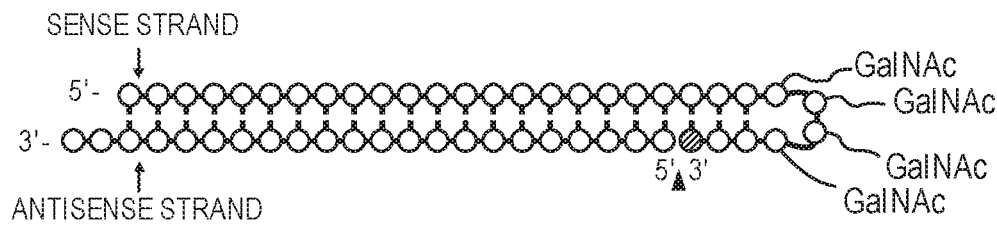
Figure 16B:

FIG. 16B schematically shows the structures of four exemplary double-stranded nucleic acid inhibitor molecules that target the same sequence in the human APOC3 gene (Constructs 38-41), as discussed in Example 7. Hatched circles indicate BNA. Construct 38 has a short stem (3 base pairs) and contains 3 unpaired bicyclic nucleotides arranged consecutively on the top strand of the stem (3 BNA—top). Construct 39 has a short stem (3 base pairs) and contains 3 unpaired bicyclic nucleotides arranged consecutively on the bottom strand of the stem (3 BNA—bottom). Construct 40 is identical to Construct 39 except that Construct 40 contains 2 unpaired bicyclic nucleotides in the stem (2 BNA). Construct 41 is identical to Construct 39 except that Construct 41 contains 1 unpaired bicyclic nucleotide in the stem (1 BNA).

Figure 17:
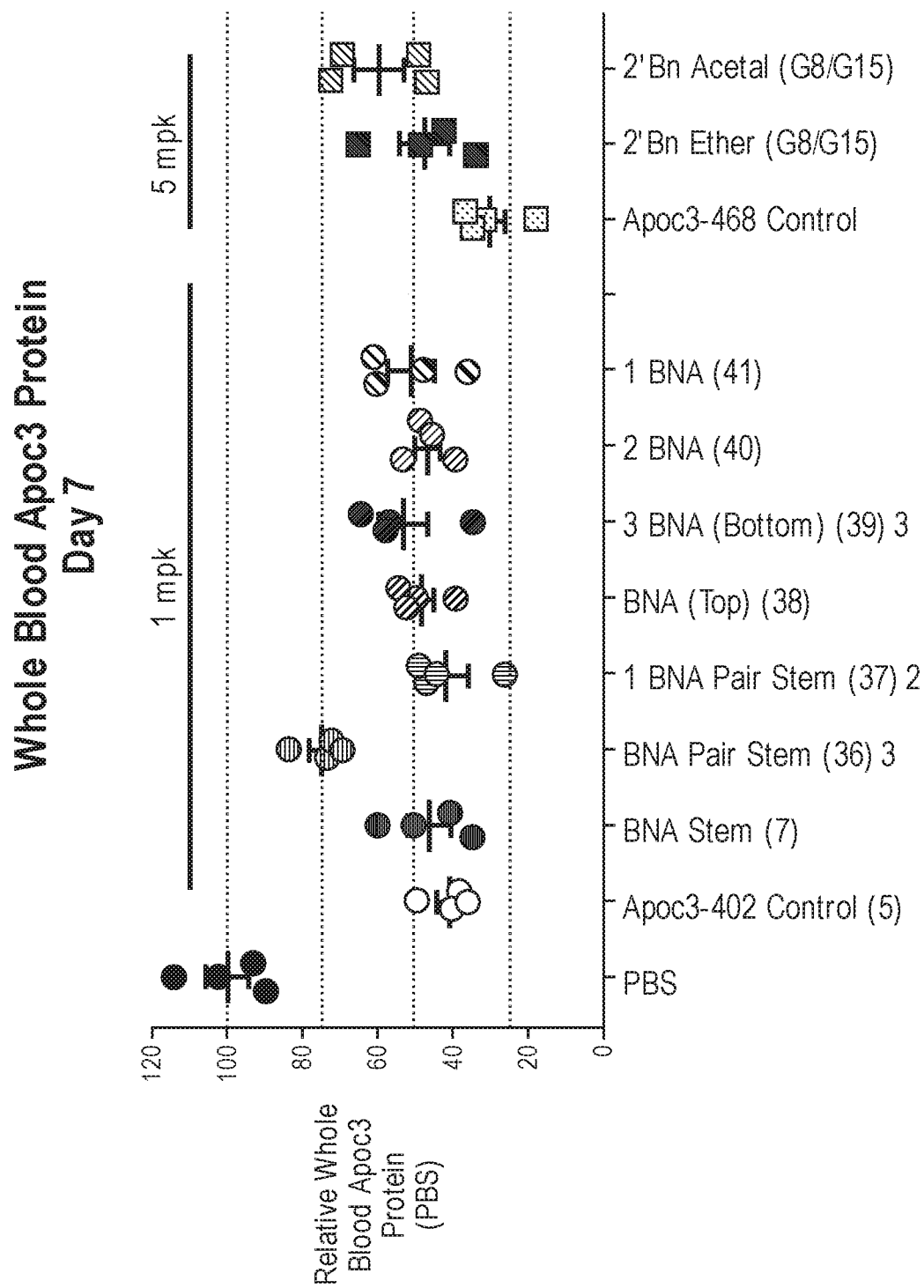

FIG. 17 shows the knockdown of APOC3 protein in whole blood at day 7 following administration of Constructs 5, 7, and 36-41 (see FIGS. 16A and 16B) to CD-1 mice, as explained in Example 7.

DEFINITIONS

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

Administer: As used herein, "administering" a composition to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Acyl: As used herein, the term "acyl" refers to an alkylcarbonyl, cycloalkylcarbonyl and arylcarbonyl moiety.

Alkoxy: As used herein, the term "alkoxy" refers to an alkyl group attached to a molecular moiety through an oxygen atom.

Alkenyl: As used herein, the term "alkenyl" refers to straight or branched chain hydrocarbyl groups having at least one carbon-carbon double bond and having in the range of about 2 to about 20 carbon atoms. "Substituted alkenyl" refers to alkenyl groups further bearing one or more substituents. As used herein, "lower alkenyl" refers to alkenyl moieties having from 2 to about 6 carbon atoms.

Alkyl: As used herein, the term "alkyl" refers to straight or branched chain hydrocarbyl groups having from 1 up to about 20 carbon atoms. Whenever it appears herein, a numerical range, such as "$C_1$-$C_6$ alkyl" means that an alkyl group may comprise only 1 carbon atom, 2 carbon atoms, 3 carbon atoms, etc., up to and including 6 carbon atoms, although the term "alkyl" also includes instances where no numerical range of carbon atoms is designated. For example, the term "alkyl" can refer to a sub-range between $C_1$-$C_{10}$ (e.g. $C_1$-$C_6$). "Substituted alkyl" refers to alkyl moieties bearing substituents. As used herein, "lower alkyl" refers to alkyl moieties having from 1 to about 6 carbon atoms.

Alkynyl: As used herein, "alkynyl" refers to straight or branched chain hydrocarbyl groups having at least one carbon-carbon triple bond and having in the range of about 2 to about 20 carbon atoms. "Substituted alkynyl" refers to alkynyl groups further bearing one or more substituents. As used herein, "lower alkynyl" refers to alkynyl moieties having from about 2 to about 6 carbon atoms.

Antisense strand: A double-stranded nucleic acid inhibitor molecule comprises two oligonucleotide strands: an antisense strand and a sense strand. The antisense strand or a region thereof is partially, substantially or fully complementary to a corresponding region of a target nucleic acid. In addition, the antisense strand of the double-stranded nucleic acid inhibitor molecule or a region thereof is partially, substantially or fully complementary to the sense strand of the double-stranded nucleic acid inhibitor molecule or a region thereof. In certain embodiments, the antisense strand may also contain nucleotides that are non-complementary to the target nucleic acid sequence. The non-complementary nucleotides may be on either side of the complementary sequence or may be on both sides of the complementary sequence. In certain embodiments, where the antisense strand or a region thereof is partially or substantially complementary to the sense strand or a region thereof, the non-complementary nucleotides may be located between one or more regions of complementarity (e.g., one or more mismatches). The antisense strand of a double-stranded nucleic acid inhibitor molecule is also referred to as the guide strand.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12% 11%, 10% 9% 8% 7% 6% 5% 4% 3% 2%, 1%, or less in either direction (greater than or less than) of the stated reference value unless otherwise stated or otherwise evident from the context (except where such number would exceed 100% of a possible value).

Aryl: As used herein, the term "aryl" refers to an aromatic monocyclic or multicyclic groups having in the range of 5 up to 19 carbon atoms. "Substituted aryl" refers to aryl groups further bearing one or more substituents.

Bicyclic nucleotide: As used herein, the term "bicyclic nucleotide" refers to a nucleotide comprising a bicyclic sugar moiety.

Bicyclic sugar moiety: As used herein, the term "bicyclic sugar moiety" refers to a modified sugar moiety comprising a 4 to 7 membered ring (including but not limited to a furanosyl) comprising a bridge connecting two atoms of the 4 to 7 membered ring to form a second ring, resulting in a bicyclic structure. Typically, the 4 to 7 membered ring is a sugar. In some embodiments, the 4 to 7-member ring is a furanosyl. In certain embodiments, the bridge connects the 2'-carbon and the 4'-carbon of the furanosyl.

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. "Fully complementary" or 100% complementarity refers to the situation in which each nucleotide monomer of a first oligonucleotide strand or of a segment of a first oligonucleotide strand can form a base pair with each nucleotide monomer of a second oligonucleotide strand or of a segment of a second oligonucleotide strand. Less than 100% complementarity refers to the situation in which some, but not all, nucleotide monomers of two oligonucleotide strands (or two segments of two oligonucleotide strands) can form base pairs with each other. "Substantial complementarity" refers to two oligonucleotide strands (or segments of two oligonucleotide strands) exhibiting 90% or greater complementarity to each other. "Sufficiently complementary" refers to complementarity between a target mRNA and a nucleic acid inhibitor molecule, such that there is a reduction in the amount of protein encoded by a target mRNA.

Complementary strand: As used herein, the term "complementary strand" refers to a strand of a double-stranded nucleic acid inhibitor molecule that is partially, substantially or fully complementary to the other strand.

Cycloalkyl: As used herein, the term "cycloalkyl" refers to cyclic (i.e., ring-containing) hydrocarbon groups containing 3 to 12 carbons, for example, 3 to 8 carbons and, for example, 3 to 6 carbons. "Substituted cycloalkyl" refers to cycloalkyl groups further bearing one or more substituents.

Deoxyribofuranosyl: As used herein, the term "deoxyribofuranosyl" refers to a furanosyl that is found in naturally occurring DNA and has a hydrogen group at the 2'-carbon, as illustrated below:

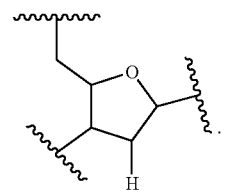 [SMILES: *CC1OC(*)CC1*]

Deoxyribonucleotide: As used herein, the term "deoxyribonucleotide" refers to a natural nucleotide (as defined herein) or modified nucleotide (as defined herein) which has a hydrogen group at the 2'-position of the sugar moiety.

dsRNAi inhibitor molecule: As used herein, the term "dsRNAi inhibitor molecule" refers to a double-stranded nucleic acid inhibitor molecule having a sense strand (passenger) and antisense strand (guide), where the antisense strand or part of the antisense strand is used by the Argonaute 2 (Ago2) endonuclease in the cleavage of a target m RNA.

Duplex: As used herein, the term "duplex," in reference to nucleic acids (e.g., oligonucleotides), refers to a structure formed through complementary base pairing of two antiparallel sequences of nucleotides.

Excipient: As used herein, the term "excipient" refers to a non-therapeutic agent that may be included in a composition, for example to provide or contribute to a desired consistency or stabilizing effect.

Furanosyl: As used herein, the term "furanosyl" refers to a structure comprising a 5-membered ring with four carbon atoms and one oxygen atom.

Halo: As used herein, the terms "halo" and "halogen" are interchangeable and refer to an atom selected from fluorine, chlorine, bromine and iodine.

Heterocycle: As used herein, the terms "heterocycle" or "heterocyclic" refer to non-aromatic cyclic (i.e., ring-containing) groups containing one or more heteroatoms (e.g., N, O, S, or the like) as part of the ring structure and having in the range of 3 up to 14 carbon atoms. "Substituted heterocyclic" or "substituted heterocycle" refer to heterocyclic groups further bearing one or more substituents.

Internucleotide linking group: As used herein, the term "internucleotide linking group" or "internucleotide linkage" refers to a chemical group capable of covalently linking two nucleoside moieties. Typically, the chemical group is a phosphorus-containing linkage group containing a phospho or phosphite group. Phospho linking groups are meant to include a phosphodiester linkage, a phosphorodithioate linkage, a phosphorothioate linkage, a phosphotriester linkage, a thionoalkylphosphonate linkage, a thionoalkylphosphotriester linkage, a phosphoramidite linkage, a phosphonate linkage and/or a boranophosphate linkage. Many phosphorus-containing linkages are well known in the art, as disclosed, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050. In other embodiments, the oligonucleotide contains one or more internucleotide linking groups that do not contain a phosphorous atom, such short chain alkyl or cycloalkyl internucleotide linkages, mixed heteroatom and alkyl or cycloalkyl internucleotide linkages, or one or more short chain heteroatomic or heterocyclic internucleotide linkages, including, but not limited to, those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; and amide backbones. Non-phosphorous containing linkages are well known in the art, as disclosed, for example, in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Loop: As used herein, the term "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins and tetraloops.

Melting Temperature: As used herein, "melting temperature" or "$T_m$" means the temperature at which the two strands of a duplex nucleic acid separate. $T_m$ is often used as a measure of duplex stability or the binding affinity of two strands of complementary nucleic acids or portions thereof. $T_m$ can be measured by using the UV spectrum to determine the formation and breakdown (melting) of hybridization. Base stacking, which occurs during hybridization, is accompanied by a reduction in UV absorption (hypochromicity). Consequently, a reduction in UV absorption indicates a higher $T_m$.

Modified nucleobase: As used herein, the term "modified nucleobase" refers to any nucleobase that is not a natural nucleobase or a universal nucleobase. Suitable modified nucleobases include diaminopurine and its derivatives, alkylated purines or pyrimidines, acylated purines or pyrimidines thiolated purines or pyrimidines, and the like. Other suitable modified nucleobases include analogs of purines and pyrimidines. Suitable analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, hypoxanthine, xanthine, 2-aminopurine, 6-hydroxyaminopurine, nitropyrrolyl, nitroindolyl and difluorotolyl, 6-thiopurine and 2,6-diaminopurine nitropyrrolyl, nitroindolyl and difluorotolyl. Typically, a nucleobase contains a nitrogenous base. In certain embodiments, the nucleobase does not contain a nitrogen atom. See e.g., U.S. Published Patent Application No. 20080274462.

Modified nucleoside: As used herein, the term "modified nucleoside" refers to a heterocyclic nitrogenous base in N-glycosidic linkage with a sugar (e.g., deoxyribose or ribose or analog thereof) that is not linked to a phosphate group or a modified phosphate group (as defined herein) and that contains one or more of a modified nucleobase (as defined herein), a universal nucleobase (as defined herein) or a modified sugar moiety (as defined herein). The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). Suitable modified or universal nucleobases or modified sugars in the context of the present disclosure are described herein.

Modified nucleotide: As used herein, the term "modified nucleotide" refers to a heterocyclic nitrogenous base in N-glycosidic linkage with a sugar (e.g., ribose or deoxyribose or analog thereof) that is linked to a phosphate group or a modified phosphate group (as defined herein) and contains one or more of a modified nucleobase (as defined herein), a universal nucleobase (as defined herein), or a modified sugar moiety (as defined herein). The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). Suitable modified or universal nucleobases, modified sugar moieties, or modified phosphate groups in the context of the present disclosure are described herein.

Modified phosphate group: As used herein, the term "modified phosphate group" refers to a modification of the phosphate group that does not occur in natural nucleotides and includes non-naturally occurring phosphate mimics as described herein, including phosphate mimics that include a phosphorous atom and anionic phosphate mimics that do not include phosphate (e.g. acetate). Modified phosphate groups also include non-naturally occurring internucleotide linking groups, including both phosphorous-containing internucleotide linking groups, including, for example, phosphorothioate, and non-phosphorous containing linking groups, as described herein.

Modified sugar moiety: As used herein, a "modified sugar moiety" refers to a substituted sugar moiety (as defined herein) or a sugar analog (as defined herein).

Natural nucleobase: As used herein, the term "natural nucleobase" refers to the five primary, naturally occurring heterocyclic nucleobases of RNA and DNA, i.e., the purine bases: adenine (A) and guanine (G), and the pyrimidine bases: thymine (T), cytosine (C), and uracil (U).

Natural nucleoside: As used herein, the term "natural nucleoside" refers to a natural nucleobase (as defined herein) in N-glycosidic linkage with a natural sugar moiety (as defined herein) that is not linked to a phosphate group.

Natural nucleotide: As used herein, the term "natural nucleotide" refers to a natural nucleobase (as defined herein) in N-glycosidic linkage with a natural sugar moiety (as defined herein) that is linked to a phosphate group.

Natural sugar moiety: As used herein, the term "natural sugar moiety" refers to a ribofuranosyl (as defined herein) or a deoxyribofuranosyl (as defined herein).

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. The nucleic acid inhibitor molecule may include ribonucleotides, deoxyribonucleotides, and/or modified nucleotides.

Nucleobase: As used herein, the term "nucleobase" refers to a natural nucleobase (as defined herein), a modified nucleobase (as defined herein), or a universal nucleobase (as defined herein).

Nucleoside: As used herein, the term "nucleoside" refers to a natural nucleoside (as defined herein) or a modified nucleoside (as defined herein).

Nucleotide: As used herein, the term "nucleotide" refers to a natural nucleotide (as defined herein) or a modified nucleotide (as defined herein).

Overhang: As used herein, the term "overhang" refers to terminal non-base pairing nucleotide(s) at either end of either strand of a double-stranded nucleic acid inhibitor molecule. In certain embodiments, the overhang results from one strand or region extending beyond the terminus of the complementary strand to which the first strand or region forms a duplex. One or both of two oligonucleotide regions that can form a duplex through hydrogen bonding of base pairs may have a 5'- and/or 3'-end that extends beyond the 3'- and/or 5'-end of complementarity shared by the two polynucleotides or regions. The single-stranded region extending beyond the 3'- and/or 5'-end of the duplex is referred to as an overhang.

Pharmaceutical composition: As used herein, the term "pharmaceutical composition" comprises a pharmacologically effective amount of a double-stranded nucleic acid inhibitor molecule and a pharmaceutically acceptable excipient (as defined herein).

Pharmaceutically acceptable excipient: As used herein, the term "pharmaceutically acceptable excipient" means that the excipient is one that is suitable for use with humans and/or animals without undue adverse side effects (such as toxicity, irritation, and allergic response) commensurate with a reasonable benefit/risk ratio.

Phosphate mimic: As used herein, the term "phosphate mimic" refers to a chemical moiety at the 5'-terminal end of an oligonucleotide that mimics the electrostatic and steric properties of a phosphate group. Many phosphate mimics have been developed that can be attached to the 5'-end of an oligonucleotide (see, e.g., U.S. Pat. No. 8,927,513; Prakash et al. NUCLEIC ACIDS RES., 2015, 43(6):2993-3011). Typically, these 5'-phosphate mimics contain phosphatase-resistant linkages. Suitable phosphate mimics include 5'-phosphonates, such as 5'-methylenephosphonate (5'-MP) and 5'-(E)-vinylphosphonate (5'-VP) and 4'-phosphate analogs that are bound to the 4'-carbon of the sugar moiety (e.g., a ribose or deoxyribose or analog thereof) of the 5'-terminal nucleotide of an oligonucleotide, such as 4'-oxymethylphosphonate, 4'-thiomethylphosphonate, or 4'-aminomethylphosphonate, as described in International Publication No. WO 2018/045317, which is hereby incorporated by reference in its entirety. In certain embodiments, the 4'-oxymethylphosphonate is represented by the formula —O—CH$_2$—PO(OH)$_2$ or —O—CH$_2$—PO(OR)$_2$, where R is independently selected from H, CH$_3$, an alkyl group, or a protecting group. In certain embodiments, the alkyl group is CH$_2$CH$_3$. More typically, R is independently selected from H, CH$_3$, or CH$_2$CH$_3$. Other modifications have been developed for the 5'-end of oligonucleotides (see, e.g., WO 2011/133871).

Protecting group: As used herein, the term "protecting group" is used in the conventional chemical sense as a group which reversibly renders unreactive a functional group under certain conditions of a desired reaction. After the desired reaction, protecting groups may be removed to deprotect the protected functional group. All protecting groups should be removable under conditions which do not degrade a substantial proportion of the molecules being synthesized.

Reduce(s): The term "reduce" or "reduces" as used herein refers to its meaning as is generally accepted in the art. With reference to nucleic acid inhibitor molecules, the term generally refers to the reduction in the expression of a gene, or level of RNA molecules or equivalent RNA molecules encoding one or more proteins or protein subunits, or activity of one or more proteins or protein subunits, below that observed in the absence of the nucleic acid inhibitor molecules.

Ribofuranosyl: As used herein, the term "ribofuranosyl" refers to a furanosyl that is found in naturally occurring RNA and has a hydroxyl group at the 2'-carbon, as illustrated below:

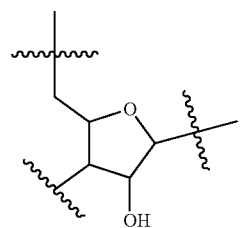

Ribonucleotide: As used herein, the term "ribonucleotide" refers to a natural nucleotide (as defined herein) or a modified nucleotide (as defined herein) which has a hydroxyl group at the 2'-position of the sugar moiety.

Sense strand: A double-stranded nucleic acid inhibitor molecule comprises two oligonucleotide strands: an antisense strand and a sense strand. The sense strand or a region thereof is partially, substantially or fully complementary to the antisense strand of the double-stranded nucleic acid inhibitor molecule or a region thereof. In certain embodiments, the sense strand may also contain nucleotides that are non-complementary to the antisense strand. The non-complementary nucleotides may be on either side of the complementary sequence or may be on both sides of the complementary sequence. In certain embodiments, where the sense strand or a region thereof is partially or substantially complementary to the antisense strand or a region thereof, the non-complementary nucleotides may be located between one or more regions of complementarity (e.g., one or more mismatches). The sense strand is also called the passenger strand.

Subject: As used herein, the term "subject" means any mammal, including mice, rabbits, and humans. In one embodiment, the subject is a human. The terms "individual" or "patient" are intended to be interchangeable with "subject."

Substituent or substituted: The terms "substituent" or "substituted" as used herein refer to the replacement of hydrogen radicals in a given structure with the radical of a substituent. When more than one position in any given structure may be substituted with more than one substituent, the substituent may be either the same or different at every position unless otherwise indicated. As used herein, the term "substituted" is contemplated to include all permissible substituents that are compatible with organic compounds. The permissible substituents include acyclic and cyclic, branched and unbranched, carbocyclic and heterocyclic, aromatic and nonaromatic substituents of organic compounds. This disclosure is not intended to be limited in any manner by the permissible substituents of organic compounds.

Substituted sugar moiety. As used herein, a "substituted sugar moiety" includes furanosyls comprising one or more modifications. Typically, the modifications occur at the 2'-, 3'-, 4'-, or 5'-carbon position of the sugar. In certain embodiments, the substituted sugar moiety is a bicyclic sugar moiety comprising a bridge that connects the 2'-carbon with the 4-carbon of the furanosyl.

Sugar analog: As used herein, the term "sugar analog" refers to a structure that does not comprise a furanosyl and that can replace the naturally occurring sugar moiety of a nucleotide, such that the resulting nucleotide is capable of (1) incorporation into an oligonucleotide and (2) hybridization to a complementary nucleotide. Such structures typically include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties. Sugar analogs also include more complex sugar replacements (e.g., the non-ring systems of peptide nucleic acid). Sugar analogs include without limitation morpholinos, cyclohexenyls and cyclohexitols.

Sugar moiety: As used herein, the term "sugar moiety" refers to a natural sugar moiety or a modified sugar moiety of a nucleotide or nucleoside.

Target site: As used herein, the term "target site" "target sequence," "target nucleic acid", "target region," "target gene" are used interchangeably and refer to a RNA or DNA sequence that is "targeted," e.g., for cleavage mediated by an RNAi inhibitor molecule that contains a sequence within its guide/antisense region that is partially, substantially, or perfectly or sufficiently complementary to that target sequence.

Tetraloop: As used herein, the term "tetraloop" refers to a loop (a single stranded region) that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the nucleotides in a tetraloop include but are not limited to non-Watson-Crick base pairing, stacking interactions, hydrogen bonding, and contact interactions (Cheong et al., NATURE 1990; 346(6285):680-2; Heus and Pardi, SCIENCE 1991; 253(5016):191-4). A tetraloop confers an increase in the melting temperature (Tm) of an adjacent duplex that is higher than expected from a simple model loop sequence consisting of random bases. For example, a tetraloop can confer a melting temperature of at least 50° C., at least 55° C., at least 56° C., at least 58° C., at least 60° C., at least 65° C. or at least 75° C. in 10 mM NaHPO4 to a hairpin comprising a duplex of at least 2 base pairs in length. A tetraloop may contain ribonucleotides, deoxyribonucleotides, modified nucleotides, and combinations thereof. In certain embodiments, a tetraloop consists of four nucleotides. In certain embodiments, a tetraloop consists of five nucleotides.

Examples of RNA tetraloops include the UNCG family of tetraloops (e.g., UUCG), the GNRA family of tetraloops (e.g., GAAA), and the CUYG family of tetraloops, including the CUUG tetraloop. (Woese et al., PNAS, 1990, 87(21): 8467-71; Antao et al., Nucleic Acids Res., 1991, 19(21): 5901-5). Other examples of RNA tetraloops include the GANC, A/UGNN, and UUUM tetraloop families (Thapar et al., WILEY INTERDISCIP. REV RNA, 2014, 5(1):1-28) and the GGUG, RNYA, and AGNN tetraloop families (Bottaro et al., BIOPHYS J., 2017, 113:257-67). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). (Nakano et al. Biochemistry, 2002, 41(48): 14281-14292. Shinji et al., Nippon Kagakkai Koen Yokoshu, 2000, 78(2):731).

$T_m$-Increasing Nucleotide: As used herein, the term "$T_m$-increasing nucleotide" refers to a nucleotide that increases the melting temperature ($T_m$) of an oligonucleotide duplex as compared to the oligonucleotide duplex without the $T_m$-increasing nucleotide. $T_m$-increasing nucleotides include, but are not limited to, bicyclic nucleotides, tricyclic nucleotides, a G-clamp and analogues thereof, and hexitol nucleotides. Certain modified nucleotides having a modified sugar moiety or a modified nucleobase can also be used to increase the $T_m$ of an oligonucleotide duplex. As used herein, the term "$T_m$-increasing nucleotide" specifically excludes nucleotides modified at the 2'-position of the sugar moiety with 2'-OMe or 2'-F.

Triloop: As used herein, the term "triloop" refers to a loop (a single stranded region) that forms a stable secondary structure that contributes to the stability of an adjacent Watson-Crick hybridized nucleotides and consists of three nucleotides. Without being limited to theory, a triloop may be stabilized by non-Watson-Crick base pairing of nucleotides within the triloop and base-stacking interactions. (Yoshizawa et al., Biochemistry 1997; 36, 4761-4767). A triloop can also confer an increase in the melting temperature (Tm) of an adjacent duplex that is higher than expected from a simple model loop sequence consisting of random bases. A triloop may contain ribonucleotides, deoxyribonucleotides, modified nucleotides, and combinations thereof. Examples of triloops include the GNA family of triloops (e.g., GAA, GTA, GCA, and GGA). (Yoshizawa 1997).

Therapeutically effective amount: As used herein, a "therapeutically effective amount" or "pharmacologically effective amount" refers to that amount of a double-stranded nucleic acid inhibitor molecule effective to produce the intended pharmacological, therapeutic or preventive result.

Universal nucleobase: As used herein, a "universal nucleobase" refers to a base that can pair with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. The universal nucleobase may base pair by forming hydrogen bonds via Watson-Crick or non-Watson-Crick interactions (e.g., Hoogsteen interactions). Representative universal nucleobases include inosine and its derivatives.

DETAILED DESCRIPTION

This application provides double-stranded nucleic acid inhibitor molecules having a sense strand with a stem loop structure and an antisense strand, where the stem portion of the stem loop structure contains at least one $T_m$-increasing nucleotide. As shown in the examples, incorporating $T_m$-increasing nucleotides, such as bicyclic nucleotides, into the stem portion of the stem loop structure imparts increased stability to the double-stranded nucleic acid inhibitor molecule, as evidenced, in part, by enhanced duration of in vivo target mRNA knock down. It also permits the use of shorter sense strands, as incorporating bicyclic nucleotides into the stem portion of the stem loop structure allows the stem portion to be shortened without reducing potency. The use of shorter sense strands confers advantages in the manufacturing process, reducing both time and cost. Reducing the length of the stem also confers advantages in dosing because it is possible to administer more of double-stranded nucleic acid inhibitor molecule on a molar basis due to its reduced molecular weight.

Also provided are methods of using the $T_m$-increasing nucleotide-modified, stem loop nucleic acid inhibitor molecules and compositions comprising the same to reduce the level or expression of a target gene in vitro or in vivo, including methods and compositions for treating diseases.

$T_m$-Increasing Nucleotides

The nucleic acid inhibitor molecules disclosed herein contain a sense strand and an antisense strand and at least one $T_m$-increasing nucleotide in the stem portion (D2) of a stem loop structure that is present in the sense strand. See e.g., FIG. 10D. $T_m$-increasing nucleotides include, but are not limited to, bicyclic nucleotides, tricyclic nucleotides, a G-clamp and analogues thereof, hexitol nucleotides, or a modified nucleotide.

Bicyclic Nucleotides

Bicyclic nucleotides typically have a sugar moiety with a 4 to 7 membered ring (including but not limited to a furanosyl) comprising a bridge connecting two atoms of the 4 to 7 membered ring to form a second ring, resulting in a bicyclic structure. Such bicyclic nucleotides have various names including BNA's and LNA's for bicyclic nucleic acids and locked nucleic acids, respectively. The synthesis of bicyclic nucleotides and their incorporation into nucleic acid compounds has also been reported in the literature, including, for example, Singh et al., CHEM. COMMUN., 1998, 4, 455-456; Koshkin et al., TETRAHEDRON, 1998, 54, 3607-3630; Wahlestedt et al., PROC. NATL. ACAD. SCI. U.S.A., 2000, 97, 5633-5638; Kumar et al., BIOORG. MED. CHEM. LETT., 1998, 8, 2219-2222; Singh et al., J. ORG. CHEM., 1998, 63, 10035-10039; U.S. Pat. Nos. 7,427,672, 7,053,207, 6,794,499, 6,770,748, 6,268,490 and 6,794,499; and published U.S. applications 20040219565, 20040014959, 20030207841, 20040192918, 20030224377, 20040143114 and 20030082807; each of which is incorporated by reference herein, in its entirety.

The $T_m$-increasing nucleotide can be a bicyclic nucleotide that comprises a bicyclic sugar moiety. In certain embodiments, the bicyclic sugar moiety comprises a first ring of 4 to 7 members and a bridge forming a North-type sugar confirmation that connects any two atoms of the first ring of the sugar moiety to form a second ring. In certain embodiments, the bridge connects the 2'-carbon and the 4'-carbon of the first ring to form a second ring.

Typically, the bridge contains 2 to 8 atoms. In certain embodiments, the bridge contains 3 atoms. In certain embodiments, the bridge contains 4 atoms. In certain embodiments, the bridge contains 5 atoms. In certain embodiments, the bridge contains 6 atoms. In certain embodiments, the bridge contains 7 atoms. In certain embodiments, the bridge contains 8 atoms. In certain embodiments, the bridge contains more than 8 atoms.

In certain embodiments, the bicyclic sugar moiety is a substituted furanosyl comprising a bridge that connects the 2'-carbon and the 4'-carbon of the furanosyl to form the second ring. In certain embodiments, the bicyclic nucleotide has the structure of Formula I:

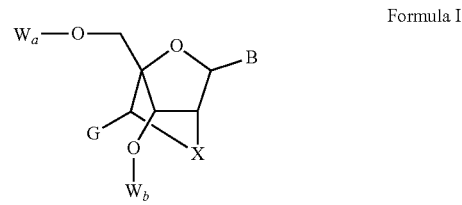

Formula I wherein B is a nucleobase;

wherein G is H, OH, NH$_2$, C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol, or substituted thio;

wherein X is O, S, or NR$_1$, wherein R$_1$ is H, C$_1$-C$_6$ alkyl, C$_1$-C$_6$ alkoxy, benzene or pyrene; and wherein W$_a$ and W$_b$ are each independently, H, OH, a hydroxyl protecting group, a phosphorous moiety, or an internucleotide linking group attaching the nucleotide represented by Formula I to another nucleotide or to an oligonucleotide and wherein at least one of W$_a$ or W$_b$ is an internucleotide linking group attaching the nucleotide represented by Formula I to an oligonucleotide.

In certain embodiments of Formula I, G is H and X is NR$_1$, wherein R$_1$ is benzene or pyrene. In certain embodiments, of Formula I, G is H and X is S.

In certain embodiments of Formula I, G is H and X is O:

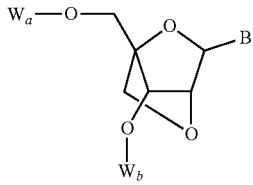

Formula Ia

In certain embodiments of Formula I, G is H and X is $NR_1$, wherein $R_1$ is H, $CH_3$, or $OCH_3$:

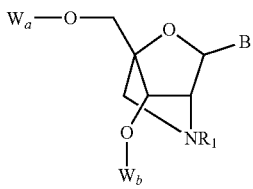

Formula Ib

In certain embodiments of Formula I, G is OH or $NH_2$ and X is O.

In certain embodiments of Formula I, G is OH and X is O:

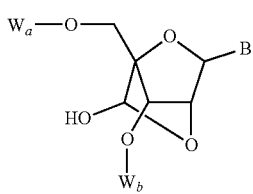

Formula Ic

In certain embodiments of Formula I, G is $NH_2$ and X is O:

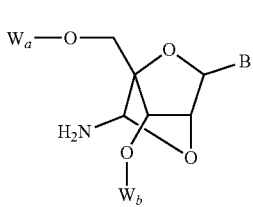

Formula Id

In certain embodiments, of Formula I, G is $CH_3$ or $CH_2OCH_3$ and X is O.

In certain embodiments, of Formula I, G is $CH_3$ and X is O:

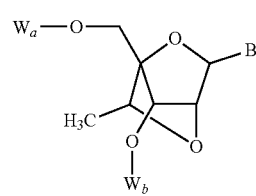

Formula Ie

In certain embodiments, of Formula I, G is $CH_2OCH_3$ and X is O:

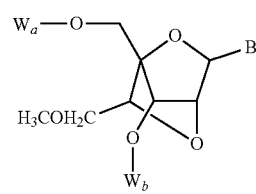

Formula If

In certain embodiments, the bicyclic nucleotide has the structure of Formula II:

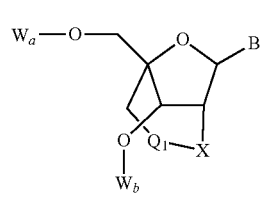

Formula II wherein B is a nucleobase;
wherein $Q_1$ is $CH_2$ or O;
wherein X is $CH_2$, O, S, or $NR_1$, wherein $R_1$ is H, $C_1$-$C_6$ alkyl, $C_1$-$C_6$ alkoxy, benzene or pyrene;
wherein if $Q_1$ is O, X is $CH_2$;
wherein if $Q_1$ is $CH_2$, X is $CH_2$, O, S, or $NR_1$, wherein $R_1$ is H, $C_1$-$C_6$ alkyl, $C_1$-$C_6$ alkoxy, benzene or pyrene;
wherein $W_a$ and $W_b$ are each independently, H, OH, a hydroxyl protecting group, a phosphorous moiety, or an internucleotide linking group attaching the nucleotide represented by Formula II to another nucleotide or to an oligonucleotide and wherein at least one of $W_a$ or $W_b$ is an internucleotide linking group attaching the nucleotide represented by Formula II to an oligonucleotide.

In certain embodiments of Formula II, $Q_1$ is O and X is $CH_2$:

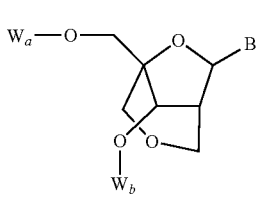

Formula IIa

In certain embodiments of Formula II, $Q_1$ is $CH_2$ and X is O:

Formula IIb

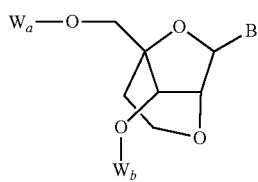

In certain embodiments of Formula II, $Q_1$ is $CH_2$ and X is $NR_1$, wherein $R_1$ is H, $CH_3$ or $OCH_3$:

Formula IIc

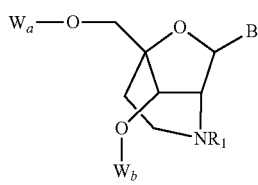

In certain embodiments of Formula II, $Q_1$ is $CH_2$ and X is NH:

Formula IId

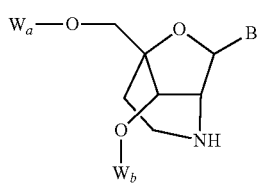

In certain embodiments, the bicyclic nucleotide has the structure of Formula III:

Formula III

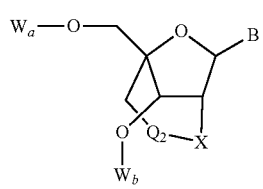

wherein B is a nucleobase;
wherein $Q_2$ is O or $NR_1$, wherein $R_1$ is H, $C_1$-$C_6$ alkyl, $C_1$-$C_6$ alkoxy, benzene or pyrene;
wherein X is $CH_2$, O, S, or $NR_1$, wherein $R_1$ is H, $C_1$-$C_6$ alkyl, $C_1$-$C_6$ alkoxy, benzene or pyrene;
wherein if $Q_2$ is O, X is $NR_1$,
wherein if $Q_2$ is $NR_1$, X is O or S;
wherein $W_a$ and $W_b$ are each independently, H, OH, a hydroxyl protecting group, a phosphorous moiety, or an internucleotide linking group attaching the nucleotide represented by Formula III to another nucleotide or to an oligonucleotide and wherein at least one of $W_a$ or $W_b$ is an internucleotide linking group attaching the nucleotide represented by Formula III to an oligonucleotide.

In certain embodiments of Formula III, $Q_2$ is O and X is $NR_1$. In certain embodiments of Formula III, $Q_2$ is O and X is $NR_1$, wherein $R_1$ is $C_1$-$C_6$ alkyl. In certain embodiments of Formula III, $Q_2$ is O and X is $NR_1$ and $R_1$ is H or $CH_3$.

In certain embodiments of Formula III, $Q_2$ is O and X is $NR_1$ and $R_1$ is $CH_3$:

Formula IIIa

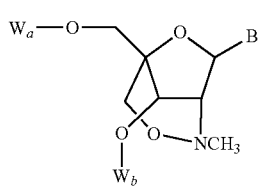

In certain embodiments of Formula III, $Q_2$ is $NR_1$ and X is O. In certain embodiments of Formula III, $Q_2$ is $NR_1$, wherein $R_1$ is $C_1$-$C_6$ alkyl and X is O.
In certain embodiments of Formula III, $Q_2$ is $NCH_3$ and X is O:

Formula IIIb

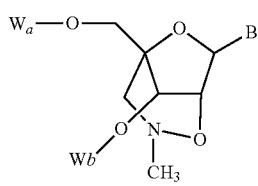

In certain embodiments, the bicyclic nucleotide has the structure of Formula IV:

Formula IV

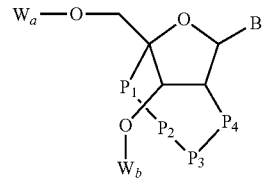

wherein B is a nucleobase;
wherein $P_1$ and $P_3$ are $CH_2$, $P_2$ is $CH_2$ or O and $P_4$ is O; and
wherein $W_a$ and $W_b$ are each independently, H, OH, a hydroxyl protecting group, a phosphorous moiety, or an internucleotide linking group attaching the nucleotide represented by Formula IV to another nucleotide or to an oligonucleotide and wherein at least one of $W_a$ or $W_b$ is an internucleotide linking group attaching the nucleotide represented by Formula IV to an oligonucleotide.

In certain embodiments of Formula IV, $P_1$, $P_2$, and $P_3$ are $CH_2$, and $P_4$ is O:

Formula IVa

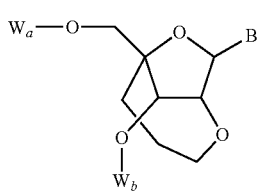

In certain embodiments of Formula IV, $P_1$ and $P_3$ are $CH_2$, $P_2$ is O and $P_4$ is O:

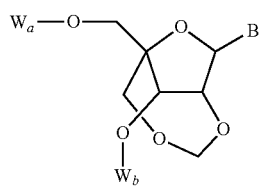

Formula IVb

In certain embodiments, the bicyclic nucleotide has the structure of Formula Va or Vb:

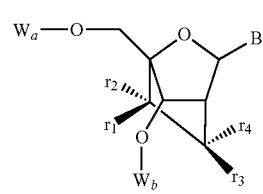

Formula Va

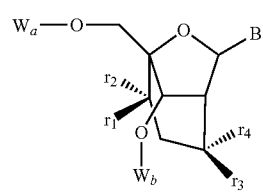

Formula Vb wherein B is a nucleobase;

wherein r1, r2, r3, and r4 are each independently H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl; substituted $C_2$-$C_{12}$ alkynyl; $C_1$-$C_{12}$ alkoxy; substituted $C_1$-$C_{12}$ alkoxy, $OT_1$, $ST_1$, $SOT_1$, $SO_2T_1$, $NT_1T_2$, N3, CN, C(=O)$OT_1$, C(=O)$NT_1T_2$, C(=O)$T_1$, O—C(=O)$NT_1T_2$, N(H)C(=NH)$NT_1T_2$, N(H)C(=O)$NT_1T_2$ or N(H)C(=S)$NT_1T_2$, wherein each of T1 and T2 is independently H, $C_1$-$C_6$ alkyl, or substituted $C_1$-$C_{16}$ alkyl; or r1 and r2 or r3 and r4 together are =C(r5)(r6), wherein r5 and r6 are each independently H, halogen, $C_1$-$C_{12}$ alkyl, or substituted $C_1$-$C_{12}$ alkyl; and wherein $W_a$ and $W_b$ are each independently, H, OH, a hydroxyl protecting group, a phosphorous moiety, or an internucleotide linking group attaching the nucleotide represented by Formula V to another nucleotide or to an oligonucleotide and wherein at least one of $W_a$ or $W_b$ is an internucleotide linking group attaching the nucleotide represented by Formula V to an oligonucleotide.

In certain embodiments, the bicyclic sugar moiety is a substituted furanosyl comprising a bridge that connects the 2'-carbon and the 4'-carbon of the furanosyl to form the second ring, wherein the bridge that connects the 2'-carbon and the 4'-carbon of the furanosyl includes, but is not limited to:

a) 4'-$CH_2$—O—N(R)-2' and 4'-$CH_2$—N(R)—O-2', wherein R is H, $C_1$-$C_{12}$ alkyl, or a protecting group, including, for example, 4'-$CH_2$—NH—O-2' (also known as $BNA^{NC}$), 4'-$CH_2$—N($CH_3$)—O-2' (also known as $BNA^{NC}$[NMe]), (as described in U.S. Pat. No. 7,427,672, which is hereby incorporated by reference in its entirety);

b) 4'-$CH_2$-2'; 4'-$(CH_2)_2$-2'; 4'-$(CH_2)_3$-2'; 4'-$(CH_2)$—O-2' (also known as LNA); 4'-$(CH_2)$—S-2'; 4'-$(CH_2)_2$—O-2' (also known as ENA); 4'-$CH(CH_3)$—O-2' (also known as cEt); and 4'-$CH(CH_2OCH_3)$—O-2' (also known as cMOE), and analogs thereof (as described in U.S. Pat. No. 7,399,845, which is hereby incorporated by reference in its entirety);

c) 4'-$C(CH_3)(CH_3)$—O-2' and analogs thereof (as described in U.S. Pat. No. 8,278,283, which is hereby incorporated by reference in its entirety);

d) 4'-$CH_2$—N(OCH_3)-2' and analogs thereof (as described in U.S. Pat. No. 8,278,425, which is hereby incorporated by reference in its entirety);

e) 4'-$CH_2$—O—N($CH_3$)-2' and analogs thereof (as described in U.S. Patent Publication No. 2004/0171570, which is hereby incorporated by reference in its entirety);

f) 4'-$CH_2$—C(H)($CH_3$)-2' and analogs thereof (as described in Chattopadhyaya et al., J. Org. Chem., 2009, 74, 118-34, which is hereby incorporated by reference in its entirety); and g) 4'-$CH_2$—C(=$CH_2$)-2' and analogs thereof as described in U.S. Pat. No. 8,278,426, which is hereby incorporated by reference in its entirety).

In certain embodiments, the bicyclic nucleotide (BN) is one or more of the following: (a) methyleneoxy BN, (b) ethyleneoxy BN, (c) aminooxy BN; (d) oxyamino BN, (e) methyl(methyleneoxy) BN (also known as constrained ethyl or cET), (f) methylene-thio BN, (g) methylene amino BN, (h) methyl carbocyclic BN, and (i) propylene carbocyclic BN, as shown below.

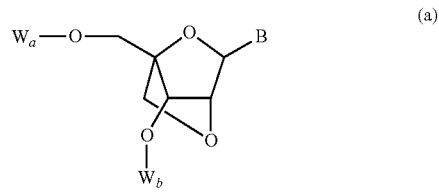

(a)

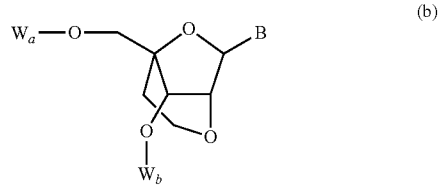

(b)

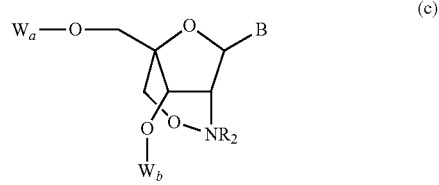

(c)

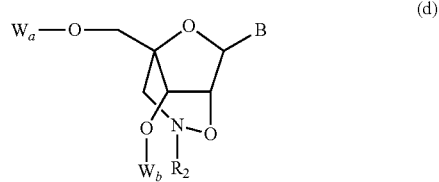

(d)

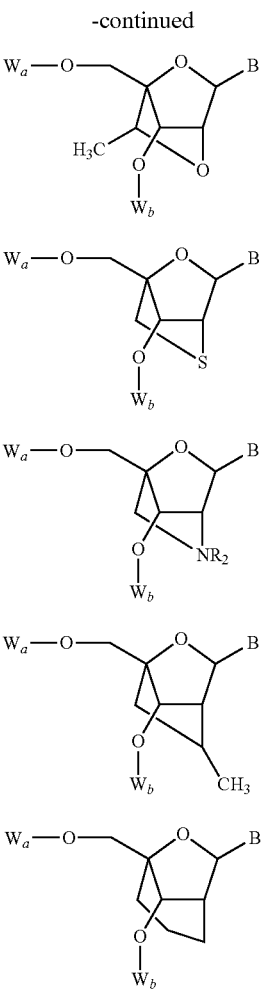

In the bicyclic nucleotides of (a) to (i) above, B is a nucleobase, $R_2$ is H or $CH_3$ and $W_a$ and $W_b$ are each independently, H, OH, a hydroxyl protecting group, a phosphorous moiety, or an internucleotide linking group attaching the bicyclic nucleotide to another nucleotide or to an oligonucleotide and wherein at least one of $W_a$ or $W_b$ is an internucleotide linking group attaching the bicyclic nucleotide to an oligonucleotide.

In one embodiment of the oxyamino BN (d), $R_2$ is $CH_3$, as follows (also known as $BNA^{NC}$[NMe]):

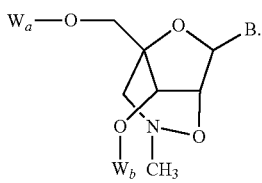

In certain embodiments, bicyclic sugar moieties and bicyclic nucleotides incorporating such bicyclic sugar moieties are further defined by isomeric configuration. In certain embodiments, the bicyclic sugar moiety or nucleotide is in the α-L configuration. In certain embodiments, the bicyclic sugar moiety or nucleotide is in the β-D configuration. For example, in certain embodiments, the bicyclic sugar moiety or nucleotide comprises a 2'O,4'-C-methylene bridge (2'-O—$CH_2$-4') in the α-L configuration (α-L LNA). In certain embodiments, the bicyclic sugar moiety or nucleotide is in the R configuration. In certain embodiments, the bicyclic sugar moiety or nucleotide is in the S configuration. For example, in certain embodiments, the bicyclic sugar moiety or nucleotide comprises a 4'-CH($CH_3$)—O-2' bridge (i.e., cEt) in the S-configuration.

Tricyclic Nucleotides

In certain embodiments, the $T_m$-increasing nucleotide can be a tricyclic nucleotide. The synthesis of tricyclic nucleotides and their incorporation into nucleic acid compounds has also been reported in the literature, including, for example, Steffens et al., J. AM. CHEM. SOC. 1997; 119:11548-11549; Steffens et al., J. ORG. CHEM. 1999; 121(14):3249-3255; Renneberg et al., J. AM. CHEM. SOC. 2002; 124:5993-6002; Ittig et al., NUCLEIC ACIDS RES. 2004; 32(1):346-353; Scheidegger et al., Chemistry 2006; 12:8014-8023; Ivanova et al., OLIGONUCLEOTIDES 2007; 17:54-65; each of which is each hereby incorporated by reference in its entirety.

In certain embodiments, the tricyclic nucleotide is a tricyclo nucleotide (also called tricyclo DNA) in which the 3'-carbon and 5'-carbon centers are connected by an ethylene that is fused to a cyclopropane ring, as discussed for example in Leumann C J, Bioorg. Med. Chem. 2002; 10:841-854 and published U.S. Applications 2015/0259681 and 2018/0162897, which are each hereby incorporated by reference. In certain embodiments, the tricyclic nucleotide comprises a substituted furanosyl ring comprising a bridge that connects the 2'-carbon and the 4'-carbon of the furanosyl to form a second ring, and a third fused ring resulting from a group connecting the 5'-carbon to the methylene group of the bridge that connects the 2'-carbon and the 4'-carbon of the furanosyl, as discussed, for example, in published U.S. Application 2015/0112055, which is hereby incorporated by reference.

Other $T_m$-Increasing Nucleotides

In addition to bicyclic and tricyclic nucleotides, other $T_m$-increasing nucleotides can be used in the nucleic acid inhibitor molecules described herein. For example, in certain embodiments, the $T_m$-increasing nucleotide is a G-clamp, guanidine G-clamp or analogue thereof (Wilds et al., Chem, 2002; 114:123 and Wilds et al., Chim Acta 2003; 114:123), a hexitol nucleotide (Herdewijn, Chem. Biodiversity 2010; 7:1-59), or a modified nucleotide. The modified nucleotide can have a modified nucleobase, as described herein, including for example, 5-bromo-uracil, 5-iodo-uracil, 5-propynyl-modified pyrimidines, or 2-amino adenine (also called 2,6-diaminopurine) (Deleavey et al., Chem. & Biol. 2012; 19:937-54) or 2-thio uridine, 5 Me-thio uridine, and pseudo uridine. The modified nucleotide can also have a modified sugar moiety, as described for example, in U.S. Pat. No. 8,975,389, which is hereby incorporated by reference, or as described herein, except that the $T_m$-increasing nucleotide is not modified at the 2'-carbon of the sugar moiety with a 2'-F or a 2'-OMe.

In certain embodiments, the $T_m$-increasing nucleotide is a bicyclic nucleotide. In certain embodiments, the $T_m$-increasing nucleotide is a tricyclic nucleotide. In certain embodiments, the $T_m$-increasing nucleotide a G-clamp, guanidine G-clamp or analogue thereof. In certain embodiments, the $T_m$-increasing nucleotide is a hexitol nucleotide. In certain embodiments, the $T_m$-increasing nucleotide is a bicyclic or tricyclic nucleotide. In certain embodiments, the $T_m$-increasing nucleotide is a bicyclic nucleotide, a tricyclic nucleotide, or a G-clamp, guanidine G-clamp or analogue thereof. In certain embodiments, the $T_m$-increasing nucleotide is a bicyclic nucleotide, a tricyclic nucleotide, a G-clamp, guanidine G-clamp or analogue thereof, or a hexitol nucleotide.

In certain embodiments, the $T_m$-increasing nucleotide increases the $T_m$ of the second duplex (D2) of the nucleic acid inhibitor molecule by at least 2° C. per incorporation. In certain embodiments, the $T_m$-increasing nucleotide increases the $T_m$ of D2 by at least 3° C. per incorporation. In certain embodiments, the $T_m$-increasing nucleotide increases the $T_m$ of D2 by at least 4° C. per incorporation. In certain embodiments, the $T_m$-increasing nucleotide increases the $T_m$ of D2 by at least 5° C. per incorporation.

$T_m$-Increasing Nucleotide-Modified, Nucleic Acid Inhibitor Molecules

This application discloses double-stranded nucleic acid inhibitor molecules having a sense strand with a stem loop structure and an antisense strand, wherein the stem portion of the stem loop structure contains at least one $T_m$-increasing nucleotide and wherein the sense strand and antisense strands are separate strands that each have a 5'- and 3'-end and, therefore, do not form a contiguous oligonucleotide. A typical stem/loop-containing double-stranded nucleic acid inhibitor molecule is shown in FIG. 10A with the sense strand ("S") and antisense strand ("AS") highlighted.

The sense strand can be further divided into a first region (R1) that forms a first duplex (D1) with the antisense strand (AS) and a second region (R2) that includes a loop (L) that joins a first subregion (51) with a second subregion (S2), as shown in FIGS. 10B and 10C. 51 and S2 are sufficiently complementary to each other to form a second duplex (D2), also referred to as the stem or stem duplex. See e.g. FIGS. 10C and 10D. In certain embodiments, the loop is a tetraloop. The second duplex (D2) contains one or more $T_m$-increasing nucleotides. Typically, the $T_m$-increasing nucleotide is a bicyclic nucleotide. However, in all the double-stranded nucleic acid inhibitor molecules described herein any $T_m$-increasing nucleotide, as defined herein, can be substituted for the bicyclic nucleotide. Typically, the double-stranded nucleic acid inhibitor molecule does not contain any $T_m$-increasing nucleotides (e.g., bicyclic nucleotides) outside of the second duplex (D2). In certain embodiments, the double-stranded nucleic acid molecule is a dsRNAi inhibitor molecule.

In certain embodiments of the double-stranded nucleic acid inhibitor molecule, the sense strand contains a stem duplex (D2) containing at least one $T_m$-increasing nucleotide (e.g., bicyclic nucleotide) and a loop (L) and is 20-66 or 21-66 nucleotides in length. In certain embodiments, the stem duplex is 1-6 base pairs in length. In certain embodiments, the stem duplex is 3-6 base pairs in length. In certain embodiments, the stem duplex is 1-3 base pairs in length. In certain embodiments, the antisense strand is 15-40 nucleotides in length. In certain embodiments, the loop is 3-20 nucleotides in length. In certain embodiments, the loop is 3-8 nucleotides in length. Typically, the loop is a tetraloop. However, in all the double-stranded nucleic acid inhibitor embodiments described herein, the tetraloop can be replaced with a triloop, such as a triloop having the nucleotide sequence GAA.

In certain embodiments, the sense strand contains a stem duplex (D2) and tetraloop (L) and is 20-66 nucleotides in length, and the antisense strand is 15-40 nucleotides in length. In certain embodiments, the sense strand is 24-54 nucleotides in length. In certain embodiments, the sense strand is 24-44 nucleotides in length. In certain embodiments, the sense strand is 24-38 nucleotides in length. In certain embodiments, the extended part of the sense strand that contains the stem duplex (D2) and tetraloop (L) is on 3'-end of the strand. In certain other embodiments, the extended part of the sense strand that contains the stem (D2) and tetraloop (L) is on 5'-end of the strand.

In certain embodiments, the double-stranded nucleic acid inhibitor molecule comprises a sense strand and an antisense strand, wherein the sense and antisense strands are separate strands and form a first duplex (D1) of 18-24 base pairs, wherein the sense strand comprises a second duplex (D2) and tetraloop (L) and is 24-36 nucleotides in length, and wherein the antisense strand is 20-24 nucleotides in length. In certain embodiments, the sense strand is 28-36, 28-35, or 28-34 nucleotides in length. In certain embodiments, the sense strand is 24-35 nucleotides in length. In certain embodiments, the sense strand is 24-34 nucleotides in length. In certain embodiments, the sense strand is 26-30 nucleotides in length. In certain embodiments, the sense strand is 30-32 nucleotides in length. In certain embodiments, the sense strand is 24 nucleotides in length. In certain embodiments, the sense strand is 26 nucleotides in length. In certain embodiments, the sense strand is 28 nucleotides in length. In certain embodiments, the sense strand is 30 nucleotides in length. In certain embodiments, the sense strand is 32 nucleotides in length. In certain embodiments, the sense strand is 34 nucleotides in length. In certain embodiments, the second duplex (D2) has a length of 1-5 base pairs. In certain embodiments, D2 has a length of 1 base pair. In certain embodiments, D2 has a length of 2 base pairs. In certain embodiments, D2 has a length of 3 base pairs. In certain embodiments, the antisense strand has a single-stranded overhang of 1, 2, 3, or 4 nucleotides at its 3'-end. Typically, the single-stranded overhang at the 3'-end of the antisense strand consists of 2 nucleotides.

In certain embodiments, the double-stranded nucleic acid inhibitor molecule comprises a sense strand and an antisense strand, wherein the sense and antisense strands are separate strands and form a first duplex (D1) of 19-21 base pairs, wherein the sense strand comprises a second duplex (D2) and tetraloop (L) and is 24-34 nucleotides in length, and wherein the antisense strand is 20-23 nucleotides in length. In certain embodiments, the sense strand is 28-34 nucleotides in length. In certain embodiments, the sense strand is 24-30 nucleotides in length and the second duplex (D2) has a length of 1-3 base pairs. In certain embodiments, D2 has a length of 1 base pair. In certain embodiments, D2 has a length of 2 base pairs. In certain embodiments, D2 has a length of 3 base pairs. In certain embodiments, the sense strand is 30-32 nucleotides in length and D2 has a length of 3-5 base pairs. In certain embodiments, D2 has a length of 3 base pairs.

In certain embodiments, the antisense strand has a single-stranded overhang of 1-6 nucleotides at its 3'-end. In certain embodiments, the antisense strand has a single-stranded overhang of 1, 2, 3, or 4 nucleotides at its 3'-end. Typically, the single-stranded overhang at the 3'-end of the antisense strand consists of 2 nucleotides.

In certain embodiments, the double-stranded nucleic acid inhibitor molecule comprises a sense strand and an antisense strand, wherein the sense and antisense strands are separate strands and form a first duplex (D1) of 19-21 base pairs, wherein the sense strand has a first region (R1) of 19-21 nucleotides and a second region (R2) of 6-16 nucleotides that comprises a tetraloop (L) that joins a first subregion (S1) to a second subregion (S2), wherein each of S1 and S2 is 1-6 nucleotides in length and are sufficiently complementary to each other to form a second duplex (D2), and wherein the antisense strand is 20-24 nucleotides in length. In certain embodiments, the antisense strand has a single-stranded overhang of two nucleotides at its 3'-end. In certain embodiments, R2 is 10-16 nucleotides in length. In certain embodiments, R2 is 6 nucleotides in length. In certain embodiments, R2 is 8 nucleotides in length. In certain embodiments, R2 is 10 nucleotides in length. In certain embodiments, each of S1 and S2 is 1-5 nucleotides in length. In certain embodiments, each of S1 and S2 is 1-3 nucleotides in length. In certain embodiments, each of S1 and S2 is 3-5 nucleotides in length. In certain embodiments, each of S1 and S2 is 1 nucleotide in length. In certain embodiments, each of S1 and S2 is 2 nucleotides in length. In certain embodiments, each of S1 and S2 is 3 nucleotides in length.

In certain embodiments, the double-stranded nucleic acid inhibitor molecule comprises a sense strand and an antisense strand, wherein the sense and antisense strands are separate strands and form a first duplex (D1) of 20 base pairs, wherein the sense strand has a first region (R1) of 20 nucleotides and a second region (R2) of 10 nucleotides that comprises a tetraloop (L) that joins a first subregion (S1) to a second subregion (S2), wherein each of S1 and S2 is 3 nucleotides in length and form a second duplex (D2) of three base pairs, and wherein the antisense strand is 22 nucleotides in length and has a single-stranded overhang of two nucleotides at its 3'-end. In certain embodiments, each nucleotide in the second duplex (D2) is a bicyclic nucleotide and the double-stranded nucleic acid inhibitor molecule does not contain any bicyclic nucleotides outside of the second duplex (D2). In certain embodiments, D2 contains 4 bicyclic nucleotides that form 2 base pairs. In certain embodiments, D2 contains 2 bicyclic nucleotides that form 1 base pair. In certain embodiments, D2 contains 3 unpaired bicyclic nucleotides. In certain embodiments, D2 contains 2 unpaired bicyclic nucleotides. In certain embodiments, D2 contains 1 bicyclic nucleotide. As described elsewhere, in each of these embodiments, the bicyclic nucleotide can be replaced by a different $T_m$-increasing nucleotide.

In certain embodiments, the double-stranded nucleic acid inhibitor molecule comprises a sense strand and an antisense strand, wherein the sense and antisense strands are separate strands and form a first duplex (D1) of 20 base pairs, wherein the sense strand has a first region (R1) of 20 nucleotides and a second region (R2) of 10 nucleotides that comprises a tetraloop (L) that joins a first subregion (S1) to a second subregion (S2), wherein each of S1 and S2 is 2 nucleotides in length and form a second duplex (D2) of two base pairs, and wherein the antisense strand is 22 nucleotides in length and has a single-stranded overhang of two nucleotides at its 3'-end. In certain embodiments, each nucleotide in the second duplex (D2) is a bicyclic nucleotide and the double-stranded nucleic acid inhibitor molecule does not contain any bicyclic nucleotides outside of the second duplex (D2). In certain embodiments, D2 contains 2 bicyclic nucleotides that form 1 base pair. In certain embodiments, D2 contains 2 unpaired bicyclic nucleotides. In certain embodiments, D2 contains 1 bicyclic nucleotide. As described elsewhere, in each of these embodiments, the bicyclic nucleotide can be replaced by a different $T_m$-increasing nucleotide.

In certain embodiments, the double-stranded nucleic acid inhibitor molecule comprises a sense strand and an antisense strand, wherein the sense and antisense strands are separate strands and form a first duplex (D1) of 20 base pairs, wherein the sense strand has a first region (R1) of 20 nucleotides and a second region (R2) of 10 nucleotides that comprises a tetraloop (L) that joins a first subregion (S1) to a second subregion (S2), wherein each of S1 and S2 is 1 nucleotide in length and form a second duplex (D2) of one base pair, and wherein the antisense strand is 22 nucleotides in length and has a single-stranded overhang of two nucleotides at its 3'-end. In certain embodiments, each nucleotide in the second duplex (D2) is a bicyclic nucleotide (or a $T_m$-increasing nucleotide other than a bicyclic nucleotide) and the double-stranded nucleic acid inhibitor molecule does not contain any bicyclic nucleotides (or $T_m$-increasing nucleotides other than a bicyclic nucleotide) outside of the second duplex (D2). In certain embodiments, the tetraloop has one of the following sequences: UNCG (e.g., UUCG, UCCG, UACG, or UGCG), GNRA (e.g., GAAA, GGAA, GAGA, GCAA, or GUAA), CUYG (e.g., CUUG), GANC, A/UGNN (e.g., UGAA), and UUUM, GGUG, RNYA (e.g., AACA), and AGNN (e.g., AGUA, AGAA, or AGGG), GGAG, UUUG, CAAC, CUUGU, GACAA, or GAAGA, where N is any nucleobase, R is a purine, Y is a pyrimidine, and M is A or C. In certain embodiments, the tetraloop is an RNA tetraloop selected from UNCG, GNRA, or CUUG. In certain embodiments, the tetraloop has the sequence GNRA. In certain embodiments, the tetraloop has the sequence GAAA. In certain embodiments, the tetraloop is a DNA tetraloop selected from d(GNAB), d(CNNG), or d(TNCG).

In certain embodiments of the double-stranded nucleic acid inhibitor molecule described herein, the second duplex (D2) has a length of 1-5 base pairs. In certain embodiments, D2 has a length of 1-3 base pairs. In certain embodiments, D2 has a length of 1-2 base pairs. In certain embodiments, D2 has a length of 3-4 base pairs. In certain embodiments, D2 has a length of 3-5 base pairs. In certain embodiments, D2 has a length of 1 base pair. In certain embodiments, D2 has a length of 2 base pairs. In certain embodiments, D2 has a length of 3 base pairs.

In certain embodiments of the double-stranded nucleic acid inhibitor molecule described herein, the second duplex (D2) contains 2-12 bicyclic nucleotides and has a length of 3-6 base pairs. In certain embodiments, D2 contains 1-6 or 2-6 bicyclic nucleotides and has a length of 1-3 base pairs. In certain embodiments, D2 contains 1-10 or 2-10 bicyclic nucleotides and has a length of 3-5 base pairs. In certain embodiments, D2 contains 1-8 or 2-8 bicyclic nucleotides and has a length of 3-4 base pairs. In certain embodiments, D2 contains 6 bicyclic nucleotides and has a length of 3 base pairs. In certain embodiments, D2 contains 4 bicyclic nucleotides and has a length of 2 base pairs. In certain embodiments, D2 contains 2 bicyclic nucleotides and has a length of 1 base pair. In certain embodiments, D2 contains 3 unpaired bicyclic nucleotides. In certain embodiments, D2 contains 2 unpaired bicyclic nucleotides. In certain embodiments, D2 contains 1 unpaired bicyclic nucleotide. In certain embodiments, each nucleotide in D2 is a bicyclic nucleotide. As described elsewhere, in each of these embodiments, the bicyclic nucleotide can be replaced by a different $T_m$-increasing nucleotide.

In certain embodiments, the double-stranded nucleic acid inhibitor molecule does not contain any bicyclic nucleotides in the first region of the sense strand (R1) or the antisense strand. In certain embodiments, the double-stranded nucleic acid inhibitor molecule does not contain any bicyclic nucleotides outside of the second duplex (D2). In certain embodiments, the double-stranded nucleic acid inhibitor molecule does not contain any $T_m$-increasing nucleotides in the first region of the sense strand (R1) or the antisense strand. In certain embodiments, the double-stranded nucleic acid inhibitor molecule does not contain any $T_m$-increasing nucleotides outside of the second duplex (D2).

The one or more bicyclic nucleotides in the second duplex (D2) of the double-stranded nucleic acid molecule can be any of the bicyclic nucleotides described herein or otherwise available in the art. In certain embodiments, the double-stranded nucleic acid molecule contains at least two bicyclic nucleotides in the second duplex (D2) and each bicyclic nucleotide in the second duplex is the same. In certain embodiments, the double-stranded nucleic acid molecule contains at least two different bicyclic nucleotides in the second duplex (D2). In certain embodiments, the double-stranded nucleic acid molecule contains at least two $T_m$-increasing nucleotides other than bicyclic nucleotides in the second duplex (D2) and each of the $T_m$-increasing nucleotides in the second duplex is the same. In certain embodiments, the double-stranded nucleic acid molecule contains at least two different $T_m$-increasing nucleotides (other than a bicyclic nucleotide) in the second duplex (D2).

In certain embodiments of the double-stranded nucleic acid inhibitor molecule described herein, the at least one bicyclic nucleotide in the second duplex (D2) comprises a bicyclic sugar moiety, wherein the bicyclic sugar moiety is a substituted furanosyl comprising a bridge that connects the 2'-carbon and the 4'-carbon of the furanosyl.

In certain embodiments of the double-stranded nucleic acid inhibitor molecule described herein, the at least one bicyclic nucleotide in the second duplex (D2) has the structure of Formula I, II, III, IV, Va, or Vb. In certain embodiments, the at least one bicyclic nucleotide in the second duplex (D2) has the structure of Formula I. In certain embodiments, the at least one bicyclic nucleotide in the second duplex (D2) has the structure of Formula II. In certain embodiments, the at least one bicyclic nucleotide in the second duplex (D2) has the structure of Formula III. In certain embodiments, the at least one bicyclic nucleotide in the second duplex (D2) has the structure of Formula IV. In certain embodiments, the at least one bicyclic nucleotide in the second duplex (D2) has the structure of Formula Va. In certain embodiments, the at least one bicyclic nucleotide in the second duplex (D2) has the structure of Formula Vb.

In certain embodiments, the at least one bicyclic nucleotide in the second duplex (D2) has the structure of one or more of Formula Ia, Ib, Ic, Id, Ie, or If. In certain embodiments, the at least one bicyclic nucleotide in the second duplex (D2) has the structure of one or more of Formula IIa, IIb, 11c, or IId. In certain embodiments, the at least one bicyclic nucleotide in the second duplex (D2) has the structure of Formula IIIa and/or IIIb. In certain embodiments, the at least one bicyclic nucleotide in the second duplex (D2) has the structure of Formula IVa and/or IVb.

In certain embodiments, the at least one bicyclic nucleotide (BN) in the second duplex (D2) is one or more of the following: (a) methyleneoxy BN, (b) ethyleneoxy BN, (c) aminooxy BN; (d) oxyamino BN, (e) methyl(methyleneoxy) BN (also known as constrained ethyl or cET), (f) methylenethio BN, (g) methylene amino BN, (h) methyl carbocyclic BN, and (i) propylene carbocyclic BN. In one embodiment, the at least one BN is (a) methyleneoxy BN or (d) oxyamino BN), wherein R2 is $CH_3$. In one embodiment, the at least one BN is the oxyamino BN (d), wherein R2 is $CH_3$.

Other Modifications

The double-stranded nucleic acid inhibitor molecules described herein can contain other nucleotide modifications in addition to the at least one $T_m$-increasing nucleotide in the second duplex (D2). Typically, multiple nucleotides of the double-stranded nucleic acid inhibitor molecule are modified to improve various characteristics of the molecule such as resistance to nucleases or lowered immunogenicity. See, e.g., Bramsen et al. (2009), NUCLEIC ACIDS RES., 37, 2867-2881. Many nucleotide modifications have been used in the oligonucleotide field, particularly for nucleic acid inhibitor molecules. Such modifications can be made on any part of the nucleotide, including the sugar moiety, the phosphodiester linkage, and the nucleobase. Typical examples of nucleotide modification include, but are not limited to, 2'-F, 2'-O-methyl ("2'-OMe" or "2'-$OCH_3$"), and 2'-O-methoxyethyl ("2'-MOE" or "2'-$OCH_2CH_2OCH_3$"). Modifications can also occur at other parts of the sugar moiety of the nucleotide, such as the 5'-carbon, as described herein.

In certain embodiments, the double-stranded nucleic acid inhibitor molecule can also include one or more modified nucleobases other than adenine, guanine, cytosine, thymine and uracil at the 1'-position, as known in the art and as described herein. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A typical example of a modified nucleobase is 5'-methylcytosine.

The natural occurring internucleotide linkage of RNA and DNA is a 3'- to 5'-phosphodiester linkage. Modified phosphodiester linkages include non-naturally occurring internucleotide linking groups, including internucleotide linkages that contain a phosphorous atom and internucleotide linkages that do not contain a phosphorous atom, as known in the art and as described herein. Typically, the double-stranded nucleic acid inhibitor molecule contains one or more phosphorous-containing internucleotide linking groups, as described herein. In other embodiments, one or more of the internucleotide linking groups of the double-stranded nucleic acid inhibitor molecule is a non-phosphorus containing linkage, as described herein. In certain embodiments, the double-stranded nucleic acid inhibitor molecule contains one or more phosphorous-containing internucleotide linking groups and one or more non-phosphorous containing internucleotide linking groups.

In certain embodiments, the double-stranded nucleic acid inhibitor molecule contains at least one phosphorothioate internucleotide linking group. In certain embodiments, the double-stranded nucleic acid inhibitor molecule contains less than 10, such as less than 5 phosphorothioate internucleotide linking groups. In certain embodiments, the double-stranded nucleic acid inhibitor molecule contains 4 phosphorothioate internucleotide linking groups.

A 5'-end of the sense and/or antisense strand of the double-stranded nucleic acid inhibitor molecule can include a natural substituent, such as a hydroxyl or a phosphate group. In certain embodiments, a hydroxyl group is attached to the 5'-terminal end of the sense and/or antisense strand of the double-stranded nucleic acid inhibitor molecule. In certain embodiments, a phosphate group is attached to the 5'-terminal end of the sense and/or antisense strand of the double-stranded nucleic acid inhibitor molecule. Typically, the phosphate is added to a monomer prior to oligonucleotide synthesis. In other embodiments, 5'-phosphorylation is accomplished naturally after a nucleic acid inhibitor molecule is introduced into the cytosol, for example, by a cytosolic Clp1 kinase. In some embodiments, the 5'-terminal phosphate is a phosphate group, such as 5'-monophosphate [$(HO)_2(O)P$—O-5'], 5'-diphosphate [$(HO)_2(O)P$—O—P(HO)(O)—O-5'] or a 5'-triphosphate[$(HO)_2(O)P$—O—(HO)(O)P—O—P(HO)(O)-0-5'].

The 5'-end of the sense and/or antisense strand of the double-stranded nucleic acid inhibitor molecule can also be modified. For example, in some embodiments, the 5'-end of the sense and/or antisense strand of the double-stranded nucleic acid inhibitor molecule is attached to a phosphoramidate [(HO)$_2$(O)P—NH-5', (HO)(NH$_2$)(O)P—O-5']. In certain embodiments, the 5'-terminal end of the sense and/or antisense strand of the double-stranded nucleic acid inhibitor molecule is attached to a phosphate mimic. Suitable phosphate mimics include 5'-phosphonates, such as 5'-methylenephosphonate (5'-MP), 5'-(E)-vinylphosphonate (5'-VP). Lima et al., Cell, 2012, 150-883-94; WO 2014/130607. Other suitable phosphate mimics include 4-phosphate analogs that are bound to the 4'-carbon of the sugar moiety (e.g., a ribose or deoxyribose or analog thereof) of the 5'-terminal nucleotide of an oligonucleotide as described in International Publication No. WO 2018/045317, which is hereby incorporated by reference in its entirety. For example, in some embodiments, the 5'-end of the sense and/or antisense strand of the double-stranded nucleic acid inhibitor molecule is attached to an oxymethylphosphonate, where the oxygen atom of the oxymethyl group is bound to the 4'-carbon of the sugar moiety or analog thereof. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, the double-stranded nucleic acid inhibitor molecule includes one or more deoxyribonucleotides. Typically, the double-stranded nucleic acid inhibitor molecules contain fewer than 5 deoxyribonucleotides. In certain embodiments, the double-stranded nucleic acid inhibitor molecules include one or more ribonucleotides. In certain embodiments, all the nucleotides of the double-stranded nucleic acid inhibitor molecule are ribonucleotides.

In certain embodiments, one or more nucleotides outside of the stem (second duplex or D2) of the double-stranded nucleic acid inhibitor molecule contain a sugar moiety have a modified ring structure, including but not limited to, the modified ring structure present in bicyclic or tricyclic nucleotides, as described herein, and Unlocked Nucleic Acids ("UNA") (see, e.g., Snead et al. (2013), MOLECULAR THERAPY—NUCLEIC ACIDS, 2, e103 (doi: 10.1038/mtna.2013.36)).

In certain embodiments one or two nucleotides of the double-stranded nucleic acid inhibitor molecule are reversibly modified with a glutathione-sensitive moiety. Typically, the glutathione-sensitive moiety is located at the 2'-carbon of the sugar moiety and comprises a sulfonyl group. In certain embodiment, the glutathione-sensitive moiety is compatible with phosphoramidite oligonucleotide synthesis methods, as described, for example, in International Publication No. WO 2018/045317, which is hereby incorporated by reference in its entirety. In certain embodiments, more than two nucleotides of the double-stranded nucleic acid inhibitor molecule are reversibly modified with a glutathione-sensitive moiety. In certain embodiments, most of the nucleotides are reversibly modified with a glutathione-sensitive moiety. In certain embodiments, all or substantially all the nucleotides of the double-stranded nucleic acid inhibitor molecule are reversibly modified with a glutathione-sensitive moiety.

The at least one glutathione-sensitive moiety is typically located at the 5'- or 3'-terminal nucleotide of the sense strand or the antisense strand of the double-stranded nucleic acid inhibitor molecule. However, the at least one glutathione-sensitive moiety may be located at any nucleotide of interest in the double-stranded nucleic acid inhibitor molecule.

In certain embodiments, the double-stranded nucleic acid inhibitor molecule is fully modified, wherein every nucleotide of the sense strand and antisense strand is modified; typically, every nucleotide is modified at the 2'-position of the sugar moiety. In certain embodiments, the fully modified nucleic acid inhibitor molecule does not contain a reversible modification. In some embodiments, at least one, such as at least two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, or 36 nucleotides of the sense strand of the double-stranded nucleic acid inhibitor molecule are modified. In some embodiments, at least one, such as at least two, three, four, five, six, seven, eight, nine, 10, 11, 12, 13, 14, 15, 16, 17, 18, 19, 20, 21, 22, 23, or 24 nucleotides of the antisense strand of the double-stranded nucleic acid inhibitor molecule are modified.

In certain embodiments, the fully modified nucleic acid inhibitor molecule is modified with one or more reversible, glutathione-sensitive moieties. In certain embodiments, substantially all the nucleotides of the double-stranded nucleic acid inhibitor molecule are modified. In certain embodiments, more than half of the nucleotides of the double-stranded nucleic acid inhibitor molecule are modified with a chemical modification other than a reversible modification. In certain embodiments, less than half of the nucleotides of the double-stranded nucleic acid inhibitor molecule are modified with a chemical modification other than a reversible modification. Modifications can occur in groups on the nucleic acid inhibitor molecule or different modified nucleotides can be interspersed.

In certain embodiments of the double-stranded nucleic acid inhibitor molecule, from one to every nucleotide is modified at the 2'-carbon. In certain embodiments, the double-stranded nucleic acid inhibitor molecule is partially or fully modified with 2'-F, 2'-OMe, and/or 2'-MOE. In certain embodiments of the double-stranded nucleic acid inhibitor molecule, from one to every phosphorous atom is modified and from one to every nucleotide is modified at the 2'-carbon of the sugar moiety.

In certain embodiments of the double-stranded nucleic acid inhibitor molecule, every nucleotide on the sense and antisense strands is modified at the 2'-carbon of the sugar moiety. In certain embodiments of the double-stranded nucleic acid inhibitor molecule, every nucleotide on the sense and antisense strands is modified at the 2'-carbon of the sugar moiety with a 2'-F or a 2'-OMe, except for the nucleotides in the second region of the sense strand (R2). In certain embodiments of the double-stranded nucleic acid inhibitor molecule, every nucleotide on the sense and antisense strands is modified at the 2'-carbon of the sugar moiety with a 2'-F or a 2'-OMe, except for the $T_m$-increasing nucleotides in the stem (second duplex or D2). In certain embodiments of the double-stranded nucleic acid inhibitor molecule, every nucleotide on the sense and antisense strands is modified at the 2'-carbon of the sugar moiety with a 2'-F or a 2'-OMe, except for the $T_m$-increasing nucleotides in the stem (second duplex or D2) and the nucleotides in the loop region that are conjugated to a sugar ligand moiety, such as GalNAc.

Methods of Reducing Target Gene Expression

The double-stranded nucleic acid inhibitor molecule, as described herein, can be used in methods of reducing target mRNA expression of any target gene of interest. Typically, the method of reducing mRNA expression comprises administering the double-stranded nucleic acid inhibitor molecule, as described herein, to a sample or to a subject in need thereof in an amount sufficient to reduce mRNA expression of the target gene. The methods may be carried out in vitro or in vivo.

The level or activity of a target RNA can be determined by a suitable method now known in the art or that is later developed. It can be appreciated that the method used to measure a target RNA and/or the "expression" of a target gene can depend upon the nature of the target gene and its encoded RNA. For example, where the target RNA sequence encodes a protein, the term "expression" can refer to a protein or the target RNA/transcript derived from the target gene (either genomic or of exogenous origin). In such instances the expression of the target RNA can be determined by measuring the amount of target RNA/transcript directly or by measuring the amount of protein encoded by the target RNA/transcript. Protein can be measured in protein assays such as by staining or immunoblotting or, if the protein catalyzes a reaction that can be measured, by measuring reaction rates. All such methods are known in the art and can be used. Where target RNA levels are to be measured, art-recognized methods for detecting RNA levels can be used (e.g., RT-PCR, Northern Blotting, etc.). The above measurements can be made on cells, cell extracts, tissues, tissue extracts or another suitable source material.

Pharmaceutical Compositions

The present disclosure provides pharmaceutical compositions comprising a therapeutically effective amount of the double-stranded nucleic acid inhibitor molecule, as described herein, and a pharmaceutically acceptable excipient.

These pharmaceutical compositions may be sterilized by conventional sterilization techniques or may be sterile filtered. The resulting aqueous solutions may be packaged for use as is, or lyophilized, the lyophilized preparation being combined with a sterile aqueous excipient prior to administration. The pH of the preparations typically will be between 3 and 11, more preferably between 5 and 9 or between 6 and 8, and most preferably between 7 and 8, such as 7 to 7.5.

The pharmaceutical compositions of the present disclosure are applied for therapeutic use. Thus, one aspect of the disclosure provides a pharmaceutical composition, which may be used to treat a subject including, but not limited to, a human suffering from a disease or a condition by administering to said subject a therapeutically effective amount of a pharmaceutical composition of the present disclosure. In certain embodiments, the disease or condition is cancer, as described herein.

In certain embodiments, the present disclosure features the use of a therapeutically effective amount of a pharmaceutical composition as described herein for the manufacture of a medicament for treatment of a subject in need thereof. In certain embodiments, the subject has cancer, as described herein.

Pharmaceutically-Acceptable Excipients

The pharmaceutically-acceptable excipients useful in this disclosure are typically conventional. Remington's Pharmaceutical Sciences, by E. W. Martin, Mack Publishing Co., Easton, PA, 15th Edition (1975), describes compositions and formulations suitable for pharmaceutical delivery of one or more therapeutic compositions. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; malt; gelatin; excipients, such as cocoa butter and suppository waxes; oils, such as peanut oil, cottonseed oil, safflower oil, sesame oil, olive oil, corn oil and soybean oil; buffering agents, such as magnesium hydroxide and aluminum hydroxide; (isotonic saline; Ringer's solution); ethyl alcohol; pH buffered solutions; polyols, such as glycerol, propylene glycol, polyethylene glycol, and the like; and other non-toxic compatible substances employed in pharmaceutical formulations.

Dosage Forms

The pharmaceutical compositions may be formulated with conventional excipients for any intended route of administration, which may be selected according to ordinary practice.

In one embodiment, the pharmaceutical composition contains the double-stranded nucleic acid inhibitor molecule, as described herein, and is suitable for parenteral administration, for example, by subcutaneous, intramuscular, intravenous or epidural injection. Typically, the pharmaceutical compositions of the present disclosure are formulated in liquid form for parenteral administration.

Dosage forms suitable for parenteral administration typically include one or more suitable vehicles for parenteral administration including, by way of example, sterile aqueous solutions, saline, low molecular weight alcohols such as propylene glycol, polyethylene glycol, vegetable oils, gelatin, fatty acid esters such as ethyl oleate, and the like. The parenteral formulations may contain sugars, alcohols, antioxidants, buffers, bacteriostats, solutes which render the formulation isotonic with the blood of the intended recipient or suspending or thickening agents. Proper fluidity can be maintained, for example, by using surfactants. Liquid formulations containing the double-stranded nucleic acid inhibitor can be lyophilized and stored for later use upon reconstitution with a sterile injectable solution.

The pharmaceutical compositions may also be formulated for other routes of administration including topical or transdermal administration, rectal or vaginal administration, ocular administration, nasal administration, buccal administration, or sublingual administration using well known techniques.

Delivery Agents

The double-stranded nucleic acid inhibitor molecule, as described herein, may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the double-stranded nucleic acid inhibitor molecule is formulated in a lipid nanoparticle (LNP). Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as LIPEX® Extruder (Northern Lipids, Inc). To prepare a lipid nanoparticle for therapeutic use, it may desirable to remove solvent (e.g., ethanol) used to form the nanoparticle and/or exchange buffer, which can be accomplished by, for example, dialysis or tangential flow filtration. Methods of making lipid nanoparticles containing nucleic acid interference molecules are known in the art, as disclosed, for example in U.S. Published Patent Application Nos. 2015/0374842 and 2014/0107178.

In certain embodiments, the LNP comprises a core lipid component comprising a cationic liposome and a pegylated lipid. The LNP can further comprise one or more envelope lipids, such as a cationic lipid, a structural or neutral lipid, a sterol, a pegylated lipid, or mixtures thereof.

Cationic lipids for use in LNPs are known in the art, as discussed for example in U.S. Published Patent Application Nos. 2015/0374842 and 2014/0107178. Typically, the cationic lipid is a lipid having a net positive charge at physiological pH. In certain embodiments, the cationic liposome is DODMA, DOTMA, DL-048, or DL-103. In certain embodiments the structural or neutral lipid is DSPC, DPPC or DOPC. In certain embodiments, the sterol is cholesterol. In certain embodiments, the pegylated lipid is DMPE-PEG, DSPE-PEG, DSG-PEG, DMPE-PEG2K, DSPE-PEG2K, DSG-PEG2K, or DSG-mPEG. In one embodiment, the cationic lipid is DL-048, the pegylated lipid is DSG-mPEG and the one or more envelope lipids are DL-103, DSPC, cholesterol, and DSPE-mPEG. See e.g., FIG. 13, showing one non-limiting embodiment of an LNP that can used to formulate the double-stranded nucleic acid inhibitor molecule.

In certain embodiments, the double-stranded nucleic acid inhibitor molecule is covalently conjugated to a ligand that directs delivery of the oligonucleotide to a tissue of interest. Many such ligands have been explored. See, e.g., Winkler, Ther. Deliv. 4(7): 791-809 (2013). For example, the double-stranded nucleic acid inhibitor molecule can be conjugated to one or more sugar ligand moieties (e.g., N-acetylgalactosamine (GalNAc)) to direct uptake of the oligonucleotide into the liver. See, e.g., U.S. Pat. Nos. 5,994,517; 5,574,142; WO 2016/100401. In certain embodiments, the one or more ligands are conjugated to one or more nucleotides in the tetraloop of the double-stranded nucleic acid inhibitor molecule.

In certain embodiments, the double-stranded nucleic acid inhibitor molecule is conjugated to 2-4 sugar ligand moieties in the tetraloop. In one embodiment, two of the nucleotides in the tetraloop are conjugated to a sugar ligand moiety. In one embodiment, three of the nucleotides in the tetraloop are conjugated to a sugar ligand moiety. In another embodiment, four of the nucleotides in the tetraloop are conjugated to a sugar ligand moiety. In certain embodiments, the sugar ligand moiety is GalNAc. Other ligands that can be used include, but are not limited to, mannose-6-phosphate, cholesterol, folate, transferrin, and galactose (for other specific exemplary ligands see, e.g., WO 2012/089352).

The ligand can be conjugated to any part of the nucleotide as long as it is capable of directing delivery of the oligonucleotide to the tissue of interest. In certain embodiments, the ligand (e.g., GalNAc) is conjugated to the nucleotide at the 2'-position of the sugar moiety.

Methods of Administration/Treatment

One embodiment is directed to a method of treating a disorder, comprising administering to a subject a pharmaceutical composition comprising a therapeutically effective amount of the double-stranded nucleic acid inhibitor molecule, as described herein.

In certain embodiments the pharmaceutical compositions disclosed herein may be useful for treatment or prevention of symptoms related to proliferative, inflammatory, autoimmune, neurologic, ocular, respiratory, metabolic, dermatological, auditory, liver, kidney, or infectious diseases. One embodiment is directed to a method of treating a proliferative, inflammatory, autoimmune, neurologic, ocular, respiratory, metabolic, dermatological, auditory, liver, kidney, or infectious disease, comprising administering to a subject a pharmaceutical composition comprising a therapeutically effective amount of a double-stranded nucleic acid inhibitor molecule, as described herein.

In certain embodiments, the disorder is a rare disease, a chronic liver disease, a chronic kidney disease, cardiovascular disease or a viral infectious disease. In certain embodiments, the disorder is hyperoxaluria, including primary hyperoxaluria (PH1, PH2, or PH3) or idiopathic hyperoxaluria. In certain embodiments, the disorder is chronic kidney disorder (CKD). In certain embodiments, the disorder is pyruvate dehydrogenase deficiency. In certain embodiments, the disorder is alpha-1 antitrypsin (A1AT) deficiency.

In certain embodiments, the disorder is a cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T-cell lymphomas, non-Hodgkin lymphoma, precursor T-lymphoblastic lymphoma/leukemia, peripheral T-cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Typically, the present disclosure features methods of treating liver cancer, liver carcinoma, hepatoma, hepatocellular carcinoma, cholangiocarcinoma and hepatoblastoma by administering a therapeutically effective amount of a pharmaceutical composition as described herein.

In some embodiments, the present disclosure provides a method for reducing expression of a target gene in a subject comprising administering a pharmaceutical composition to a subject in need thereof in an amount sufficient to reduce expression of the target gene, wherein the pharmaceutical composition comprises a double-stranded nucleic acid inhibitor molecule as described herein and a pharmaceutically acceptable excipient as also described herein.

The target gene may be a target gene from any mammal, such as a human target gene. Any target gene may be silenced according to the instant methods. In certain embodiments, the target gene is associated with chronic liver disease or chronic kidney disease, including, for example, AGXT, GRHPR, HOGA1, HAO1, SERPINA1, or LDHA. In certain embodiments, the target gene is associated with a viral infectious disease, including, for example, an HBV gene or an HCV gene. In certain embodiments, the target gene is associated with cardiovascular disease, including, for example, APOC3 or PCSK9. In certain embodiments, the target gene is associated with alcohol metabolism and liver function, including, for example, ALDH2.

Other exemplary target genes include, but are not limited to, KRAS, Factor VII, Eg5, PCSK9, TPX2, apoB, SAA1, TTR, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, and combinations thereof.

Dosing and Schedule

Typically, the double-stranded nucleic acid inhibitor molecule is administered parenterally (such as via intravenous, intramuscular, or subcutaneous administration). In other embodiments, the pharmaceutical composition is delivered via local administration or systemic administration. However, the pharmaceutical compositions disclosed herein may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the double-stranded nucleic acid inhibitor molecule is administered at a dosage of 20 micrograms to 10 milligrams per kilogram body weight of the recipient per day, 100 micrograms to 5 milligrams per kilogram, 0.25 milligrams to 5.0 milligrams per kilogram, or 0.5 to 3.0 milligrams per kilogram. Typically, the double-stranded nucleic acid inhibitor molecule is administered at a dosage of about 0.25 to 2.0 milligrams per kilogram body weight of the recipient per day.

A pharmaceutical composition of the instant disclosure may be administered every day, or intermittently. For example, intermittent administration of the double-stranded nucleic acid inhibitor molecule may be administration one to six days per week, one to six days per month, once weekly, once every other week, once monthly, once every other month, once every three months, or once or twice per year or divided into multiple yearly, monthly, weekly, or daily doses. In some embodiments, intermittent dosing may mean administration in cycles with the initial double-stranded nucleic acid inhibitor molecule administration followed by a rest period with no administration for up to one week, up to one month, up to two months, up to three months or up to six months or more) or it may mean administration on alternate days, weeks, months or years.

The therapeutically effective amount of the double-stranded nucleic acid inhibitor molecule may depend on the route of administration and the physical characteristics of the patient, such as the size and weight of the subject, the extent of the disease progression or penetration, the age, health, and sex of the subject and can be adjusted as necessary depending on these and other factors.

EXAMPLES

Example 1: In Vivo SAA1 mRNA Knockdown

Figure 1:
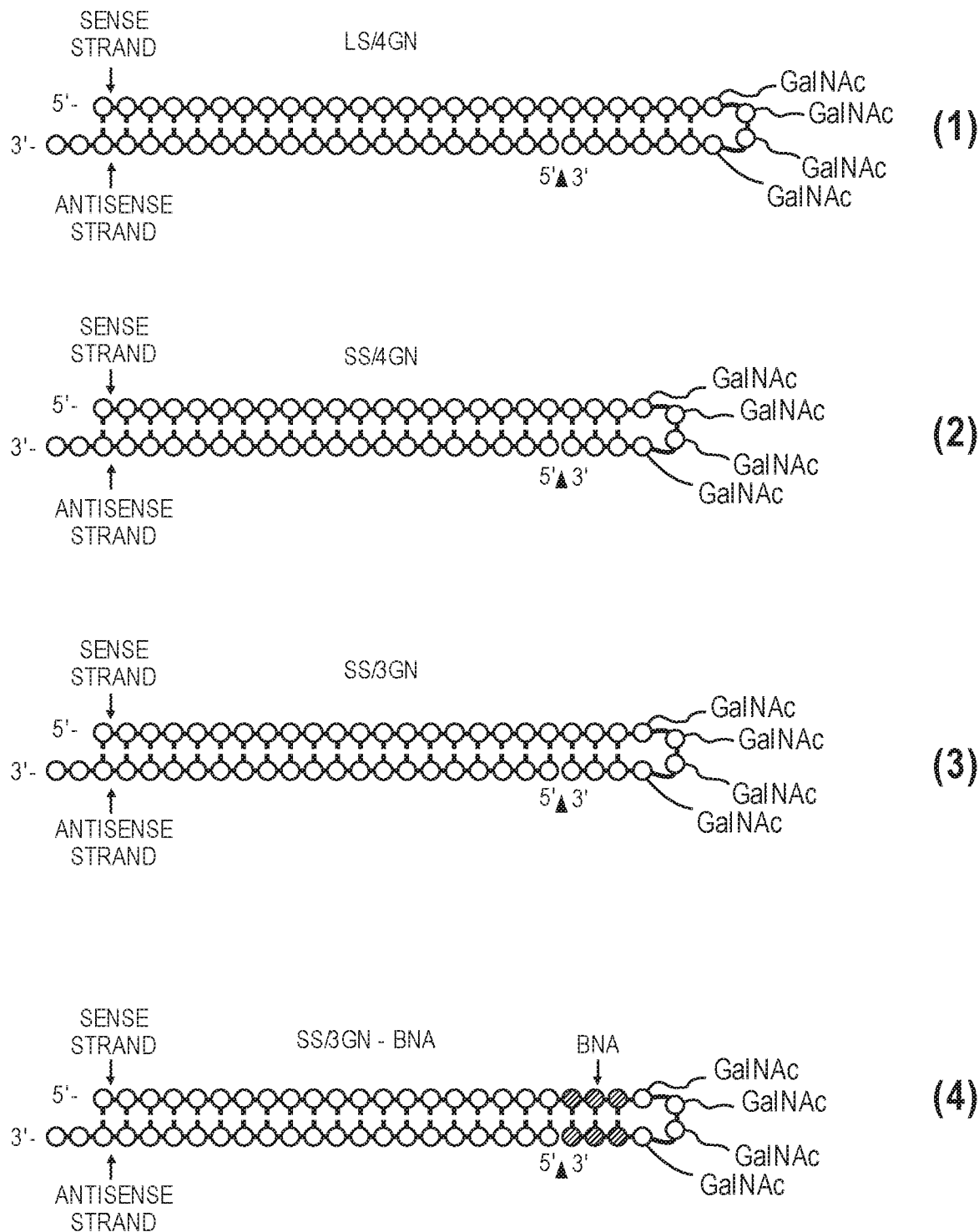
FIG. 1 schematically shows the structures of four, exemplary double-stranded nucleic acid inhibitor molecules that target the same sequence in the human SAA1 gene (Constructs 1-4), as discussed in Example 1. The sense strand of Construct 1 includes a stem duplex of 6 base pairs, referred to herein as a "long stem," and a tetraloop. Each nucleotide of the tetraloop is conjugated to a single GalNAc molecule. Construct 1 is also called "LS/4GN." The sense strand of Construct 2 includes a stem duplex of 3 base pairs, referred to herein as a "short stem," and a tetraloop. Each nucleotide of the tetraloop is conjugated to a single GalNAc molecule. Construct 2 is also called "SS/4GN." Construct 3 has a short stem of 3 base pairs and is identical to Construct 2 except that only 3 of the 4 nucleotides of the tetraloop are conjugated to GalNAc. Construct 3 is also called "SS/3GN." Construct 4 has a short stem of 3 base pairs and is identical to Construct 3 except that it contains 6 bicyclic nucleotides in the stem. Construct 4 is also called "SS/3GN-BNA."

CD-1 female mice were divided into study groups and dosed with the test serum amyloid A1 (SAA1) nucleic acid inhibitor molecule assigned to that group. The test SAA1 nucleic acid inhibitor molecules used in Example 1 are shown in FIG. 1. Except for the nucleotides in the loop that are conjugated to GalNAc and the bicyclic nucleotides, every other nucleotide in the test SAA1 nucleic acid inhibitor molecules is modified at the 2'-position of the sugar moiety with either 2'-F or 2'-OMe. The test SAA1 nucleic acid inhibitor molecules differed in the following respects: length of the stem portion (short vs. long); presence or absence of bicyclic nucleotides; and number of GalNAcs in loop (3 vs. 4). The SAA1 nucleic acid inhibitor molecules in FIG. 1 are summarized in the following table:

TABLE 1

| SAA1 nucleic acid inhibitors in FIG. 1 | | | | |
|---|---|---|---|---|
| # | Name | Stem Length | Bicyclic Nucleotides | GalNAcs in loop | G1 |
| 1 | LS/4GN | Long | None | 4 | 2'-F |
| 2 | SS/4GN | Short | None | 4 | 2'-F |
| 3 | SS/3GN | Short | None | 3 | 2'-F |
| 4 | SS/3GN-BNA | Short | BNA | 3 | 2'-F |

The short stem constructs 2 and 3 are identical with the only difference being the number of GalNAcs in the loop (4 vs. 3). The long stem construct 1 is identical to short stem construct 2 except that construct 1 has a stem duplex of 6 base pairs, whereas construct 2 has a stem duplex of 3 base pairs. The short stem constructs 3 and 4 are identical with the only difference being the presence of 6 bicyclic nucleotides in the stem of construct 4. The bicyclic nucleotide used in construct 4 is BNA$^{NC}$ [NMe], where the bridge that connects the 2'-carbon and the 4'-carbon of the bicyclic nucleotide is 4'-CH$_2$—N(CH$_3$)—O-2'.

An AAV9 (Adeno-Associated Virus) vector encoding the human SAA1 (NM_000331.5) gene (hSAA1) under the TBG (thyroxine binding globulin) promoter was synthesized by Vigene Biosciences Inc. CD-1 female mice were dosed intravenously at 5×10$^{12}$ copies of viral genome per mouse with the hSAA1_AAV9 vector. Mice were bled every week using tail-nick to get 10 ul whole blood that was immediately diluted 1:20 in the hSAA1 ELISA buffer and stored at −20° C. until analysis. After 3 weeks, circulating levels of hSAA1 protein in mouse blood were determined using a hSAA1 ELISA kit (Invitrogen T$_m$ Cat. no KHA0011; Thermo Fisher Scientific, Waltham, MA). Mice were sorted into groups of 4 based on circulating hSAA1 concentrations at week 3, in an effort to achieve comparable mean circulating concentration of hSAA1 protein in each group. Mice were then dosed subcutaneously at study day 0 with PBS or 1 mg/kg of the respective SAA1 nucleic acid inhibitor molecule. Mice were bled every week thereafter and whole blood collected and analyzed to measure the circulating hSAA1 levels until the end of the experiment. Circulating hSAA1 concentrations were expressed by normalizing to predose (week 3 post hSAA1_AAV9) level for the respective mice and time matched PBS group.

Figure 2:
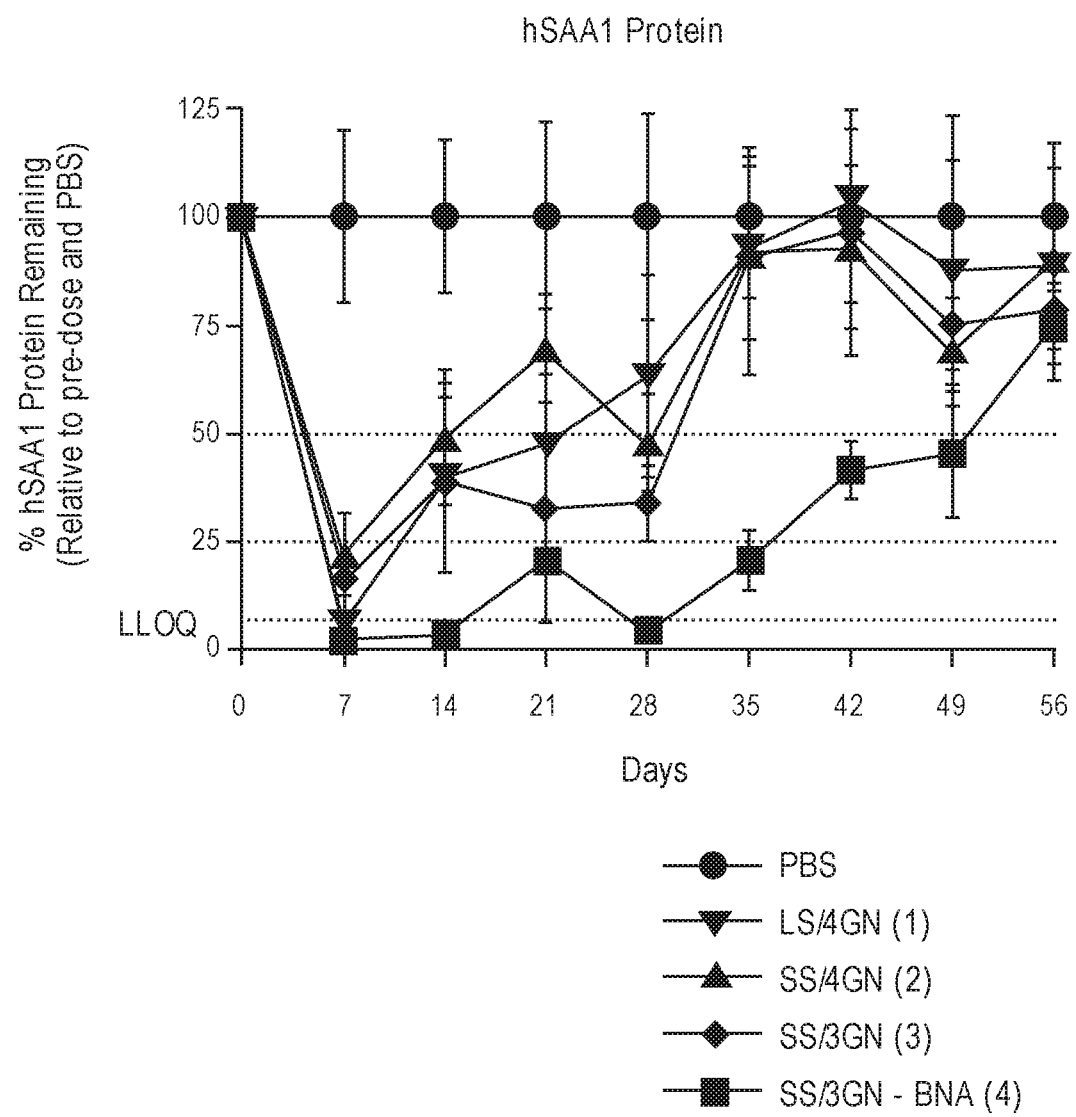
FIG. 2 shows the knockdown of human SAA1 protein following administration of Constructs 1-4 (see FIG. 1) to CD-1 mice that were previously dosed with an AAV9 vector to express hSAA1, as explained in Example 1. The inclusion of bicyclic nucleotides in the short stem of Construct 4 (SS/3GN-BNA) improved the potency and duration of hSAA1 knockdown as compared to the long stem and short stem controls.

The short stem (3 base pairs in the stem) SAA1 nucleic acid inhibitor molecules containing bicyclic nucleotides were compared to the corresponding short stem control without the bicyclic nucleotides. They were also compared to the longer stem control (6 base pairs in the stem) without the bicyclic nucleotides. As seen in FIG. 2, the SAA1 nucleic acid inhibitor molecules containing bicyclic nucleotides in the short stem showed significantly improved potency and duration of SAA1 knock down, as compared to the corresponding short stem and long stem controls.

Example 2: In Vivo APOC3 mRNA Knockdown in the Liver

Figure 3A:
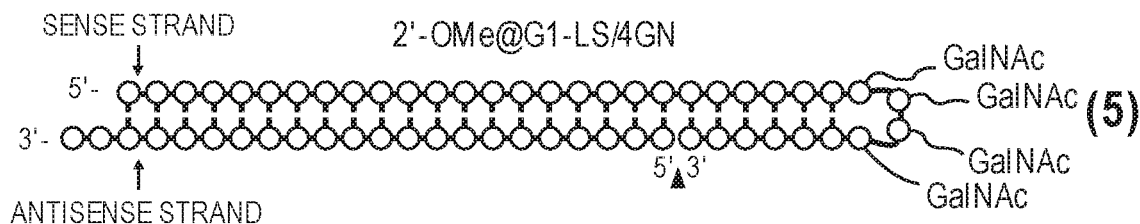
FIG. 3A schematically shows the structures of six, exemplary double-stranded nucleic acid inhibitor molecules that target the same sequence in the human APOC3 gene (Constructs 5-10), as discussed in Example 2. In Constructs 5-10, the nucleotide at position 1 of the antisense (or guide) strand contains a 2'-OMe modification. The long stem Constructs 5 (LS/4GN) and 8 (LS/3GN) are identical except that the tetraloop in Construct 5 contains 4 nucleotides conjugated to a single GalNAc whereas the tetraloop in Construct 8 contains 3 nucleotides conjugated to a single GalNAc. The short stem Constructs 6 (SS/4GN) and 9 (SS/3GN) are identical except that the tetraloop in Construct 6 contains 4 nucleotides conjugated to a single GalNAc whereas the tetraloop in Construct 9 contains 3 nucleotides conjugated to a single GalNAc. The short stem Constructs 7 (SS/4GN-BNA) and 10 (SS/3GN-BNA) are identical to Constructs 6 (SS/4GN) and 9 (SS/3GN), respectively, except that Constructs 7 and 10 contain 6 bicyclic nucleotides in the stem duplex.
Figure 3A:
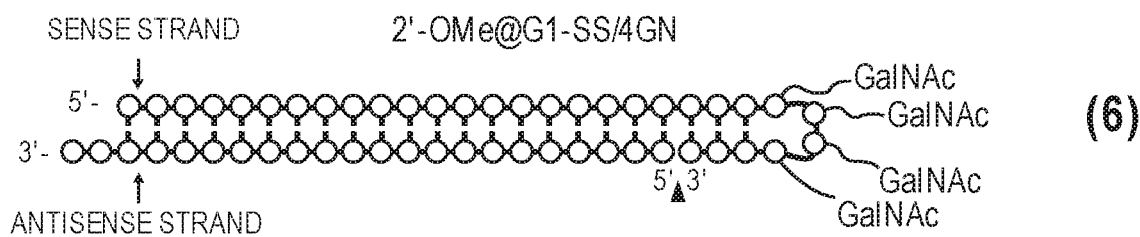
Figure 3A:
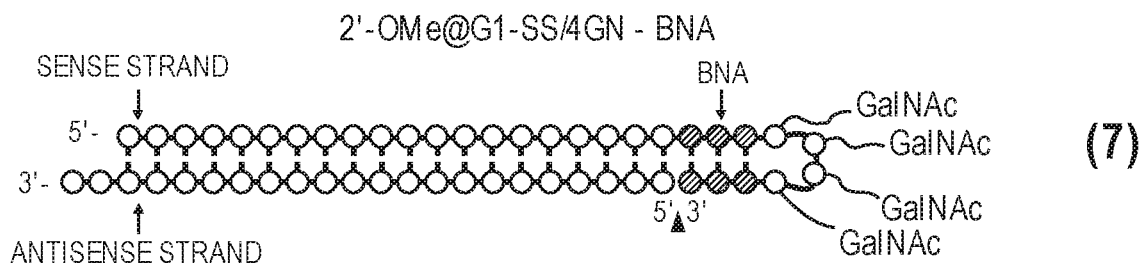
Figure 3A:
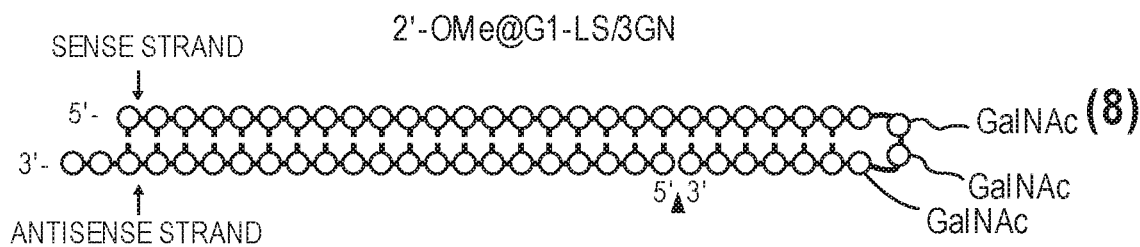
Figure 3A:
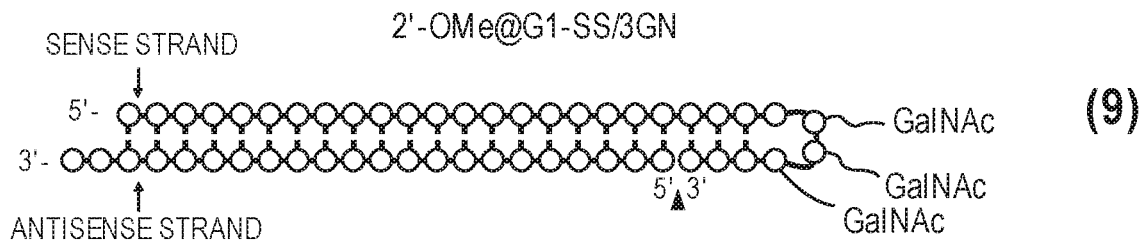
Figure 3A:
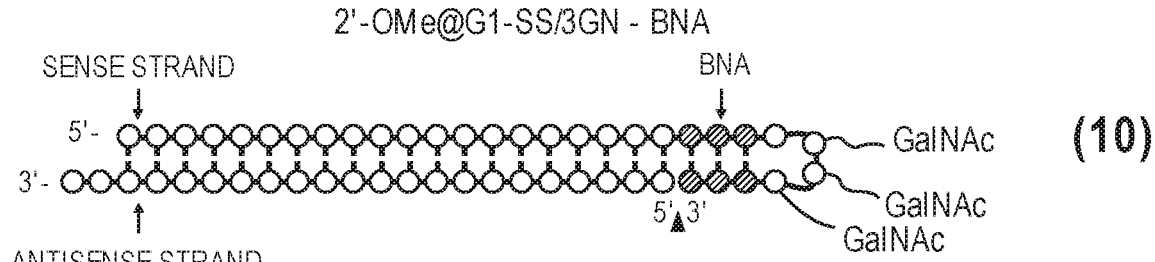
Figure 3B:
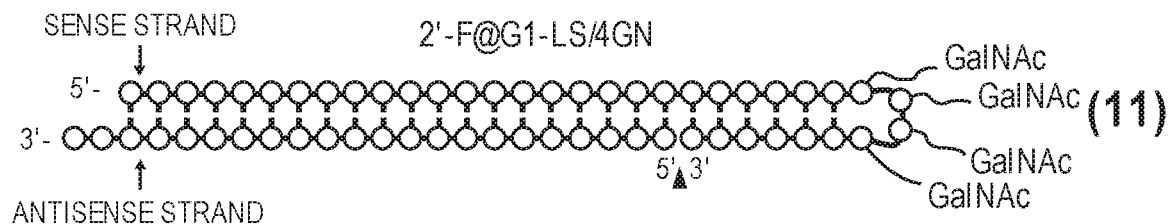
FIG. 3B schematically shows the structures of six, exemplary double-stranded nucleic acid inhibitor molecules that target the same sequence in the human APOC3 gene (Constructs 11-16), as discussed in Example 2. In Constructs 11-16, the nucleotide at position 1 of the antisense (or guide) strand contains a 2'-F modification. The long stem Constructs 11 (LS/4GN) and 14 (LS/3GN) are identical except that the tetraloop in Construct 11 contains 4 nucleotides conjugated to a single GalNAc whereas the tetraloop in Construct 14 contains 3 nucleotides conjugated to a single GalNAc. The short stem Constructs 12 (SS/4GN) and 15 (SS/3GN) are identical except that the tetraloop in Construct 12 contains 4 nucleotides conjugated to a single GalNAc whereas the tetraloop in Construct 15 contains 3 nucleotides conjugated to a single GalNAc. The short stem Constructs 13 (SS/4GN-BNA) and 16 (SS/3GN-BNA) are identical to Constructs 12 (SS/4GN) and 15 (SS/3GN), respectively, except that Constructs 13 and 16 contain 6 bicyclic nucleotides in the stem.
Figure 3B:
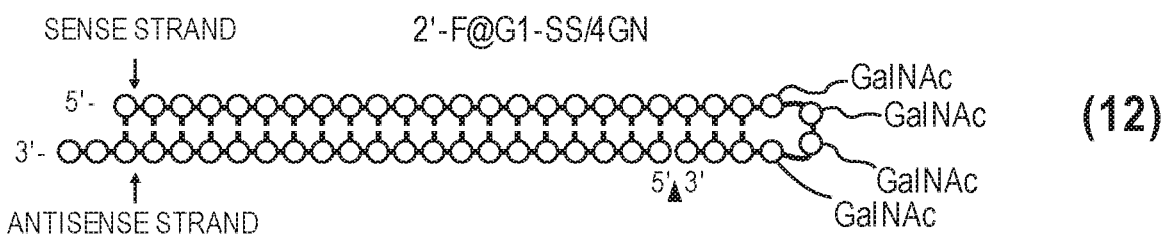
Figure 3B:
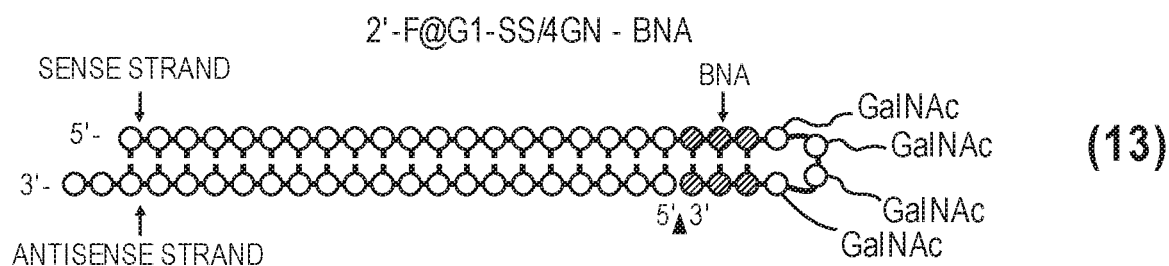
Figure 3B:
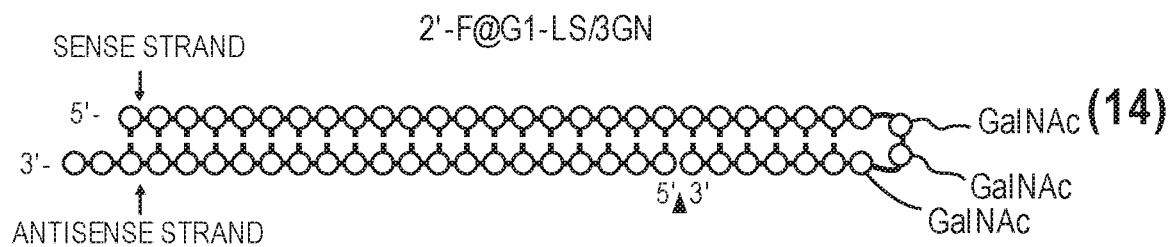
Figure 3B:
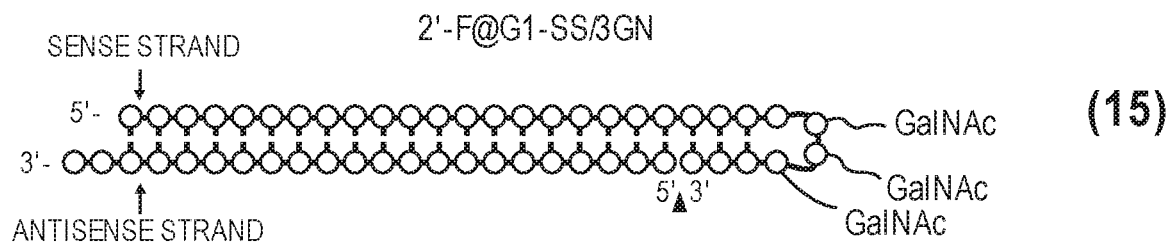
Figure 3B:
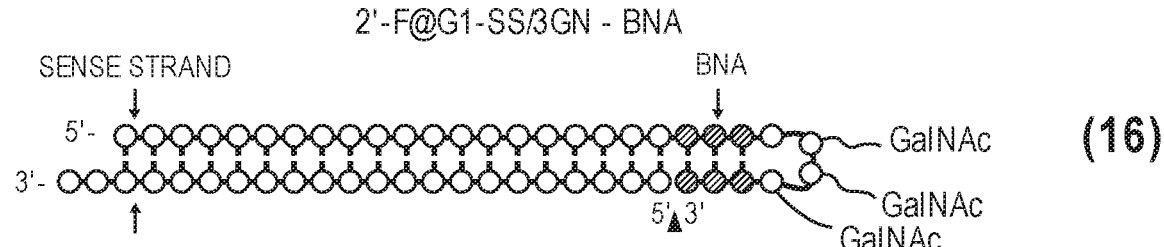

CD-1 female mice were divided into study groups and dosed with the test Apolipoprotein $C_3$ (APOC3) nucleic acid inhibitor molecule assigned to that group. The test APOC3 nucleic acid inhibitor molecules used in Example 2 are shown in FIGS. 3A and 3B. Except for the nucleotides in the loop that are conjugated to GalNAc and the bicyclic nucleotides, every other nucleotide in the test APOC3 nucleic acid inhibitor molecules is modified at the 2'-position of the sugar moiety with either 2'-OMe or 2'-F. The test APOC3 nucleic acid inhibitor molecules differed in the following respects: length of the stem portion (short vs. long); presence or absence of bicyclic nucleotides; number of GalNAcs in the loop (3 vs. 4); and position 1 (G1) of the guide strand (2'-OMe vs. 2'-F). The APOC3 nucleic acid inhibitor molecules in FIG. 3A are summarized in the following table:

TABLE 2

APOC3 nucleic acid inhibitors in FIG. 3A (2'-OMe at G1)

| # | Name | Stem Length | Bicyclic Nucleotides | GalNAcs in loop | G1 |
|---|---|---|---|---|---|
| 5 | LS/4GN | Long | None | 4 | 2'-OMe |
| 6 | SS/4GN | Short | None | 4 | 2'-OMe |
| 7 | SS/4GN-BNA | Short | BNA | 4 | 2'-OMe |
| 8 | LS/3GN | Long | None | 3 | 2'-OMe |
| 9 | SS/3GN | Short | None | 3 | 2'-OMe |
| 10 | SS/3GN-BNA | Short | BNA | 3 | 2'-OMe |

The long stem constructs 5 and 8 are identical with the only difference being the number of GalNAcs in the loop (4 vs. 3). The long stem construct 5 is identical to short stem construct 6 except that construct 5 has a stem duplex of 6 base pairs, whereas construct 6 has a stem duplex of 3 base pairs with 6 bicyclic nucleotides. The short stem constructs 6 and 7 are identical with the only difference being the presence of 6 bicyclic nucleotides in the stem of construct 7. The bicyclic nucleotide used in construct 7 is $BNA^{NC}$ [NMe]. The short stem constructs 6 and 9 are identical except for the number of GalNAcs in the loop (4 vs. 3). Similarly, the BNA-containing short stem constructs 7 and 10 are identical except for the number of GalNAcs in the loop (4 vs. 3). The short stem constructs 9 and 10 are identical with the only difference being the presence of 6 bicyclic nucleotides in the stem of construct 10. The bicyclic nucleotide used in construct 10 is $BNA^{NC}$ [NMe].

The APOC3 nucleic acid inhibitor molecules in FIG. 3B are summarized in the following table:

TABLE 3

APOC3 Nucleic Acid Inhibitors in FIG. 3B (2'-F at G1)

| # | Name | Stem Length | Bicyclic Nucleotides | GalNAcs in loop | G1 |
|---|---|---|---|---|---|
| 11 | LS/4GN | Long | None | 4 | 2'-F |
| 12 | SS/4GN | Short | None | 4 | 2'-F |
| 13 | SS/4GN-BNA | Short | BNA | 4 | 2'-F |
| 14 | LS/3GN | Long | None | 3 | 2'-F |
| 15 | SS/3GN | Short | None | 3 | 2'-F |
| 16 | SS/3GN-BNA | Short | BNA | 3 | 2'-F |

The long stem (or LS) constructs 11 and 14 are identical with the only difference being the number of GalNAcs in the loop (4 vs. 3). The long stem construct 11 is identical to short stem (or SS) construct 12 except that construct 11 has a stem duplex of 6 base pairs, whereas construct 12 has a stem duplex of 3 base pairs with 6 bicyclic nucleotides. The short stem constructs 12 and 13 are identical with the only difference being the presence of 6 bicyclic nucleotides in the stem of construct 13. The bicyclic nucleotide used in construct 13 is $BNA^{NC}$ [NMe]. The short stem constructs 12 and 15 are identical except for the number of GalNAcs in the loop (4 vs. 3). Similarly, the BNA-containing short stem constructs 13 and 16 are identical except for the number of GalNAcs in the loop (4 vs. 3). The short stem constructs 15 and 16 are identical with the only difference being the presence of 6 bicyclic nucleotides in the stem of construct 16. The bicyclic nucleotide used in construct 16 is $BNA^{NC}$ [NMe].

Animals were dosed subcutaneously with 1 mg/kg of the assigned APOC3 nucleic acid inhibitor molecule. Liver tissue was collected by taking two 4 mm punch biopsies which were stored in Invitrogen $T_m$ RNAlater™ solution (Thermo Fisher Scientific, Waltham, MA) for later mRNA analysis.

Figure 4:
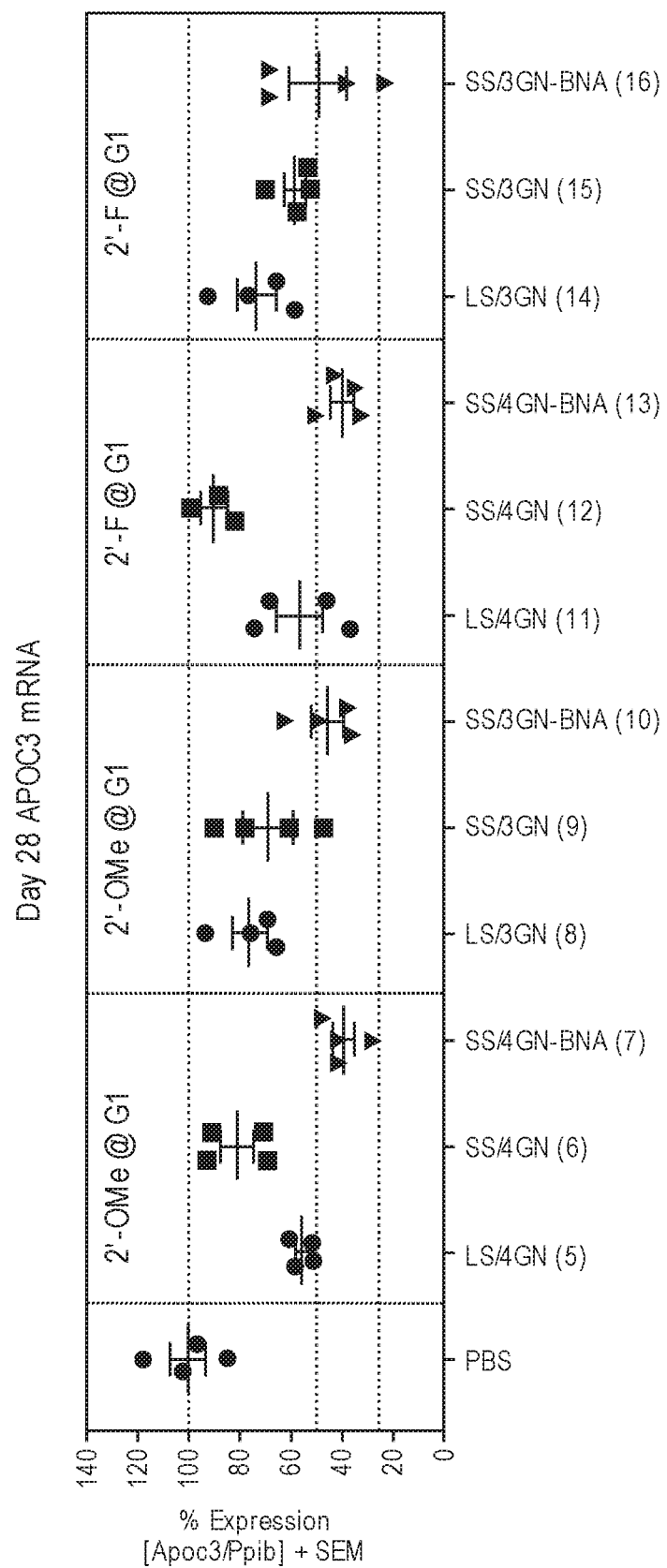
FIG. 4 shows the knockdown of APOC3 mRNA following administration of Constructs 5-16 (see FIGS. 3A and 3B) to CD-1 mice, as explained in Example 2. The inclusion of bicyclic nucleotides in the short stem of Constructs 7 (SS/4GN-BNA), 10 (SS/3GN-BNA), 13 (SS/4GN-BNA), and 16 (SS/3GN-BNA) improved the potency and duration of APOC3 knockdown as compared to the long stem and short stem controls.

The short stem (3 base pairs in the stem) APOC3 nucleic acid inhibitor molecules containing bicyclic nucleotides were compared to the corresponding short stem version without the bicyclic nucleotides. They were also compared to the longer stem versions (6 base pairs in the stem) without the bicyclic nucleotides. As demonstrated with the data shown in FIG. 4, the APOC3 nucleic acid inhibitor molecules containing bicyclic nucleotides in the short stem showed significantly more knockdown of APOC3 mRNA in wild type mice at Day 28 as compared to the corresponding short stem and long stem controls. The trend was observed in nucleic acid inhibitor molecules having either 2'-OMe or 2'-F at guide position 1. The trend was also the same regardless of the number of GalNAc ligands used in the loop (4 GalNAcs vs 3 GalNAcs).

Example 3: PCSK9 mRNA Knockdown in the HDI Mouse Model

A hydronynamic injection (HDI) mouse model was used to study PCSK9 mRNA knockdown. HDI is a method used to deliver nucleic acids to hepatocytes in mice via intravenous tail injection. In this experiment, HDI was used to deliver plasmid DNA containing human PCSK9, as explained in more detail below.

Figure 5:
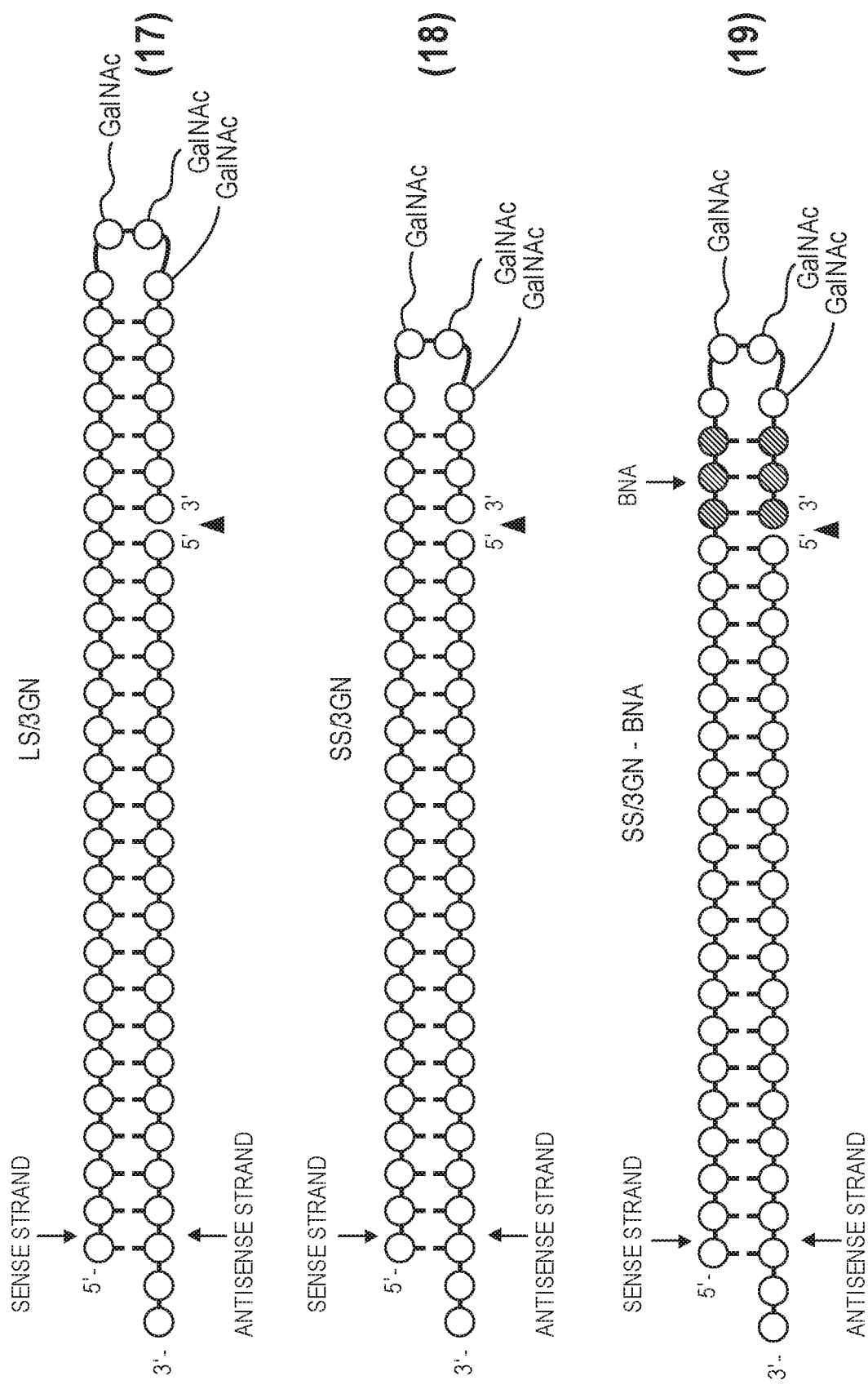
FIG. 5 schematically shows the structures of three, exemplary double-stranded nucleic acid inhibitor molecules that target the same sequence in the human PCSK9 gene (Constructs 17-19), as discussed in Examples 3 and 5. Constructs 17 (LS/3GN) and 18 (SS/3GN) are identical except that Construct 17 contains a long stem (6 base pairs) and Construct 18 contains a short stem (3 base pairs). Short stem Constructs 18 and 19 (SS/3GN-BNA) are identical except that Construct 19 contains 6 bicyclic nucleotides in the stem.

CD-1 female mice were divided into study groups and dosed with the test PCSK9 nucleic acid inhibitor molecule assigned to that group. The test PCSK9 nucleic acid inhibitor molecules used in Example 3 are shown in FIG. 5. Except for the nucleotides in the loop that are conjugated to GalNAc and the bicyclic nucleotides, every other nucleotide in the test PCSK9 nucleic acid inhibitor molecules is modified at the 2'-position of the sugar moiety with either 2'-OMe or 2'-F (modification pattern 2 or "M2"). The test PCSK9 nucleic acid inhibitor molecules differed in the following respects: length of the stem portion (short vs. long) and presence or absence of bicyclic nucleotides. The PCSK9 nucleic acid inhibitor molecules in FIG. 5 are summarized in the following table:

TABLE 4

PCSK9 nucleic acid inhibitors in FIG. 5

| # | Name | Modification Pattern | Stem Length | Bicyclic Nucleotides | GalNAcs in loop | G1 |
| --- | --- | --- | --- | --- | --- | --- |
| 17 | LS/3GN | Pattern 2 | Long | None | 3 | 2'-OMe |
| 18 | SS/3GN | Pattern 2 | Short | None | 3 | 2'-OMe |
| 19 | SS/3GN-BNA | Pattern 2 | Short | BNA | 3 | 2'-OMe |

The long stem construct 17 is identical to short stem construct 18 except that construct 17 has a stem duplex of 6 base pairs, whereas construct 18 has a stem duplex of 3 base pairs. The short stem constructs 18 and 19 are identical with the only difference being the presence of 6 bicyclic nucleotides in the stem of construct 19. The bicyclic nucleotide used in construct 16 is BNA$^{NC}$ [NMe].

Mice were dosed subcutaneously with 0.5 mg/kg of the assigned test article. A plasmid was designed to express human PCSK9 in mice (pCDNA3/hPCSK9). On day 11 or day 19 after the subcutaneous dosing of test articles, 2 ml of pCDNA3/hPCSK9 ($1\times10^{12}$ copies suspended in PBS) was administered to the mice by tail vein intravenous injection. On day 12 or day 20 liver tissue was collected by taking two 4 mm punch biopsies and processed to RNA isolation, cDNA synthesis, and q-RT PCR, according to the manufacturer's protocol.

Figure 6:
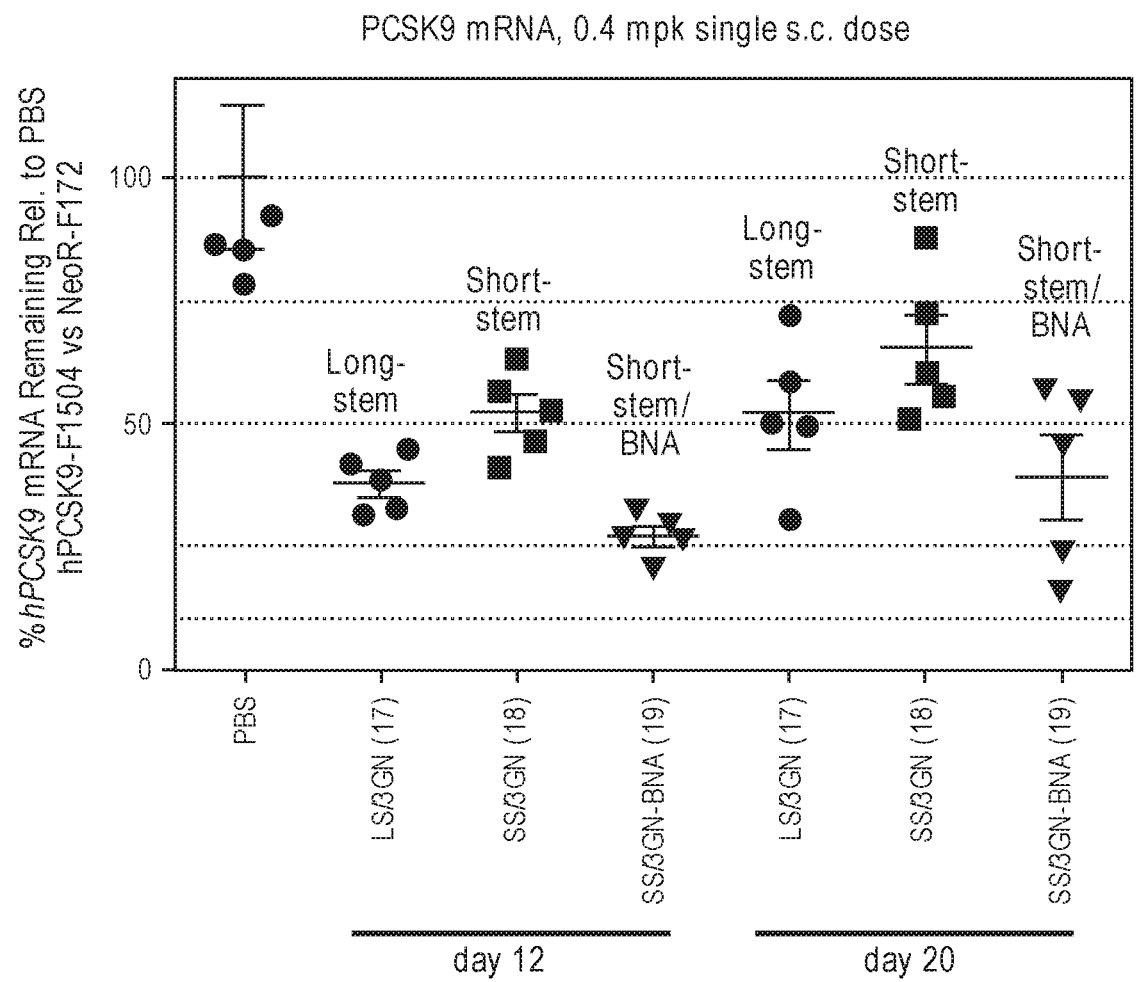
FIG. 6 shows the knockdown of human PCSK9 mRNA on days 12 and 20 following administration of Constructs 17-19 (see FIG. 5) to CD-1 mice that were also dosed with an hPCSK9 expressing plasmid on days 11 and 19, as explained in Example 3. The inclusion of bicyclic nucleotides in the short stem of Construct 19 (SS/3GN-BNA) improved the potency and duration of PCSK9 knockdown as compared to the long stem and short stem controls.

As shown in FIG. 6, PCSK9 nucleic acid inhibitor molecules containing bicyclic nucleotides in the short stem showed improved potency and duration (day 12 and day 20) as compared to the corresponding short stem and long stem controls in the study.

Example 4: PCSK9 mRNA Knockdown in AAV Mouse Model

C57BL/6J female mice were intravenously injected with pAAV9-hPCSK9 ($1\times10^{12}$ copies), an adenovirus-associated virus (AAV) plasmid that expresses human PCSK9 (pAAV9-hPCSK9). Animals were bled weekly via lateral tail vein puncture and blood was processed to plasma. Human PCSK9 expression was measured according the manufacturer's protocol (Human PCSK9 ELISA kit, ab209884, Abcam, Cambridge, UK). When human PCSK9 expression was stabilized, animals were dosed subcutaneously with 1 mg/kg of the assigned test PCSK9 nucleic acid inhibitor molecule. Again, animals were bled weekly to determine the duration of knockdown.

Figure 7:
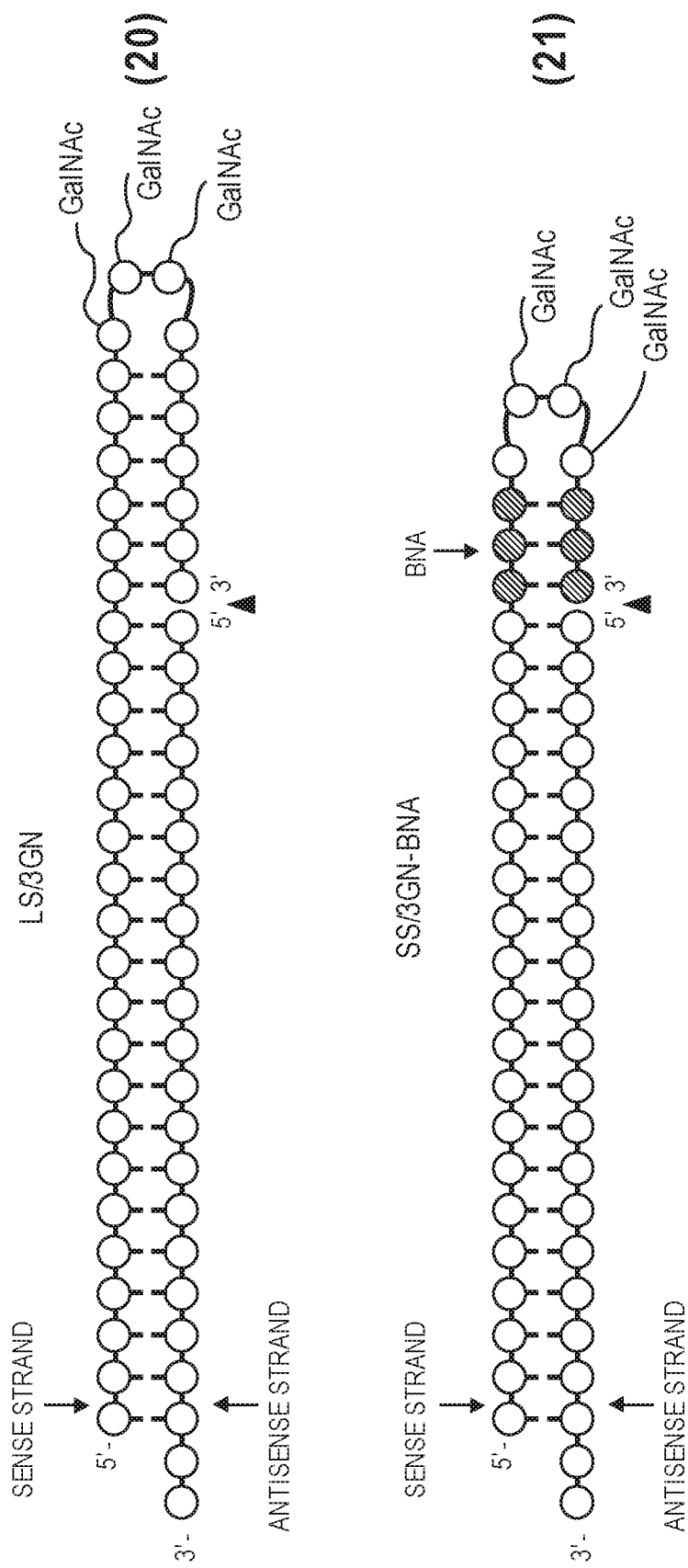
FIG. 7 schematically shows the structures of two, exemplary double-stranded nucleic acid inhibitor molecules that target the same sequence in the human PCSK9 gene (Constructs 20-21), as discussed in Example 4. Constructs 20 (LS/3GN) and 21 (SS/3GN-BNA) are identical except that Construct 20 has a long stem (6 base pairs) and Construct 21 has a short stem (3 base pairs) containing 6 bicyclic nucleotides.

The test PCSK9 nucleic acid inhibitor molecules used in this are shown in FIG. 7. The nucleotide sequences of the test PCSK9 nucleic acid inhibitor molecules are the same as those used in Example 3. Except for the nucleotides in the loop that are conjugated to GalNAc and the bicyclic nucleotides, every other nucleotide in the test PCSK9 nucleic acid inhibitor molecules is modified at the 2'-position of the sugar moiety with either 2'-OMe or 2'-F (modification pattern 1 or "M1"). The test PCSK9 nucleic acid inhibitor molecules differed in the following respects: length of the stem portion (short vs. long) and presence or absence of bicyclic nucleotides. The PCSK9 nucleic acid inhibitor molecules in FIG. 7 are summarized in the following table:

TABLE 5

PCSK9 nucleic acid inhibitors in FIG. 7

| # | Name | Modification Pattern | Stem Length | Bicyclic Nucleotides | GalNAcs in loop | G1 |
| --- | --- | --- | --- | --- | --- | --- |
| 20 | LS/3GN | Pattern 1 | Long | None | 3 | 2'-OMe |
| 21 | SS/3GN-BNA | Pattern 1 | Short | BNA | 3 | 2'-OMe |

The long stem construct 20 has a stem duplex of 6 base pairs, whereas short stem construct 21 has a stem duplex of 3 base pairs containing 6 bicyclic nucleotides. While both construct 20 and 21 contain three GalNAc conjugated nucleotides in the tetraloop, the first three nucleotides of the tetraloop are GalNAc conjugated in construct 20 while the last three nucleotides are GalNAc conjugated in construct 21. Other than these differences, constructs 20 and 21 are identical. The bicyclic nucleotide used in construct 21 is BNA$^{NC}$ [NMe].

Figure 8:
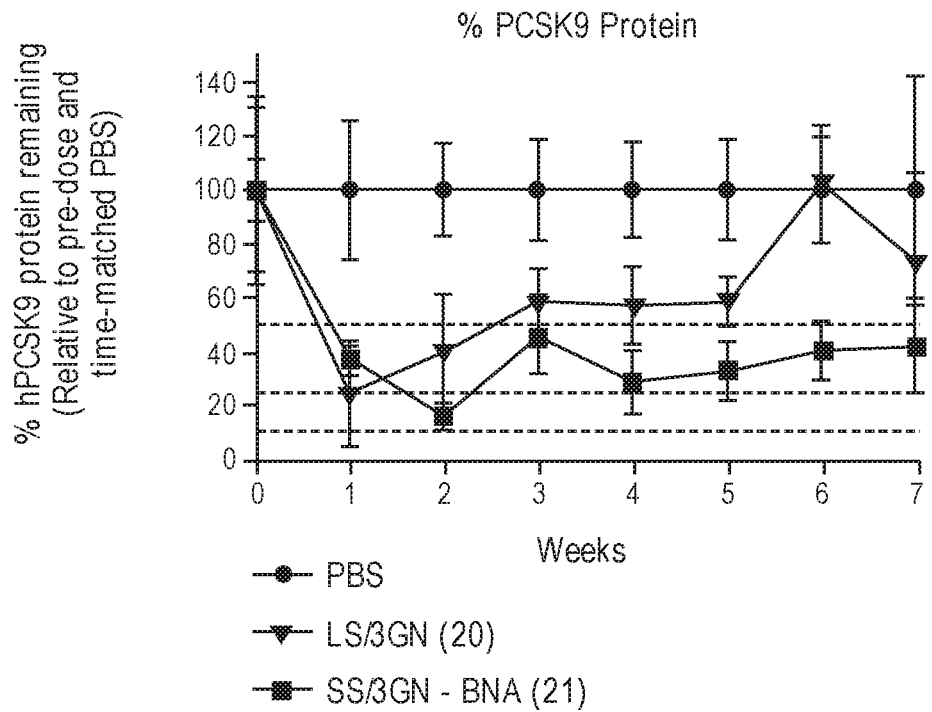
FIG. 8 shows the knockdown of human PCSK9 protein following administration of Constructs 20 and 21 (see FIG. 7) to C57BL/6 mice that were previously dosed with an AAV9 vector that expresses hPCSK9, as explained in Example 4. The inclusion of bicyclic nucleotides in the short stem of Construct 21 (SS/3GN-BNA) improved the potency and duration of PCSK9 knockdown as compared to the long stem control.

As shown in FIG. 8, PCSK9 nucleic acid inhibitor molecules containing bicyclic nucleotides in the short stem showed improved potency and duration (weeks 2-7) as compared to the corresponding long stem control.

Example 5: PCSK9 Inhibition in AAV Mouse Model Using Luciferase Reporter

In another experiment, C57BL/6J female mice were injected intravenously with a different AAV9 plasmid that expresses PCSK9 target sites in the 3'-untranslated region of *Gaussia* luciferase ($1\times10^{12}$ copies). The PCSK9 target sites are specific for the test nucleic acid inhibitor molecules used in this experiment. In this way, luciferase expression can be used to measure the ability of the test nucleic acid inhibitor molecules to mediate site-specific cleavage within the plasmid DNA. Animals were bled weekly via lateral tail vein puncture and blood was processed to serum. *Gaussia* luciferase expression was measured according to the manufacturer's protocol (Pierce™ *Gaussia* Luciferase Glow Assay kit, #16161, Thermo Fisher Scientific, Waltham, MA). When luciferase expression was stabilized, animals were dosed subcutaneously with 1 mg/kg of the assigned test article. Animals were bled weekly to determine the duration of knockdown.

The test PCSK9 nucleic acid inhibitor molecules used are shown in FIG. 5 (Constructs 17 and 19). The nucleotide sequences of the test PCSK9 nucleic acid inhibitor molecules are the same as those used in Examples 3 and 4. With the exception of the nucleotides in the loop that are conjugated to GalNAc and the bicyclic nucleotides, every other nucleotide in the test PCSK9 nucleic acid inhibitor molecules is modified at the 2'-position of the sugar moiety with either 2'-OMe or 2'-F (modification pattern 2 or "M2"). The test PCSK9 nucleic acid inhibitor molecules differed in the following respects: length of the stem portion (short vs. long) and presence or absence of bicyclic nucleotides. The PCSK9 nucleic acid inhibitor molecules used in this experiment are summarized in the following table:

TABLE 6

PCSK9 nucleic acid inhibitors (FIG. 5)

| # | Name | Modification Pattern | Stem Length | Bicyclic Nucleotides | GalNAcs in loop | G1 |
|---|------|---------------------|-------------|---------------------|-----------------|-----|
| 17 | LS/3GN | Pattern 2 | Long | None | 3 | 2'-OMe |
| 19 | SS/3GN-BNA | Pattern 2 | Short | BNA | 3 | 2'-OMe |

The short stem construct 19 is identical to the long stem construct 17 except that construct 17 has a stem duplex of 6 base pairs, whereas construct 19 has a stem duplex of 3 base pairs containing 6 bicyclic nucleotides. The bicyclic nucleotide used in construct 19 is BNA$^{NC}$ [NMe].

Figure 9:
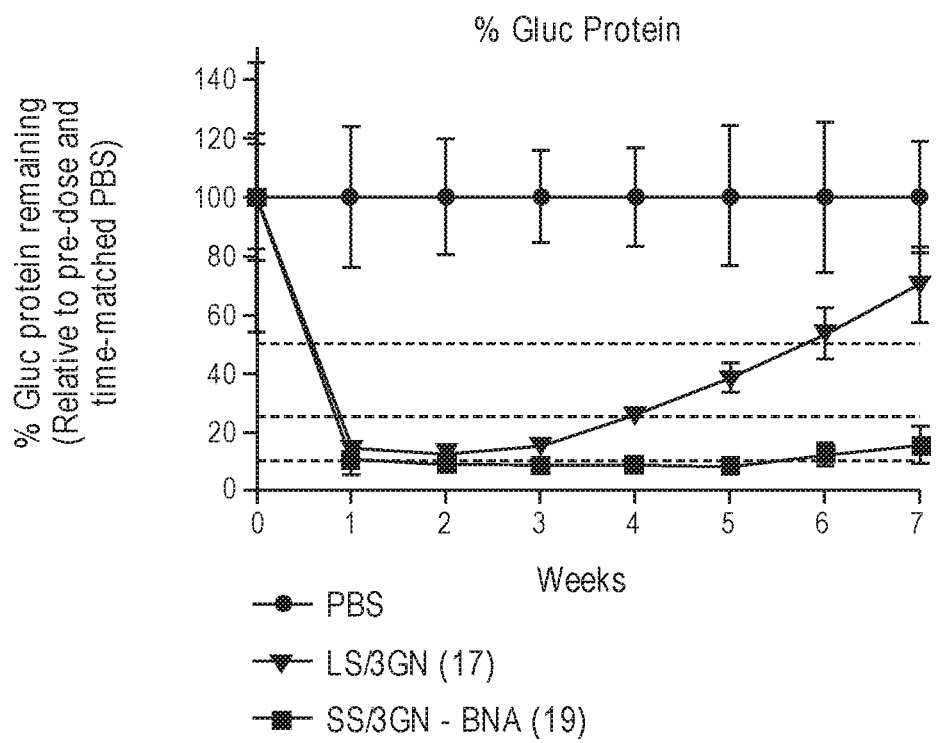
FIG. 9 shows the knockdown of *Gaussia* luciferase following administration of Constructs 17 and 19 (see FIG. 5) to C57BL/6 mice that were previously dosed with an AAV9 vector that expresses human PCSK9 target sites in the 3'-untranslated region of the *Gaussia* luciferase gene (reporter gene), as explained in Example 5. The inclusion of bicyclic nucleotides in the short stem of Construct 19 (SS/3GN-BNA) improved the duration of PCSK9-specific knockdown of the luciferase reporter gene as compared to the long stem control.

In this AAV mouse model, where mice were transfected with site-specific PCSK9 target sequences using an AAV9 plasmid, the nucleic acid inhibitor molecules containing bicyclic nucleotides in the short stem once again showed improved duration of potency as compared to the long stem control that did not contain any bicyclic nucleotides. The short stem construct 19 maintained luciferase levels below 20% through the entire 7-week study, whereas the luciferase levels increased to about 20% with long stem control (construct 17) by week 4 and steadily increased to about 70% by week 7. FIG. 9.

In a related study, additional test PCSK9 nucleic acid inhibitor molecules were tested in this AAV mouse model, as described above. The additional test PCSK9 nucleic acid inhibitor molecules are shown in FIGS. 14B-C and contain a shortened stem construct (3 base pairs) containing 3 BNA base pairs, 2 BNA base pairs, or 1 BNA base pair, or 3 unpaired BNAs, 2 unpaired BNAs or 1 BNA. Control PCSK9 nucleic acid inhibitor molecules without any BNA and containing a long stem construct (6 base pairs total) or a shortened stem construct (3 base pairs) were also tested (Constructs 17 and 18 from Example 3). FIG. 14A. While all test and control PCSK9 constructs exhibited potent knockdown of PCSK9 mRNA by two weeks, each of the BNA-containing shortened stem constructs exhibited improved potency and duration as compared to the parent, shortened stem construct containing no BNA, including construct 35 (FIG. 14C), which contains a single, unpaired BNA in the stem. FIGS. 15A-B. Furthermore, while a single BNA base pair in the shortened stem was enough to increase the duration and potency of PCSK9 mRNA knockdown, adding more BNA base pairs to the stem (e.g., 2 or 3 base pairs) did not appear to enhance the potency or duration further. FIG. 15A. In contrast, adding unpaired BNAs on one side of the stem appeared to increase PCSK9 mRNA knockdown activity as the number of consecutive BNAs in the stem increased. FIG. 15B.

Example 6: In Vivo Knockdown of ALDH2 Target Gene mRNA Using Nucleic Acid Inhibitor Molecules Containing Tetraloops and Triloops Additional constructs having either 3 or 4 nucleotides in the loop were designed to evaluate how reducing the length of the stem (D2) beyond three base pairs impacts mRNA knockdown activity. CD-1 female mice were divided into study groups and dosed with test nucleic acid inhibitor molecule assigned to that group. The test nucleic acid inhibitor molecules used in Example 6 (Constructs 22-30) are shown in FIGS. 11A-I. Except for the nucleotides in the loop that are conjugated to GalNAc and the bicyclic nucleotides, every other nucleotide in the test nucleic acid inhibitor molecules is modified at the 2'-position of the sugar moiety with either 2'-OMe or 2'-F. The test nucleic acid inhibitor molecules differed in the following respects: length of the stem portion (6 base pairs, 3 base pairs, 2 base pairs, and 1 base pair); presence or absence of bicyclic nucleotides; length of the loop portion (tetraloop vs. triloop); and number of GalNAcs in the loop. The nucleic acid inhibitor molecules in FIGS. 11A-I are summarized in the following table:

TABLE 7

Test nucleic acid inhibitors in FIG. 11

| FIG. | Name | Loop Length | Stem Length | Bicyclic nucleotides | GalNAcs |
|------|------|-------------|-------------|---------------------|---------|
| 11A | Construct 22 | 4 | 6 base pairs | None | 2 |
| 11B | Construct 23 | 3 | 6 base pairs | None | 2 |
| 11C | Construct 24 | 4 | 3 base pairs | BNA | 2 |
| 11D | Construct 25 | 3 | 3 base pairs | BNA | 2 |
| 11E | Construct 26 | 4 | 2 base pairs | BNA | 2 |
| 11F | Construct 27 | 3 | 2 base pairs | BNA | 2 |
| 11G | Construct 28 | 4 | 1 base pair | BNA | 2 |
| 11H | Construct 29 | 3 | 1 base pair | BNA | 2 |
| 11I | Construct 30 | 4 | 6 base pairs | None | 3 |

The long stem (6 base pairs) Constructs 22 and 23 are identical with the only difference being the number of nucleotides in the loop (tetraloop vs. triloop). Construct 30 is identical to Construct 22 except that Construct 30 contains 3 GalNAcs conjugated to the tetraloop, whereas Construct 22 contains 2 GalNAcs conjugated to the tetraloop. Construct 24 (3 base pair stem) is identical to Construct 25 (3 base pair stem) except that Construct 24 has a tetraloop, whereas Construct 25 has a triloop. Constructs 26 and 27 (2 base pair stem) are identical with the only difference being Construct 26 has a tetraloop, whereas construct 27 has a triloop. Constructs 28 and 29 (1 base pair stem) are identical with the only difference being Construct 28 has a tetraloop, whereas Construct 29 has a triloop. The bicyclic nucleotides used in Constructs 24-29 are BNA$^{NC}$ [NMe].

Animals were dosed subcutaneously with a single 0.5 mg/kg does of the assigned test nucleic acid inhibitor molecule, and the mice were sacrificed 4 days post-dose. Liver tissue was collected by taking two 4 mm punch biopsies which were stored in Invitrogen™ RNAlater™ solution (Thermo Fisher Scientific, Waltham, MA) for later mRNA analysis. Tissue samples were homogenized in QIAzol® Lysis Reagent using TissueLyser II (Qiagen, Valencia, CA). RNA was then purified using MagMAX Technology according to manufacturer instructions (ThermoFisher Scientific, Waltham, MA). High capacity cDNA reverse transcription kit (ThermoFisher Scientific, Waltham, MA) was used to prepare cDNA. Primers for the target sequence were used for PCR on a CFX384 Real-Time PCR Detection System (Bio-Rad Laboratories, Inc., Hercules, CA).

The short stem test nucleic acid inhibitor molecules (Constructs 24-29) were compared to corresponding long stem versions of the test nucleic acid molecules (Constructs 22, 23, and 30). As demonstrated in FIG. 12, the short stem constructs containing 3 base pairs (6 bicyclic nucleotides) or 2 base pairs (4 bicyclic nucleotides) in the stem (Constructs 24-27) showed similar knockdown of the target gene mRNA as compared to the long stem constructs containing 6 base pairs (and no bicyclic nucleotides) in the stem (Constructs 22, 23, and 30). On the other hand, the short stem constructs having 1 base pair (2 bicyclic nucleotides) in the stem (Constructs 28 and 29) exhibited markedly different mRNA inhibition activity depending on how many nucleotides were in the loop. Construct 29, containing a triloop, did not exhibit knockdown of the target gene mRNA, whereas Construct 28, containing a tetraloop, showed substantial knockdown of target gene mRNA. FIG. 12.

Example 7: In Vivo APOC3 Protein Knockdown in the Blood

CD-1 female mice were divided into study groups and dosed with the test Apolipoprotein $C_2$ (APOC3) nucleic acid inhibitor molecule assigned to that group. Animals were dosed subcutaneously with 1 mg/kg of the assigned APOC3 nucleic acid inhibitor molecule. Seven days after administration of the APOC3 nucleic acid inhibitor molecule, 10 μL of whole blood was collected via lateral tail venipuncture and diluted 50-fold in cold phosphate buffered saline (PBS). Diluted whole blood was further diluted 100-fold for a total of 5000-fold dilution of whole blood. The diluted whole blood was assayed for APOC3 protein using the Cloud-Clone Corporation enzyme-linked immunosorbent assay kit designed for mouse APOC3 (SEB890Mu) using the manufacturer's protocol. Concentrations of blood APOC3 in the experimental groups were back-calculated based on the kit's standard curve. Data was then transformed to show relative APOC3 in whole blood (%) compared to the negative control (PBS) group.

The test APOC3 nucleic acid inhibitor molecules used in this example are shown in FIG. 16. They contain a shortened stem construct (3 base pairs) with 3 BNA base pairs, 2 BNA base pairs, or 1 BNA base pair, or 3 unpaired BNAs, 2 unpaired BNAs or 1 BNA. A control APOC3 nucleic acid inhibitor molecule without any BNA and containing a long stem construct (6 base pairs total) was also tested. All BNA-containing constructs exhibited knockdown of APOC3 mRNA, as measured by APOC3 protein in the blood at day 7, although construct 36, containing 2 BNA base pairs was less effective at inhibiting APOC3 mRNA than the other BNA-containing constructs. FIG. 17.

What is claimed is:

1. A double-stranded nucleic acid inhibitor molecule, comprising:
   a sense strand comprising 21-66 nucleotides and having a first region (R1) and a second region (R2);
   an antisense strand comprising 15-40 nucleotides, wherein the sense strand and antisense strand are separate strands;
   a first duplex (D1) formed by the first region of the sense strand and the antisense strand, wherein the first duplex has a length of 15-40 base pairs;
   wherein the second region of the sense strand comprises a first subregion (S1), a second subregion (S2) and a tetraloop (L) comprising at least one ligand conjugated nucleotide that joins the first and second subregions, wherein the first and second subregions form a second duplex (D2); and
   wherein the second duplex has a length of 1-3 base pairs, wherein the second duplex contains 6 bicyclic nucleotides that form 3 base pairs, 4 bicyclic nucleotides that form 2 base pairs, 2 bicyclic nucleotides that form 1 base pair, 6 nucleotides that form 3 base pairs and include 3 unpaired bicyclic nucleotides, 6 nucleotides that form 3 base pairs and include 2 unpaired bicyclic nucleotides, or 6 nucleotides that form 3 base pairs and include 1 unpaired bicyclic nucleotide, and
   wherein every nucleotide on the sense strand and antisense strand is modified at the 2'-carbon of the sugar moiety with a 2'-F or a 2'-OMe, except for the bicyclic nucleotides in the second duplex and the nucleotides in the tetraloop that are conjugated to a sugar ligand moiety.

2. The double-stranded nucleic acid inhibitor molecule of claim 1, wherein the sense strand has 24-35, 28-35, or 26-30 nucleotides.

3. The double-stranded nucleic acid inhibitor molecule of claim 1, wherein the antisense strand has 18-24, 21-23, or 22 nucleotides.

4. The double-stranded nucleic acid inhibitor molecule of claim 1, wherein the antisense strand has a single stranded overhang of 1-6 nucleotides at its 3'-end.

5. The double-stranded nucleic acid inhibitor molecule of claim 4, wherein the single stranded overhang is 2 nucleotides in length.

6. The double-stranded nucleic acid inhibitor molecule of claim 1, wherein the first duplex has a length of 18-30, 18-24, or 19-21 base pairs.

7. The double-stranded nucleic acid inhibitor molecule of claim 1, wherein the sense strand is between 24-35 nucleotides in length, the antisense strand is between 20-24 nucleotides in length, the first duplex has a length of 18-24 base pairs.

8. The double-stranded nucleic acid inhibitor molecule of claim 1, wherein the sense strand is between 24-30 nucleotides in length, the antisense strand is between 20-24 nucleotides in length, the first duplex has a length of 18-24 base pairs.

9. The double-stranded nucleic acid inhibitor molecule of claim 1, wherein the second duplex has a length of 3 base pairs.

10. The double-stranded nucleic acid inhibitor molecule of claim 1, wherein the first region of the sense strand is 20 nucleotides in length and the second region of the sense strand is 10, 8, or 6 nucleotides in length;
   wherein the first duplex formed by the first region of the sense strand and the antisense strand has a length of 20 base pairs;
   wherein the tetraloop is 4 nucleotides in length; and
   wherein the antisense strand is 22 nucleotides in length and has a single-stranded overhang of two nucleotides at its 3'-end.

11. The double-stranded nucleic acid inhibitor molecule of claim 10, wherein the second region of the sense strand is 6 nucleotides in length and the second duplex has a length of 1 base pair.

12. The double-stranded nucleic acid inhibitor molecule of claim 1, wherein each nucleotide in the second duplex is the bicyclic nucleotide.

13. The double-stranded nucleic acid inhibitor molecule of claim 1, wherein the tetraloop is an RNA tetraloop selected from UNCG, GNRA, or CUUG, A/UGNN, GGUG, RNYA, or AGNN or a DNA tetraloop selected from d(GNAB), d(CNNG), or d(TNCG).

14. The double-stranded nucleic acid inhibitor molecule of claim 1, wherein the tetraloop has the sequence GAAA.

15. The double-stranded nucleic acid inhibitor molecule of claim 1, wherein the bicyclic nucleotide has the structure of Formula I, II, III, IV, Va, or Vb.

16. The double-stranded nucleic acid inhibitor molecule of claim 1, wherein the bicyclic nucleotide has the structure of Formula Ia, Ib, Ic, Id, Ie, or If.

17. The double-stranded nucleic acid inhibitor molecule of claim 1, wherein the bicyclic nucleotide has the structure of one or more of Formula IIa, IIb, IIc, or IId.

18. The double-stranded nucleic acid inhibitor molecule of claim 1, wherein the bicyclic nucleotide has the structure of one or more of Formula Ma or IIIb.

19. The double-stranded nucleic acid inhibitor molecule of claim 1, wherein the bicyclic nucleotide has the structure of one or more of Formula IVa or IVb.

20. The double-stranded nucleic acid inhibitor molecule of claim 1, wherein the bicyclic nucleotide is selected from the group consisting of:

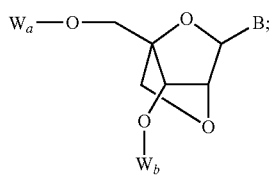

(a)

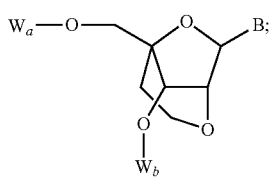

(b)

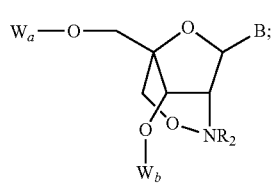

(c)

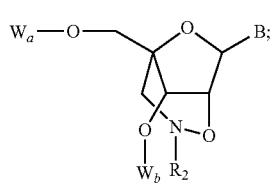

(d)

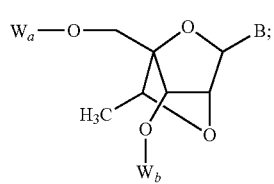

(e)

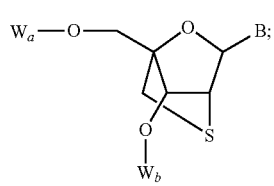

(f)

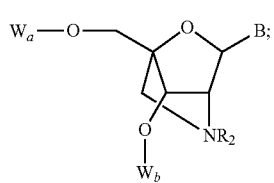

(g)

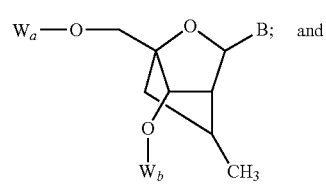

(h)

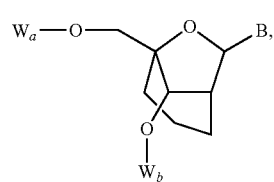

(i)

wherein B is a nucleobase, $R_2$ is H or $CH_3$ and $W_a$ and $W_b$ are each independently, H, OH, a hydroxyl protecting group, a phosphorous moiety, or an internucleotide linking group attaching the bicyclic nucleotide to another nucleotide or to an oligonucleotide and wherein at least one of $W_a$ or $W_b$ is an internucleotide linking group attaching the bicyclic nucleotide to an oligonucleotide.

21. The double-stranded nucleic acid inhibitor molecule of claim 20, wherein the bicyclic nucleotide is:

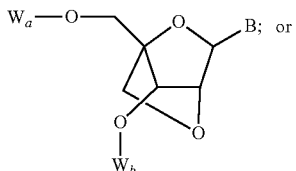

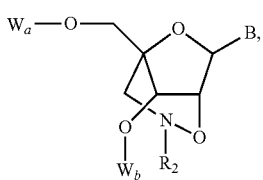

wherein B is a nucleobase, $R_2$ is $CH_3$ and $W_a$ and $W_b$ are each independently, H, OH, a hydroxyl protecting group, a phosphorous moiety, or an internucleotide linking group attaching the bicyclic nucleotide to another nucleotide or to an oligonucleotide and wherein at least one of $W_a$ or $W_b$ is an internucleotide linking group attaching the bicyclic nucleotide to an oligonucleotide.

22. The double-stranded nucleic acid inhibitor molecule of claim 20, wherein the bicyclic nucleotide is:

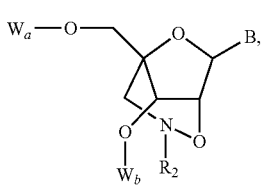

wherein B is a nucleobase, $R_2$ is $CH_3$ and $W_a$ and $W_b$ are each independently, H, OH, a hydroxyl protecting group, a phosphorous moiety, or an internucleotide linking group attaching the bicyclic nucleotide to another nucleotide or to an oligonucleotide and wherein at least one of $W_a$ or $W_b$ is an internucleotide linking group attaching the bicyclic nucleotide to an oligonucleotide.

23. The double-stranded nucleic acid inhibitor molecule of claim 1, wherein the bicyclic nucleotide comprises a first ring, wherein the first ring is a furanosyl and a bridge that connects the 2'-carbon and the 4'-carbon of the furanosyl to form a second ring.

24. The double-stranded nucleic acid inhibitor molecule of claim 23, wherein the bridge that connects the 2'-carbon and the 4'-carbon of the furanosyl is selected from the group consisting of:
 a) 4'-$CH_2$—O—N(R)-2' and 4'-$CH_2$—N(R)—O-2', wherein R is H, $C_1$-$C_{12}$ alkyl, or a protecting group, including, for example, 4'-$CH_2$—NH—O-2' (also known as $BNA^{NC}$) or 4'-$CH_2$—N($CH_3$)—O-2' (also known as $BNA^{NC}$[NMe]);
 b) 4'-$CH_2$-2'; 4'-$(CH_2)_2$-2'; 4'-$(CH_2)_3$-2'; 4'-$(CH_2)$—O-2' (also known as LNA); 4'-$(CH_2)$—S-2; 4'-$(CH_2)_2$-O-2' (also known as ENA); 4'-$CH(CH_3)$—O-2' (also known as cEt); and 4'-$CH(CH_2OCH_3)$—O-2' (also known as cMOE), and analogs thereof;
 c) 4'-$C(CH_3)(CH_3)$—O-2' and analogs thereof
 d) 4'-$CH_2$—N($OCH_3$)-2' and analogs thereof;
 e) 4'-$CH_2$—O—N($CH_3$)-2' and analogs thereof;
 f) 4'-$CH_2$—C(H)($CH_3$)-2' and analogs thereof; and
 g) 4'-$CH_2$—C(=$CH_2$)-2' and analogs thereof.

25. The double-stranded nucleic acid inhibitor molecule of claim 1, wherein the tetraloop comprises two, three, or four ligand conjugated nucleotides.

26. The double-stranded nucleic acid inhibitor molecule of claim 1, wherein the ligand is a GalNAc.

27. The double-stranded nucleic acid inhibitor molecule of claim 26, wherein the GalNAc is conjugated to the nucleotide at the 2'-position of the sugar moiety.

28. The double-stranded nucleic acid inhibitor molecule of claim 1, further comprising a 5'-phosphate mimic at the 5'-terminus of the sense strand and/or the antisense strand.

29. The double-stranded nucleic acid inhibitor molecule of claim 1, wherein the double-stranded nucleic acid inhibitor molecule is formulated with a lipid nanoparticle.

30. The double-stranded nucleic acid inhibitor molecule of claim 29, wherein the lipid nanoparticle comprises core lipids and envelope lipids, wherein the core lipids comprise a first cationic lipid and a first pegylated lipid and wherein the envelope lipids comprise a second cationic lipid, a neutral lipid, a sterol, and a second pegylated lipid.

31. The double-stranded nucleic acid inhibitor molecule of claim 30, wherein the first cationic lipid is DL-048, the first pegylated lipid is DSG-MPEG, the second cationic lipid is DL-103, the neutral lipid is DSPC, the sterol is cholesterol, and the second pegylated lipid is DSPE-MPEG.

32. A pharmaceutical composition comprising a therapeutically effective amount of the double-stranded nucleic acid inhibitor molecule of claim 1 and a pharmaceutically acceptable excipient.

33. A method for reducing expression of a target gene in a subject comprising administering the double-stranded nucleic acid inhibitor molecule or pharmaceutical composition of claim 32 to a subject in need thereof in an amount sufficient to reduce expression of the target gene.

34. The method of claim 33, wherein the administering comprises intravenous, intramuscular, or subcutaneous administration.

35. The method of claim 33, wherein the subject is a human.

36. The double-stranded nucleic acid inhibitor molecule of claim 24, wherein each nucleotide in the second duplex is the bicyclic nucleotide.

* * * * *

UNITED STATES PATENT AND TRADEMARK OFFICE
CERTIFICATE OF CORRECTION

PATENT NO. : 11,873,488 B2
APPLICATION NO. : 16/381931
DATED : January 16, 2024
INVENTOR(S) : Weimin Wang et al.

Page 1 of 1

It is certified that error appears in the above-identified patent and that said Letters Patent is hereby corrected as shown below:

In the Claims

In Claim 18, at Column 53, Line 43, "Ma" should be --IIIa--.

Signed and Sealed this
Twenty-seventh Day of February, 2024

Katherine Kelly Vidal
*Director of the United States Patent and Trademark Office*